(12) United States Patent
Desai et al.

(10) Patent No.: US 9,511,046 B2
(45) Date of Patent: Dec. 6, 2016

(54) METHODS OF TREATING PANCREATIC CANCER

(71) Applicant: Abraxis BioScience, LLC, Los Angeles, CA (US)

(72) Inventors: Neil P. Desai, Los Angeles, CA (US); Markus Renschler, San Francisco, CA (US)

(73) Assignee: ABRAXIS BIOSCIENCE, LLC, Los Angeles, CA (US)

(*) Notice: Subject to any disclaimer, the term of this patent is extended or adjusted under 35 U.S.C. 154(b) by 220 days.

(21) Appl. No.: 13/794,480

(22) Filed: Mar. 11, 2013

(65) Prior Publication Data

US 2014/0199403 A1 Jul. 17, 2014

Related U.S. Application Data

(60) Provisional application No. 61/751,820, filed on Jan. 11, 2013, provisional application No. 61/752,355, filed on Jan. 14, 2013.

(51) Int. Cl.
*A61K 31/337* (2006.01)
*A61K 31/7068* (2006.01)
*A61K 9/51* (2006.01)

(52) U.S. Cl.
CPC .......... *A61K 31/337* (2013.01); *A61K 9/5169* (2013.01); *A61K 31/7068* (2013.01)

(58) Field of Classification Search
CPC combination set(s) only.
See application file for complete search history.

(56) References Cited

U.S. PATENT DOCUMENTS

| | | | |
|---|---|---|---|
| 5,439,686 A | 8/1995 | Desai et al. | |
| 5,498,421 A | 3/1996 | Grinstaff et al. | |
| 5,505,932 A | 4/1996 | Grinstaff et al. | |
| 5,508,021 A | 4/1996 | Grinstaff et al. | |
| 5,512,268 A | 4/1996 | Grinstaff et al. | |
| 5,560,933 A | 10/1996 | Soon-Shiong et al. | |
| 5,635,207 A | 6/1997 | Grinstaff et al. | |
| 5,639,473 A | 6/1997 | Grinstaff et al. | |
| 5,650,156 A | 7/1997 | Grinstaff et al. | |
| 5,916,596 A | 6/1999 | Desai et al. | |
| 5,997,904 A | 12/1999 | Magdassi et al. | |
| 6,096,331 A | 8/2000 | Desai et al. | |
| 6,506,405 B1 | 1/2003 | Desai et al. | |
| 6,528,067 B1 | 3/2003 | Magdassi et al. | |
| 6,537,579 B1 | 3/2003 | Desai et al. | |
| 6,565,842 B1 | 5/2003 | Desai et al. | |
| 6,652,884 B2 | 11/2003 | Falciani | |
| 6,749,868 B1 | 6/2004 | Desai et al. | |
| 6,753,006 B1 | 6/2004 | Desai et al. | |
| 7,758,891 B2 | 7/2010 | Desai et al. | |
| 7,771,751 B2 | 8/2010 | Desai et al. | |
| 7,780,984 B2 | 8/2010 | Desai et al. | |
| 7,820,788 B2 | 10/2010 | Desai et al. | |
| 7,923,536 B2 | 4/2011 | Desai et al. | |
| 7,981,445 B2 | 7/2011 | De et al. | |
| 8,034,375 B2 | 10/2011 | Desai et al. | |
| 8,034,765 B2 | 10/2011 | De et al. | |
| 8,137,684 B2 | 3/2012 | Desai et al. | |
| 8,138,229 B2 | 3/2012 | Desai et al. | |
| 8,257,733 B2 | 9/2012 | Desai et al. | |
| 8,268,348 B2 | 9/2012 | Desai et al. | |
| 8,314,156 B2 | 11/2012 | Desai et al. | |
| 8,735,394 B2 | 5/2014 | Desai et al. | |
| 8,846,771 B2 | 9/2014 | Desai et al. | |
| 8,853,260 B2 | 10/2014 | Desai et al. | |
| 8,911,786 B2 | 12/2014 | Desai et al. | |
| 8,927,019 B2 | 1/2015 | Desai et al. | |
| 8,999,396 B2 | 4/2015 | Desai et al. | |
| 9,012,518 B2 | 4/2015 | Desai et al. | |
| 9,012,519 B2 | 4/2015 | Desai et al. | |
| 9,061,014 B2 | 6/2015 | Seward et al. | |
| 9,101,543 B2 | 8/2015 | Desai et al. | |
| 9,149,455 B2 | 10/2015 | Desai et al. | |
| 2006/0263434 A1 | 11/2006 | Desai et al. | |
| 2007/0082838 A1 | 4/2007 | De et al. | |
| 2007/0166388 A1 | 7/2007 | Desai et al. | |
| 2010/0048499 A1 | 2/2010 | Desai et al. | |
| 2010/0310507 A1* | 12/2010 | Trieu et al. | 424/85.2 |
| 2011/0118342 A1 | 5/2011 | De et al. | |
| 2011/0151012 A1 | 6/2011 | Desai et al. | |
| 2012/0070502 A1 | 3/2012 | Desai et al. | |
| 2012/0076862 A1 | 3/2012 | Desai et al. | |
| 2012/0128732 A1 | 5/2012 | Trieu et al. | |
| 2012/0189701 A1 | 7/2012 | Desai et al. | |
| 2012/0283205 A1 | 11/2012 | Desai et al. | |
| 2012/0308612 A1 | 12/2012 | De et al. | |
| 2013/0005678 A1 | 1/2013 | Sandvold et al. | |

(Continued)

FOREIGN PATENT DOCUMENTS

AU 2012201568 A1 3/2012
WO WO-94/18954 A1 9/1994

(Continued)

OTHER PUBLICATIONS

US 8,968,752, 03/2015, Desai et al. (withdrawn)
Altmayer, P. et al. (Oct. 1995). "Propofol Binding to Human Blood Proteins," *Arzneimittelforschung/Drug Research* 45(II):1053-1056.
Carter, D.C. et al. (1994). "Structure of Serum Albumin," *Adv. Protein Chem.* 45:153-203.
Curry, S. et al. (Sep. 1998). "Crystal Structure of Human Serum Albumin Complexed With Fatty Acid Reveals an Asymmetric Distribution of Binding Sites," *Natl. Struct. Biol.* 5(9):827-835.
Eisenhauer, E.A. et al. (Jan. 2009). "New Response Evaluation Criteria in Solid Tumours: Revised RECIST Guideline (Version 1.1)," *Eur. J. Cancer* 45(2):228-247.

(Continued)

*Primary Examiner* — Michael G Hartley
*Assistant Examiner* — Robert Cabral
(74) *Attorney, Agent, or Firm* — Morrison & Foerster LLP

(57) ABSTRACT

Provided herein are methods for the treatment of metastatic pancreatic cancer comprising administration of a composition comprising nanoparticles comprising a taxane (such as paclitaxel) and a carrier protein in combination with gemcitabine.

34 Claims, 8 Drawing Sheets

(56) References Cited

U.S. PATENT DOCUMENTS

| | | |
|---|---|---|
| 2013/0045240 A1 | 2/2013 | Tao et al. |
| 2013/0071438 A1 | 3/2013 | Desai et al. |
| 2013/0115296 A1 | 5/2013 | Yeo et al. |
| 2013/0195922 A1 | 8/2013 | Desai et al. |
| 2013/0195983 A1 | 8/2013 | Desai et al. |
| 2013/0195984 A1 | 8/2013 | Desai et al. |
| 2013/0202709 A1 | 8/2013 | Desai et al. |
| 2013/0209518 A1 | 8/2013 | Desai et al. |
| 2013/0244952 A1 | 9/2013 | Desai et al. |
| 2013/0266659 A1 | 10/2013 | Desai et al. |
| 2013/0280336 A1 | 10/2013 | Desai et al. |
| 2013/0280337 A1 | 10/2013 | Desai et al. |
| 2014/0017315 A1 | 1/2014 | Desai et al. |
| 2014/0017316 A1 | 1/2014 | Desai et al. |
| 2014/0017323 A1 | 1/2014 | Desai et al. |
| 2014/0023717 A1 | 1/2014 | Desai et al. |
| 2014/0039069 A1 | 2/2014 | Desai et al. |
| 2014/0039070 A1 | 2/2014 | Desai et al. |
| 2014/0056986 A1 | 2/2014 | Desai et al. |
| 2014/0072630 A1 | 3/2014 | Tao et al. |
| 2014/0072631 A1 | 3/2014 | Trieu et al. |
| 2014/0072643 A1 | 3/2014 | Desai et al. |
| 2014/0079787 A1 | 3/2014 | Yeo et al. |
| 2014/0079788 A1 | 3/2014 | Desai et al. |
| 2014/0079793 A1 | 3/2014 | Desai et al. |
| 2014/0080901 A1 | 3/2014 | Desai et al. |
| 2014/0134257 A1 | 5/2014 | Desai et al. |
| 2014/0155344 A1 | 6/2014 | Desai et al. |
| 2014/0170228 A1 | 6/2014 | Desai et al. |
| 2014/0186447 A1 | 7/2014 | Desai |
| 2014/0199404 A1 | 7/2014 | Heise et al. |
| 2014/0199405 A1 | 7/2014 | Pierce et al. |
| 2014/0271871 A1 | 9/2014 | Desai et al. |
| 2014/0296279 A1 | 10/2014 | Seward et al. |
| 2014/0296353 A1 | 10/2014 | Desai et al. |
| 2014/0302157 A1 | 10/2014 | Desai et al. |
| 2015/0050356 A1 | 2/2015 | Desai et al. |
| 2015/0079181 A1 | 3/2015 | Desai et al. |
| 2015/0104521 A1 | 4/2015 | Desai et al. |
| 2015/0111960 A1 | 4/2015 | Desai et al. |
| 2015/0157722 A1 | 6/2015 | Foss et al. |
| 2015/0165047 A1 | 6/2015 | Desai et al. |
| 2015/0190519 A1 | 7/2015 | Desai et al. |
| 2015/0313866 A1 | 11/2015 | Desai et al. |
| 2016/0008330 A1 | 1/2016 | Desai et al. |
| 2016/0015681 A1 | 1/2016 | Desai et al. |
| 2016/0015817 A1 | 1/2016 | Benettaib et al. |

FOREIGN PATENT DOCUMENTS

| | | |
|---|---|---|
| WO | WO-98/14174 A1 | 4/1998 |
| WO | WO-98/14175 A1 | 4/1998 |
| WO | WO-99/00113 A1 | 1/1999 |
| WO | WO-00/64437 A1 | 11/2000 |
| WO | WO-00/71079 A2 | 11/2000 |
| WO | WO-00/71079 A3 | 11/2000 |
| WO | WO-01/89522 A1 | 11/2001 |
| WO | WO-02/087545 A1 | 11/2002 |
| WO | WO-03/096944 A1 | 11/2003 |
| WO | WO-2004/052401 A2 | 6/2004 |
| WO | WO-2004/052401 A3 | 6/2004 |
| WO | WO-2006/089290 A1 | 8/2006 |
| WO | WO-2007/027819 A2 | 3/2007 |
| WO | WO-2007/027819 A3 | 3/2007 |
| WO | WO-2007/027941 A2 | 3/2007 |
| WO | WO-2007/027941 A3 | 3/2007 |
| WO | WO-2008/027055 A1 | 3/2008 |
| WO | WO-2008/057562 A1 | 5/2008 |
| WO | WO-2008/076373 A1 | 6/2008 |
| WO | WO-2008/109163 A1 | 9/2008 |
| WO | WO-2008/137148 A2 | 11/2008 |
| WO | WO-2008/137148 A3 | 11/2008 |
| WO | WO-2008/150532 A1 | 12/2008 |
| WO | WO-2009/126175 A1 | 10/2009 |
| WO | WO-2009/126401 A1 | 10/2009 |
| WO | WO-2009/126938 A1 | 10/2009 |
| WO | WO-2010/068925 A1 | 6/2010 |
| WO | WO-2010/105172 A1 | 9/2010 |
| WO | WO-2010/118365 A1 | 10/2010 |
| WO | WO-2010/121000 A1 | 10/2010 |
| WO | WO-2011/123393 A1 | 10/2011 |
| WO | WO-2011/123395 A1 | 10/2011 |
| WO | WO-2011/153009 A1 | 12/2011 |
| WO | WO-2011/153010 A1 | 12/2011 |
| WO | WO-2011/156119 A1 | 12/2011 |
| WO | WO-2012/149451 A1 | 11/2012 |
| WO | WO-2013/090634 A1 | 6/2013 |
| WO | WO-2014/105644 A1 | 7/2014 |
| WO | WO-2014/110345 A1 | 7/2014 |
| WO | WO-2014/110408 A1 | 7/2014 |
| WO | WO-2014/110443 A1 | 7/2014 |
| WO | WO-2014/123612 A1 | 8/2014 |
| WO | WO-2014/143613 A1 | 9/2014 |
| WO | WO-2014/151853 A1 | 9/2014 |
| WO | WO-2014/159171 A1 | 10/2014 |
| WO | WO-2015/157120 A1 | 10/2015 |

OTHER PUBLICATIONS

Fehske, K.J. et al. (1981). "Commentary: The Location of Drug Binding Sites in Human Serum Albumin," *Biochem. Pharmcol.* 30(7):687-692.

Finlayson, J.S. (1980). "Albumin Products," *Seminars in Thrombosis and Hemostasis* 6(2):85-120.

Garrido, M.J. et al. (1994). "Binding Characteristics of Propofol to Plasma Proteins and Possible Interactions," *Rev. Esp. Anestestiol. Reanim.* 41(6):308-312.

Hauser, C.J. et al. (Jun. 1980). "Oxygen Transport Responses to Colloids and Crystalloids in Critically Ill Surgical Patients," *Surgery Gynecology & Obstetrics* 150(6):811-816.

He, X.M. et al. (Jul. 16, 1992). "Atomic Structure and Chemistry of Human Serum Albumin," *Nature* 358:209-215.

International Search Report mailed on Apr. 17, 2014, for PCT Application No. PCT/US2014/01145, filed on Jan. 10, 2014, 4 pages.

Kim, S-O. et al. (2005). "Superior Antitumor Efficacy of Genexol ®-PM, a Biodegradable Polymeric Micelle-based Formulation of Paclitaxel (Genexol®) Compared with Gemzar® (Gemcitabine) and Taxol® in Human Pancreatic Cancer Cells in vitro and in vivo," *Proc. Amer. Assoc. Cancer Res.* 46: Abstract No. 1440, two pages.

Kragh-Hansen, U. (Feb. 1990). "Structure and Ligand Binding Properties of Human Serum Albumin," *Danish Medical Bulletin* 37(1):57-84.

Loehr, M. et al. (May 20, 2009). "Cationic Liposomal Paclitaxel in Combination with Gemcitabine in Patients with Advanced Pancreatic Cancer: A Phase II: Trial," *J. Clinical Oncology* 27(15S):200, Abstract 4526, one page.

Maitra, A. et al. (Dec. 2009). "Abstract C246: nab®-Paclitaxel Targets Tumor Stroma and Results, Combined with Gemcitabine, in High Efficacy Against Pancreastic Cancer Models," *Mol. Cancer Ther.* 8(12 Supp. 1): Abstract C246, two pages.

Moore, M.J. et al. (May 20, 2007). "Erlotinib Plus Gemcitabine Compared with Gemcitabine Alone in Patients with Advanced Pancreatic Cancer: A Phase III Trial of the National Cancer Institute of Canada Clinical Trials Group," *J. Clinical Oncol.* 25(15):1960-1966.

Paal, K. et al. (2001). "High Affinity Binding of Paclitaxel to Human Serum Albumin," *Eur. J. Biochem.* 268(7):2187-2191.

Purcell, M. et al. (2000). "Interaction of Taxol With Human Serum Albumin," *Biochim. et Biophys. Acta* 1478:61-68.

Spratlin, J. et al. (Oct. 15, 2004). "The Absence of Human Equilibrative Nucleoside Transporter 1 is Associated with Reduced Survival in Patients with Gemcitabine-Treated Pancreas Adenocarcinoma," *Clinical Cancer Research* 10:6956-6961.

Sugio, S. et al. (1999.) "Crystal Structure of Human Serum Albumin at 2.5 Å Resolution," *Protein Eng.* 12(6):439-446.

Tullis, J.L. (Jan. 24, 1977). "Albumin 1. Background and Use," *JAMA* 237(4):355-360.

Tullis, J.L. (Jan. 31, 1977). "Albumin 2. Guidelines for Clinical Use," *JAMA* 237(5):460-463.

(56) References Cited

OTHER PUBLICATIONS

Urien, S. et al. (1996). "Docetaxel Serum Protein Binding with High Affinity to Alpha1-Acid Glycoprotein," *Invest. New Drugs* 14:147-151.

Von Hoff, D.D. et al. (May 20, 2009, e-pub. Oct. 3, 2011). "SPARC Correlation with Response to Gemcitabine (G) Plus nab-paclitaxel (nab-P) in Patients with Advanced Metastatic Pancreatic Cancer: A Phase I/II Study," *J. Clinical Oncology* 27(15S): Abstract 4525, three pages.

Von Hoff, D.D. et al. (Dec. 1, 2011, e-pub. Oct. 3, 2011). "Gemcitabine Plus nab-Paclitaxel Is an Active Regimen in Patients With Advanced Pancreatic Cancer: A Phase I/II Trial," *Journal of Clinical Oncology* 29(34):4548-4554.

Von Hoff, D.D. et al. (2012). "Randomized Phase III Study of Weekly nab-paclitaxel Plus Gemcitabine Versus Gemcitabine Alone in Patients with Metastatic Adenocarcinoma of the Pancreas (MPACT)," *Journal of Clinical Oncology* vol. 30 (suppl 34): Abstract LBA148.

Vorum, H. (Nov. 1999). "Reversible Ligand Binding to Human Serum Albumin," *Danish Medical Bulletin* 46(5):379-399.

Written Opinion mailed on Apr. 17, 2014, for PCT Application No. PCT/US2014/01145, filed on Jan. 10, 2014, 7 pages.

Nieto, J. et al. (2008). "Metastatic Pancreatic Cancer 2008: Is the Glass Less Empty?", *The Oncologist*, 13:562-576.

U.S. Appl. No. 14/273,319, filed May 8, 2014, for Desai et al. (copy not attached).

U.S. Appl. No. 14/362,382, filed Jun. 2, 2014, for Foss et al. (copy not attached).

U.S. Appl. No. 14/468,127, filed Aug. 25, 2014, for Desai et al. (copy not attached).

U.S. Appl. No. 14/505,452, filed Oct. 2, 2014, for Desai et al. (copy not attached).

U.S. Appl. No. 14/626,678, filed Feb. 19, 2015, by Desai et al. (Copy not attached).

U.S. Appl. No. 14/631,671, filed Feb. 25, 2015, by Desai et al. (Copy not attached).

U.S. Appl. No. 14/660,872, filed Mar. 17, 2015, by Desai et al. (Copy not attached).

F. Hoffmann-La Roche. (2013). "Understanding Clinical Trials," located at <http://www.roche.com/understanding_clinical_trials.pdf>, last visited on Mar. 6, 2016, 13 pages.

Ko, A.H. et al. (2012). "A Phase I Trial of Nab-Paclitaxel, Gemcitabine, and Capecitabine for Metastatic Pancreatic Cancer," *Cancer Chemotherapy and Pharmacology* 70:875-881.

Saif, M.W. (Mar. 10, 2013). Advancements in the Management of Pancreatic Cancer:2013, *J Pancreas* (Online), located at http://www.serena.uninait/index.php/jop/article/view/1481/1532, last visited on Jan. 13, 2016, 14(2):112-118, (15 pages).

Zhang, D.S. et al.(2013, e-pub. Mar. 13, 2013). "Phase I/II Study of Albumin-Bound *Nab*-Paclitaxel Plus Gemcitabine Administered to Chinese Patients With Advanced Pancreatic Cancer," *Cancer Chemotherapy and Pharmacology* 71(4):1065-1072.

Non-Final Office Action mailed on Feb. 11, 2015, for U.S. Appl. No. 13/701,001, Internationally filed May 20, 2011, 15 pages.

Non-Final Office Action mailed on Feb. 12, 2015, for U.S. Appl. No. 13/782,992, filed Mar. 1, 2013, 15 pages.

Final Office Action dated Aug. 5, 2015 for U.S. Appl. No. 13/794,486, filed Mar. 11, 2013, 16 pages.

U.S. Appl. No. 14/714,131, filed May 15, 2015, by Seward et al. (Copy not attached).

U.S. Appl. No. 14/834,331, filed Aug. 24, 2015, by Desai et al. (Copy not attached).

U.S. Appl. No. 14/835,458, filed Aug. 25, 2015, by Desai et al. (Copy not attached).

Murata, Y. et al. (2012, e-pub. Sep. 7, 2011). "Human 1-15 Equilibrative Nucleoside Transporter 1 Expression is a Strong Independent Prognostic Factor in UICC T3-T4 Pancreatic Cancer Patients Treated With Preoperative Gemcitabine-Based Chemoradiotherapy," *Journal of Hepato-Biliary-Pancreatic Sciences* 19(4):413-425.

Von Hoff, D.D. et al. (Oct. 31, 2013). "Increased Survival in Pancreatic Cancer with nab-Paclitaxel Plus Gemcitabine," *New England Journal of Medicine* 369(18):1691-1703.

Extended European Search Report mailed on May 3, 2016, for European Patent Application No. 14737791.5, filed on Jan. 10, 2014, 8 pages.

\* cited by examiner

METHODS OF TREATING PANCREATIC CANCER

RELATED APPLICATIONS

This application claims priority from U.S. Provisional Patent Application No. 61/751,820, filed Jan. 11, 2013, and U.S. Provisional Patent Application No. 61/752,355, filed Jan. 14, 2013, the contents of which are incorporated herein by reference in its entirety.

TECHNICAL FIELD

The present invention relates to methods, compositions, and kits for the treatment of pancreatic cancer by administering compositions comprising nanoparticles comprising a taxane (such as paclitaxel) and a carrier protein in combination with gemcitabine.

BACKGROUND

Pancreatic cancer has one of the highest mortality rates among all cancers and is expected to cause an estimated 37,390 deaths in the United States in 2012. See American Cancer Society, *Cancer Facts and Figures* 2012. For all stages of pancreatic cancer combined, the 1- and 5-year relative survival rates are 26% and 6%, respectively; this high mortality rate from pancreatic cancer is, at least in part, due to the high incidence of metastatic disease at the time of diagnosis. See id. As a result, treatment options for pancreatic cancer are very limited.

The standard first-line treatment for treating pancreatic cancer is gemcitabine (e.g., GEMZAR®), which was approved by the Food and Drug Administration ("FDA") in 1996. In a clinical study with 126 patients with locally advanced pancreatic cancer (63 treated with gemcitabine), gemcitabine was shown to be superior to 5-fluororuracil (5-FU) in terms of median overall survival (5.7 months for gemcitabine versus 4.2 months for 5-FU), median time to disease progression (2.1 months for gemcitabine versus 0.9 months for 5-FU), and clinical benefit responses. However, although gemcitabine has become a standard palliative therapy for treating pancreatic cancer since its approval in 1996, there has been little improvement in pancreatic cancer treatment.

The gemcitabine/erlotinib combination improved the median overall survival (6.4 months versus 6.0 months) and median progression free survival (3.8 months versus 3.5 months) over gemcitabine monotherapy. See Moore et al., J. Clin. Oncol. 25:1960-1966 (2007). Based on this very modest improvement in overall survival and progression free survival (0.4 and 0.3 months, respectively), the FDA approved the gemcitabine/erlotinib combination in 2005. Despite its approval, the gemcitabine/erlotinib combination has not been widely used as a standard of care for treating pancreatic cancer because of side effects associated with the gemcitabine/erlotinib combination and the minimal improvement on survival over gemcitabine monotherapy. See Nieto et al., *The Oncologist*, 13:562-576 (2008).

Albumin-based nanoparticle compositions have been developed as a drug delivery system for delivering substantially water insoluble drugs such as a taxanes. See, for example, U.S. Pat. Nos. 5,916,596; 6,506,405; 6,749,868, and 6,537,579, 7,820,788, and 7,923,536. Abraxane®, an albumin stabilized nanoparticle formulation of paclitaxel, was approved in the United States in 2005 and subsequently in various other countries for treating metastatic breast cancer. It was recently approved for treating non-small cell lung cancer in the United States, and has also shown therapeutic efficacy in various clinical trials for treating difficult-to-treat cancers such as pancreatic cancer and melanoma. Albumin derived from human blood has been used for the manufacture of Abraxane® as well as various other albumin-based nanoparticle compositions.

Albumin bound paclitaxel (e.g., Abraxane®) in combination with gemcitabine was found to be well tolerated in advanced pancreatic cancer in a Phase I/II study and showed evidence of antitumor activity. See, for example, US Patent App.; No. 2006/0263434; Maitra et al., *Mol. Cancer Ther.* 8(12 Suppl): C246 (2009); Loehr et al., *J. of Clinical Oncology* 27 (15S) (May 20 Supplement): 200, Abstract No. 4526 (2009); Von Hoff et al., *J. of Clinical Oncology* 27(15S) (May 20 Supplement), Abstract No. 4525 (2009); and Kim et al., *Proc. Amer. Assoc. Cancer Res.*, 46, Abstract No. 1440 (2005).

The disclosures of all publications, patents, patent applications and published patent applications referred to herein are hereby incorporated herein by reference in their entirety.

SUMMARY OF THE INVENTION

Provided herein are methods of treating metastatic pancreatic cancer in an individual (such as human individual) comprising administering to the individual (i) an effective amount of a composition comprising nanoparticles comprising a taxane (such as paclitaxel) and an albumin; and (ii) an effective amount of gemcitabine. In some embodiments, there is provided a method of treating locally advanced unresectable pancreatic cancer in an individual (such as a human individual) comprising administering to the individual (i) an effective amount of a composition comprising nanoparticles comprising a taxane (such as paclitaxel) and an albumin; and (ii) an effective amount of gemcitabine. In some embodiments, according to (or as applied to) any of the embodiments described herein, the pancreatic cancer is pancreatic adenocarcinoma.

In some embodiments according to (or as applied to) any of the embodiments above, the individual is a female. In some embodiments, the individual is a male. In some embodiments, the individual is under about 65 years old (such as under about any of 60, 55, 50, 45, or 40 years old). In some embodiments, the individual is at least about 65 years old (such as at least about any of 70, 75, or 80 years old).

In some embodiments according to (or as applied to) any of the embodiments above, the primary location of the pancreatic cancer is the head of the pancreas. In some embodiments, the primary location of the pancreatic cancer is the body of the pancreas. In some embodiments, the primary location of the pancreatic cancer is the tail of the pancreas.

In some embodiments according to (or as applied to) any of the embodiments above, the individual has metastasis in the liver. In some embodiments, the individual has pulmonary metastasis. In some embodiments, the individual has peritoneal carcinomatosis.

In some embodiments according to (or as applied to) any of the embodiments above, the individual has stage IV pancreatic cancer at the time of diagnosis of pancreatic cancer.

In some embodiments according to (or as applied to) any of the embodiments above, the individual has 3 or more metastatic sites. In some embodiments, the individual has more than 3 (such as any of 4, 5, 6, or more) metastatic sites.

In some embodiments according to (or as applied to) any of the embodiments above, the individual has a serum CA19-9 level that is ≥59×ULN (Upper Limit of Normal).

In some embodiments according to (or as applied to) any of the embodiments above, the individual has Karnofsky performance status (KPS) of less than about 90 (for example between about 70 and about 80, for example 70-80).

In some embodiments according to (or as applied to) any of the embodiments above, the individual has an increased (high) level of hENT1. In some embodiments, the individual has a decreased (low) level of hENT1.

In some embodiments according to (or as applied to) any of the embodiments above, the composition comprising nanoparticles comprising the taxane (such as paclitaxel) and an albumin is administered intravenously (for example by intravenous infusion over about 30 to about 40 minutes). In some embodiments, the dose of taxane (such as paclitaxel) in the nanoparticle composition is about 50 mg/m$^2$ to about 400 mg/m$^2$. In some embodiments, the dose of taxane (such as paclitaxel) in the nanoparticle composition is about 100 mg/m$^2$ to about 200 mg/m$^2$. In some embodiments, the dose of taxane (such as paclitaxel) in the nanoparticle composition is about 125 mg/m$^2$. In some embodiments, the composition comprising nanoparticles comprising taxane (such as paclitaxel) and an albumin is administered weekly. In some embodiments, the composition comprising nanoparticles comprising taxane (such as paclitaxel) and an albumin is administered weekly, three out of four weeks. In some embodiments, the albumin is human serum albumin. In some embodiments, the nanoparticles in the composition have an average diameter of no greater than about 200 nm. In some embodiments, the weight ratio of an albumin and taxane (such as paclitaxel) in the nanoparticle composition is about 9:1 or less. In some embodiments, the weight ratio of an albumin and taxane (such as paclitaxel) in the nanoparticle composition is about 9:1. In some embodiments, the taxane (such as paclitaxel) in the nanoparticles is coated with the albumin.

In some embodiments according to (or as applied to) any of the embodiments above, the gemcitabine is administered intravenously (for example by intravenous infusion over about 30 to about 40 minutes). In some embodiments, the gemcitabine is administered to the individual at about 500 mg/m$^2$ to about 2000 mg/m$^2$. In some embodiments, the gemcitabine is administered to the individual at about 750 mg/m$^2$ to about 1500 mg/m$^2$. In some embodiments, gemcitabine is administered to the individual at about 1000 mg/m$^2$. In some embodiments, gemcitabine is administered weekly. In some embodiments, the gemcitabine is administered weekly, three out of four weeks. In some embodiments, the administration of gemcitabine is immediately after the completion of the administration of the nanoparticle composition.

In some embodiments according to (or as applied to) any of the embodiments above, the method further comprises administering another chemotherapeutic agent.

In some embodiments, there is provided a method of treating metastatic or locally advanced pancreatic cancer in a human individual comprising administering to the individual (a) an effective amount of a composition comprising nanoparticles comprising paclitaxel and an albumin; and (b) an effective amount of gemcitabine, wherein the individual is selected for treatment based on (i) having metastasis in the liver, (ii) having 3 or more metastatic sites, (iii) having pancreatic cancer in the primary location in the head of the pancreas, and/or (iv) having serum CA19-9 level that is ≥59×ULN (Upper Limit of Normal).

In some embodiments, the pancreatic cancer is pancreatic adenocarcinoma. In some embodiments, the individual has Karnofsky performance status (KPS) of between 70 and 80. In some embodiments, the individual has a high level of hENT1.

In some embodiments, the composition comprising nanoparticles comprising paclitaxel and an albumin is administered intravenously. In some embodiments, the dose of paclitaxel in the nanoparticle composition is about 50 mg/m$^2$ to about 200 mg/m$^2$, for example about 125 mg/m$^2$. In some embodiments, the composition comprising nanoparticles comprising paclitaxel and albumin is administered weekly, three out of four weeks.

In some embodiments, the albumin is human albumin, such as human serum albumin. In some embodiments, the nanoparticles in the composition have an average diameter of no greater than about 200 nm. In some embodiments, the weight ratio of albumin and paclitaxel in the nanoparticle composition is about 9:1 or less (such as about 9:1). In some embodiments, the paclitaxel in the nanoparticles is coated with the albumin.

In some embodiments, the gemcitabine is administered to the individual at about 500 mg/m$^2$ to about 2000 mg/m$^2$, for example about 1000 mg/m$^2$. In some embodiments, the gemcitabine is administered weekly, three out of four weeks. In some embodiments, the gemcitabine is administered intravenously.

In some embodiments, the method further comprises selecting the individual for treatment based on the individual (i) having metastasis in the liver, (ii) having 3 or more metastatic sites, (iii) having pancreatic cancer in the primary location in the head of the pancreas, and/or (iv) having serum CA19-9 level that is ≥59×ULN (Upper Limit of Normal).

In some embodiments, the method further comprisesdetermining (i) the metastasis status, (ii) primary location of the pancreas, and/or (iii) CA19-9 level in the individual.

In some embodiments according to (or as applied to) any of the embodiments above, the method is for first-line treatment.

In some embodiments, there is provided a kit comprising (a) an effective amount of a composition comprising nanoparticles comprising paclitaxel and an albumin; and (b) an effective amount of gemcitabine, and (c) an instruction for using the nanoparticle composition and gemcitabine for treating metastatic or locally advanced pancreatic cancer in a human individual, wherein the individual is selected for treatment based on (i) having metastasis in the liver, (ii) having 3 or more metastatic sites, (iii) having pancreatic cancer in the primary location in the head of the pancreas, and/or (iv) having serum CA19-9 level that is ≥59×ULN (Upper Limit of Normal).

It is to be understood that one, some, or all of the properties of the various embodiments described herein may be combined to form other embodiments of the present invention. These and other aspects of the invention will become apparent to one of skill in the art.

DETAILED DESCRIPTION

Figure 1:
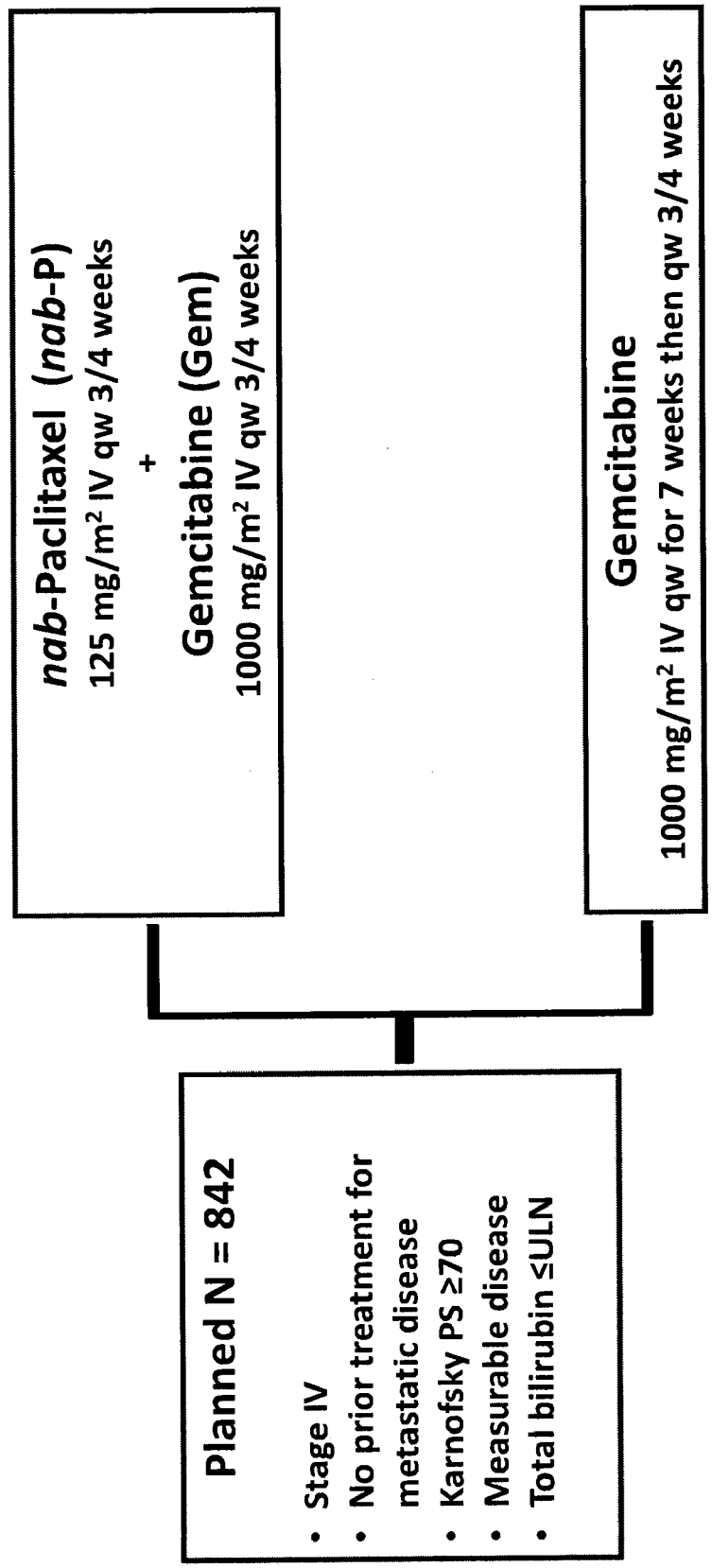
FIG. 1 shows the study design for a randomized phase III study of weekly Nab-paclitaxel (Abraxane®) plus gemcitabine versus gemcitabine alone in patients with metastatic adenocarcinoma of the pancreas ("MPACT study").

Provided herein are methods for treatment of pancreatic cancer in an individual using a composition comprising nanoparticles comprising a taxane (such as paclitaxel) and a carrier protein in combination with gemcitabine.

A phase III study using an albumin stabilized nanoparticle formulation of paclitaxel (Nab-paclitaxel, or Abraxane®) in combination with gemcitabine versus gemcitabine alone was conducted in patients with metastatic adenocarcinoma of the pancreas. Gemcitabine (e.g., GEMZAR®) is the standard first-line treatment for treating pancreatic cancer. The study showed that the median survival in the intent-to-treat analysis was 8.5 months in the Abraxane®/gemcitabine arm compared with 6.7 months in the gemcitabine arm. The progression-free survival (PFS) in the Abraxane®/gemcitabine arm was 5.5 months compared to the PFS of 3.7 months in the gemcitabine arm, showing a significant improvement. The study also showed that the 9- and 12-month PFS rates were doubled in the Abraxane®/gemcitabine arm and that the overall response rate by independent radiological review was tripled from 7% in the gemcitabine arm to 23% in the Abraxane®/gemcitabine arm. The results of this study were statistically and clinically persuasive, robust, consistent across subgroups, and supported by multiple endpoints. Moreover, the combination is especially effective in pancreatic cancer patients having a poor prognosis, for example but not limited to, patients having a late stage (e.g., stage IV) pancreatic cancer, patients having 3 or more (such as more than 3) metastatic sites, patients having metastasis in the liver, patients having metastasis in the lung, patients having a serum CA 19-9 level of ≥59×ULN (upper limit of normal), patients having a poor performance status (such as patients having a Karnofsky performance status (KPS) score of <90, for example 70-80), and/or patients wherein the primary location of the pancreatic cancer is the head of the pancreas.

The present invention thus provides methods, compositions, and kits for treatment of pancreatic cancer in various individuals by administration of a composition comprising nanoparticles comprising a taxane (such as paclitaxel) and a carrier protein in combination with gemcitabine.

DEFINITIONS

The term "individual" refers to a mammal, including humans. An individual includes, but is not limited to, human, bovine, horse, feline, canine, rodent, or primate. In some embodiments, the individual is human. The term "individual" also includes human patients described in the Examples.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of pancreatic cancer. The methods of the invention contemplate any one or more of these aspects of treatment.

The term "effective amount" used herein refers to an amount of a compound or composition sufficient to treat a specified disorder, condition or disease such as ameliorate, palliate, lessen, and/or delay one or more of its symptoms. In reference to pancreatic cancer, an effective amount comprises an amount sufficient to cause a tumor to shrink and/or to decrease the growth rate of the tumor (such as to suppress tumor growth) or to prevent or delay other unwanted cell proliferation in pancreatic cancer. In some embodiments, an effective amount is an amount sufficient to delay development of pancreatic cancer. In some embodiments, an effective amount is an amount sufficient to prevent or delay recurrence. An effective amount can be administered in one or more administrations. In the case of pancreatic cancer, the effective amount of the drug or composition may: (i) reduce the number of pancreatic cancer cells; (ii) reduce tumor size; (iii) inhibit, retard, slow to some extent and preferably stop pancreatic cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; (vii) relieve to some extent one or more of the symptoms associated with pancreatic cancer; and/or (viii) disrupt (such as destroy) pancreatic cancer stroma.

As used herein, by "combination therapy" is meant that a first agent be administered in conjunction with another agent. "In conjunction with" refers to administration of one treatment modality in addition to another treatment modality, such as administration of a nanoparticle composition described herein in addition to administration of the other agent to the same individual. As such, "in conjunction with" refers to administration of one treatment modality before, during, or after delivery of the other treatment modality to the individual.

As used herein, by "pharmaceutically acceptable" or "pharmacologically compatible" is meant a material that is not biologically or otherwise undesirable, e.g., the material may be incorporated into a pharmaceutical composition administered to an individual or patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

As used herein and in the appended claims, the singular forms "a," "an," and "the" include plural reference unless the context clearly indicates otherwise.

Reference to "about" a value or parameter herein includes (and describes) embodiments that are directed to that value or parameter per se. For example, description referring to "about X" includes description of "X."

It is understood that aspect and variations of the invention described herein include "consisting" and/or "consisting essentially of" aspects and variations.

Methods of Treating Pancreatic Cancer

The resent invention provides methods for treatment of pancreatic cancer (e.g., metastatic pancreatic cancer or locally advanced unresectable pancreatic cancer) in an individual (e.g., human) using a composition comprising nanoparticles comprising a taxane (such as paclitaxel) and a carrier protein in combination with gemcitabine.

In some embodiments, there is provided a method of treating pancreatic cancer in an individual comprising administering to the individual (i) an effective amount of a composition comprising nanoparticles comprising a taxane (such as paclitaxel) and a carrier protein; and (ii) an effective amount of gemcitabine. In some embodiments, the pancreatic cancer is pancreatic adenocarcinoma. In some embodiments, the pancreatic cancer is islet cell tumor. In some embodiments, the pancreatic cancer is pancreas endocrine tumor. In some embodiments, the pancreatic cancer is pancreatic neuroendocrine tumor. In some embodiments, the pancreatic cancer is ductal adenocarcinoma. In some embodiments, the pancreatic cancer is exocrine pancreas cancer.

In some embodiments, the pancreatic cancer to be treated is stage 0, stage I, stage II, stage III, or stage IV. In some embodiments, the pancreatic cancer to be treated is stage 0, stage IA, stage IB, stage IIA, stage IIB, stage III, or stage IV. In some embodiments, the pancreatic cancer is metastatic pancreatic cancer. In some embodiments, the pancreatic cancer is at stage M0. In some embodiments, the pancreatic cancer is at stage M1. In some embodiments, the individual has distant metastasis. In some embodiments, the individual does not have distant metastasis. In some embodiments, the individual had pancreatic cancer of any one of stage I, II, III or IV at the time of diagnosis of pancreatic cancer. By way of example, staging of pancreatic cancer may be based on a method known to one skilled in the art. Staging of pancreatic cancer may be according to the criteria set forth in American Joint Committee on Cancer (AJCC) Pancreas Cancer Staging, 7th edition (available at: http://www.cancerstaging.org/staging/posters/pancreas12×15.pdf, last accessed on Dec. 20, 2012). For example, the staging of pancreatic cancer may be according to the criteria set forth in Tables 1 and 2.

TABLE 1

Pancreas Cancer Staging Definitions*

Primary Tumor (T)

| | |
|---|---|
| TX | Primary tumor cannot be assessed |
| T0 | No evidence of primary tumor |
| Tis | Carcinoma in situ1** |
| T1 | Tumor limited to the pancreas, 2 cm or less in greatest dimension |
| T2 | Tumor limited to the pancreas, more than 2 cm in greatest dimension |
| T3 | Tumor extends beyond the pancreas but without involvement of the celiac axis or the superior mesenteric artery |
| T4 | Tumor involves the celiac axis or the superior mesenteric artery (unresectable primary tumor) |

Regional Lymph Nodes (N)

| | |
|---|---|
| NX | Regional lymph nodes cannot be assessed |
| N0 | No regional lymph node metastasis |
| N1 | Regional lymph node metastasis |

Distant Metastasis (M)

| | |
|---|---|
| M0 | No distant metastasis |
| M1 | Distant metastasis |

*Endocrine and exocrine tumors are staged by a single pancreatic staging system.
**Also includes the "PanInIII" classification.

TABLE 2

Anatomic Stage/Prognostic Groups

| | | | |
|---|---|---|---|
| Stage 0 | Tis | N0 | M0 |
| Stage IA | T1 | N0 | M0 |
| Stage IB | T2 | N0 | M0 |
| Stage IIA | T3 | N0 | M0 |
| Stage IIB | T1 | N1 | M0 |
| | T2 | N1 | M0 |
| | T3 | N1 | M0 |
| Stage III | T4 | Any N | M0 |
| Stage IV | Any T | Any N | M1 |

In some embodiments, the pancreatic cancer is early stage pancreatic cancer. In some embodiments, the pancreatic cancer is late stage pancreatic cancer. In some embodiments, the pancreatic cancer is advanced pancreatic cancer. In some embodiments, the pancreatic cancer is locally advanced pancreatic cancer. In some embodiments, the pancreatic cancer is recurrent pancreatic cancer. In some embodiments, the pancreatic cancer is non-metastatic pancreatic cancer. In some embodiments, the pancreatic cancer is metastatic pancreatic cancer. In some embodiments, the pancreatic cancer is a primary pancreatic cancer. In some embodiments, the primary pancreatic tumor has metastasized. In some embodiments, the pancreatic cancer has reoccurred after remission. In some embodiments, the pancreatic cancer is progressive pancreatic cancer. In some embodiments, the pancreatic cancer is pancreatic cancer in remission. In some embodiments, the individual has measurable disease (for example, according to RECIST criteria). In some embodiments, the individual has one or more metastatic tumors measurable, for example, by CT scan (or MRI). In some embodiments, the pancreatic cancer is metastatic pancreatic cancer. In some embodiments, the pancreatic cancer is stage IV pancreatic cancer. In some embodiments, the pancreatic cancer is locally advanced unresectable pancreatic cancer. In some embodiments, the pancreatic cancer is a resectable pancreatic cancer. In some embodiments, the pancreatic cancer is borderline resectable. In some embodiments, the pancreatic cancer is node-positive. In some embodiments, the pancreatic cancer is resected.

In some embodiments, the individual is human. In some embodiments, the individual is a male. In some embodiments, the individual is a female. In some embodiments, the individual is at least about any of 25, 30, 35, 40, 45, 50, 55, 60, 65, 70, 75, 80, 85, or 90 years old. In some embodiments, the individual is under about any of 25, 30, 35, 40, 45, 50, 55, 60, 65, 70, 75, 80, 85, or 90 years old. In some embodiments, the individual has one or more of the characteristics of the patients described in the examples of the present disclosure. For example, the individual may have at least one (e.g., at least any of 2, 3, 4, 5, 6, or 7) of the following characteristics: (1) histologically or cytologically confirmed metastatic adenocarcinoma of the pancreas; (2) one or more metastatic tumors measurable by CT scan (or MRI); (3) no previous radiotherapy, surgery, chemotherapy or investigational therapy for the treatment of metastatic disease; (4) male or non-pregnant and non-lactating female (≥18 years of age); (5) Karnofsky performance status (KPS) ≥70; (6) asymptomatic for jaundice; (7) no brain metastases; (8) no islet cell neoplasms; and (9) no interstitial lung disease.

In some embodiments, there is provided a method of treating metastatic pancreatic cancer (such as metastatic adenocarcinoma of the pancreas) in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine. In some embodiments, there is provided a method of treating metastatic pancreatic cancer in a human individual comprising administering to the individual (i) an effective amount of Nab-paclitaxel (for example about 5 mg/ml Nab-paclitaxel); and (ii) an effective amount of gemcitabine. The individual may be selected based on the metastatic status of the individual. For example, the individual to be treated in some embodiments may have 1 or more (such as at least any one 1, 2, 3, 4, 5, 6, 7, 8, 9, or 10) metastatic sites. In some embodiments, the individual has 3 or more metastatic sites. In some embodiments, the individual has more than 3 metastatic sites. In some embodiments, the individual has metastasis in the liver. In some embodiments, the individual has metastasis in the lung. In some embodiments, the individual has pulmonary metastasis. In some embodiments, the individual has peritoneal carcinomatosis. In some embodiments, the individual does not have brain metastasis. In some embodiments, the individual has brain metastasis.

Thus, for example, in some embodiments, there is provided a method of treating metastatic pancreatic cancer (such as metastatic adenocarcinoma of the pancreas) in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the individual has at least about 3 (e.g., more than 3) metastatic sites. In some embodiments, there is provided a method of treating metastatic pancreatic cancer (such as metastatic adenocarcinoma of the pancreas) in a human individual comprising administering to the individual (i) an effective amount of Nab-paclitaxel (for example about 5 mg/ml Nab-paclitaxel); and (ii) an effective amount of gemcitabine, wherein the individual has at least about 3 (e.g., more than 3) metastatic sites. In some embodiments, the pancreatic cancer is pancreatic adenocarcinoma. In some embodiments, the individual has measurable disease. In some embodiments, the individual is a female. In some embodiments, the individual is a male. In some embodiments, the individual is under about 65 (or 70, 75) years old. In some embodiments, the individual is at least about 65 (or 70, or 75) years old. In some embodiments, the primary location of the pancreatic cancer is the head of the pancreas. In some embodiments, the individual has a biliary stent. In some embodiments, the individual has previously received a Whipple procedure. In some embodiments, the individual has metastasis in the liver. In some embodiments, the individual has pulmonary metastasis. In some embodiments, the individual has peritoneal carcinomatosis. In some embodiments, the individual has serum CA19-9 level that is within ULN. In some embodiments, the individual has serum CA19-9 level that is between ULN and <59×ULN. In some embodiments, the individual has serum CA19-9 level that is ≥59×ULN. In some embodiments, the individual is human. In some embodiments, the taxane is paclitaxel. In some embodiments, the carrier protein is an albumin (such as human albumin or human serum albumin) In some embodiments, the treatment is first line treatment. In some embodiments, the individual has hENT1 overexpression (for example based on immunohistochemistry evaluation). In some embodiments, the individual has decreased (low) hENT1 expression (for example based on immunohistochemistry evaluation).

In some embodiments, there is provided a method of treating stage IV pancreatic cancer in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine. In some embodiments, there is provided a method of treating stage IV pancreatic cancer in a human individual comprising administering to the individual (i) an effective amount of Nab-paclitaxel (for example about 5 mg/ml Nab-paclitaxel); and (ii) an effective amount of gemcitabine. In some embodiments, the pancreatic cancer is pancreatic adenocarcinoma. In some embodiments, the individual has measurable disease. In some embodiments, the individual is a female. In some embodiments, the individual is a male. In some embodiments, the individual is under about 65 (or 70, 75) years old. In some embodiments, the individual is at least about 65 (or 70, or 75) years old. In some embodiments, the individual has at least about 3 (e.g., more than 3) metastatic sites. In some embodiments, the primary location of the pancreatic cancer is the head of the pancreas. In some embodiments, the individual has a biliary stent. In some embodiments, the individual has previously received a Whipple procedure. In some embodiments, the individual has metastasis in the liver. In some embodiments, the individual has pulmonary metastasis. In some embodiments, the individual has peritoneal carcinomatosis. In some embodiments, the individual has serum CA19-9 level that is within ULN. In some embodiments, the individual has serum CA19-9 level that is between ULN and <59×ULN. In some embodiments, the individual has serum CA19-9 level that is ≥59×ULN. In some embodiments, the individual is human. In some embodiments, the taxane is paclitaxel. In some embodiments, the carrier protein is an albumin (such as human albumin or human serum albumin) In some embodiments, the treatment is first line treatment. In some embodiments, the individual has hENT1 overexpression (for example a high level based on immunohistochemistry evaluation). In some embodiments, the individual has decreased (low) hENT1 expression (for example a low level based on immunohistochemistry evaluation).

In some embodiments, there is provided a method of treating locally advanced unresectable pancreatic cancer in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine. In some embodiments, there is provided a method of treating locally advanced unresectable pancreatic cancer in a human individual comprising administering to the individual (i) an effective amount of Nab-paclitaxel (for example about 5 mg/ml Nab-paclitaxel); and (ii) an effective amount of gemcitabine. In some embodiments, the pancreatic cancer is pancreatic adenocarcinoma. In some embodiments, the individual has measurable disease. In some embodiments, the individual is a female. In some embodiments, the individual is a male. In some embodiments, the individual is under about 65 (or 70, 75) years old. In some embodiments, the individual is at least about 65 (or 70, or 75) years old. In some embodiments, the individual has at least about 3 (e.g., more than 3) metastatic sites. In some embodiments, the primary location of the pancreatic cancer is the head of the pancreas. In some embodiments, the individual has a biliary stent. In some embodiments, the individual has previously received a Whipple procedure. In some embodiments, the individual has metastasis in the liver. In some embodiments, the individual has pulmonary metastasis. In some embodiments, the individual has peritoneal carcinomatosis. In some embodiments, the individual has serum CA19-9 level that is within ULN. In some embodiments, the individual has serum CA19-9 level that is between ULN and <59×ULN. In some embodiments, the individual has serum CA19-9 level that is ≥59×ULN. In some embodiments, the individual is human. In some embodiments, the taxane is paclitaxel. In some embodiments, the carrier protein is an albumin (such as human albumin or human serum albumin) In some embodiments, the treatment is first line treatment. In some embodiments, the individual has hENT1 overexpression (for example a high level based on immunohistochemistry evaluation). In some embodiments, the individual has decreased (low) hENT1 expression (for example a low level based on immunohistochemistry evaluation).

In some embodiments, the primary location of the pancreatic cancer is the head, body, tail, or neck of the pancreas. In some embodiments, the primary lesion of the pancreatic cancer is in the head, body, tail, or neck of the pancreas. In some embodiments, the primary location of the pancreatic cancer is the head of the pancreas. In some embodiments, the primary lesion of the pancreatic cancer is not in the head of the pancreas. For example, in some embodiments, there is provided a method of treating pancreatic cancer (such as metastatic pancreatic cancer or locally advanced unresectable pancreatic cancer) in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the primary location of the pancreatic cancer is in the head of the pancreas. In some embodiments, the pancreatic cancer is adenocarcinoma of the pancreas. In some embodiments, there is provided a method of treating pancreatic cancer (such as metastatic or locally advanced unresectable pancreatic cancer) in a human individual comprising administering to the individual (i) an effective amount of Nab-paclitaxel (for example about 5 mg/ml Nab-paclitaxel); and (ii) an effective amount of gemcitabine, wherein the primary location of the pancreatic cancer is in the head of the pancreas. In some embodiments, the pancreatic cancer is pancreatic adenocarcinoma. In some embodiments, the individual has measurable disease. In some embodiments, the individual is a female. In some embodiments, the individual is a male. In some embodiments, the individual is under about 65 (or 70, 75) years old. In some embodiments, the individual is at least about 65 (or 70, or 75) years old. In some embodiments, the individual has at least about 3 (e.g., more than 3) metastatic sites. In some embodiments, the individual has a biliary stent. In some embodiments, the individual has previously received a Whipple procedure. In some embodiments, the individual has metastasis in the liver. In some embodiments, the individual has pulmonary metastasis. In some embodiments, the individual has peritoneal carcinomatosis. In some embodiments, the individual has serum CA19-9 level that is within ULN. In some embodiments, the individual has serum CA19-9 level that is between ULN and <59×ULN. In some embodiments, the individual has serum CA19-9 level that is ≥59×ULN. In some embodiments, the individual is human. In some embodiments, the taxane is paclitaxel. In some embodiments, the carrier protein is an albumin (such as human albumin or human serum albumin) In some embodiments, the treatment is first line treatment. In some embodiments, the individual has hENT1 overexpression (for example based on immunohistochemistry evaluation). In some embodiments, the individual has decreased (low) hENT1 expression (for example based on immunohistochemistry evaluation).

In some embodiments, the individual has metastasis in the liver. For example, in some embodiments, there is provided a method of treating metastatic pancreatic cancer (such as metastatic adenocarcinoma of the pancreas) in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the individual has metastasis in the liver. In some embodiments, there is provided a method of treating metastatic pancreatic cancer (such as metastatic adenocarcinoma of the pancreas) in a human individual comprising administering to the individual (i) an effective amount of Nab-paclitaxel (for example about 5 mg/ml Nab-paclitaxel); and (ii) an effective amount of gemcitabine, wherein the individual has metastasis in the liver. In some embodiments, the pancreatic cancer is pancreatic adenocarcinoma. In some embodiments, the individual has measurable disease. In some embodiments, the individual is a female. In some embodiments, the individual is a male. In some embodiments, the individual is under about 65 (or 70, 75) years old. In some embodiments, the individual is at least about 65 (or 70, or 75) years old. In some embodiments, the individual has at least about 3 (e.g., more than 3) metastatic sites. In some embodiments, the primary location of the pancreatic cancer is in the head of the pancreas. In some embodiments, the individual has a biliary stent. In some embodiments, the individual has previously received a Whipple procedure. In some embodiments, the individual has pulmonary metastasis. In some embodiments, the individual has peritoneal carcinomatosis. In some embodiments, the individual has serum CA19-9 level that is within ULN. In some embodiments, the individual has serum CA19-9 level that is between ULN and <59×ULN. In some embodiments, the individual has serum CA19-9 level that is ≥59×ULN. In some embodiments, the individual is human. In some embodiments, the taxane is paclitaxel. In some embodiments, the carrier protein is an albumin (such as human albumin or human serum albumin) In some embodiments, the treatment is first line treatment. In some embodiments, the individual has hENT1 overexpression (for example based on immunohistochemistry evaluation). In some embodiments, the individual has decreased (low) hENT1 expression (for example based on immunohistochemistry evaluation).

In some embodiments, the individual has serum CA19-9 level of at least about any of 10× upper limit of normal ("ULN"), 20×ULN, 30×ULN, 40×ULN, 50×ULN, 55×ULN, 59×ULN, 60×ULN, 70×ULN, 80×ULN, 90×ULN, 100×ULN, 110×ULN, 120×ULN, 130×ULN, 140×ULN, or 150×ULN. In some embodiments, the individual has serum CA19-9 level of lower than about any of 10×ULN, 20×ULN, 30×ULN, 40×ULN, 50×ULN, 55×ULN, 59×ULN, 60×ULN, 70×ULN, 80×ULN, 90×ULN, 100×ULN, 110×ULN, 120×ULN, 130×ULN, 140×ULN, or 150×ULN. In some embodiments, the individual has serum CA19-9 level of about any of 10×ULN, 20×ULN, 30×ULN, 40×ULN, 50×ULN, 55×ULN, 59×ULN, 60×ULN, 70×ULN, 80×ULN, 90×ULN, 100× ULN, 110×ULN, 120×ULN, 130×ULN, 140×ULN, or 150× ULN. In some embodiments, the individual has serum CA19-9 level of about any of 1×ULN-10×ULN, 1×ULN-20×ULN, 1×ULN-30×ULN, 1×ULN-40×ULN, 1×ULN-50×ULN, 1×ULN-55×ULN, 1×ULN-59×ULN, 1×ULN-60×ULN, 1×ULN-70×ULN, 1×ULN-80×ULN, >1×ULN-59×ULN, 10×ULN-20×ULN, 20×ULN-30×ULN, 30×ULN-40×ULN, 40×ULN-50×ULN, 50×ULN-59×ULN, 50×ULN-60×ULN, 60×ULN-70×ULN, 70×ULN-80×ULN, 90×ULN-100×ULN, 100×ULN 120×ULN, 120×ULN-150×ULN, or 150×ULN-200×ULN. In some embodiments, the individual has serum CA19-9 level that is within ULN. In some embodiments, the individual has serum CA19-9 level that is about or below ULN. In some embodiments, the individual has serum CA19-9 level that is not greater than about ULN. In some embodiments, the individual has serum CA19-9 level that is between about ULN and smaller than about 59×ULN. In some embodiments, the individual has serum CA19-9 level that is no less than (such as greater than) about 59×ULN.

Thus, for example, in some embodiments, there is provided a method of treating pancreatic cancer (such as metastatic or locally advanced unresectable pancreatic cancer) in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the individual has serum CA19-9 level that is ≥59×ULN. In some embodiments, there is provided a method of treating pancreatic cancer (such as metastatic or locally advanced unresectable pancreatic cancer) in a human individual comprising administering to the individual (i) an effective amount of Nab-paclitaxel (for example about 5 mg/ml Nab-paclitaxel); and (ii) an effective amount of gemcitabine, wherein the individual has serum CA19-9 level that is ≥59×ULN. In some embodiments, the pancreatic cancer is pancreatic adenocarcinoma. In some embodiments, the individual has measurable disease. In some embodiments, the individual is a female. In some embodiments, the individual is a male. In some embodiments, the individual is under about 65 (or 70, 75) years old. In some embodiments, the individual is at least about 65 (or 70, or 75) years old. In some embodiments, the individual has at least about 3 (e.g., more than 3) metastatic sites. In some embodiments, the primary location of the pancreatic cancer is in the head of the pancreas. In some embodiments, the individual has a biliary stent. In some embodiments, the individual has previously received a Whipple procedure. In some embodiments, the individual has metastasis in the liver. In some embodiments, the individual has pulmonary metastasis. In some embodiments, the individual has peritoneal carcinomatosis. In some embodiments, the individual is human. In some embodiments, the taxane is paclitaxel. In some embodiments, the carrier protein is an albumin (such as human albumin or human serum albumin) In some embodiments, the treatment is first line treatment. In some embodiments, the individual has hENT1 overexpression (for example based on immunohistochemistry evaluation). In some embodiments, the individual has decreased (low) hENT1 expression (for example based on immunohistochemistry evaluation). In some embodiments, the metastatic pancreatic cancer is metastatic adenocarcinoma of the pancreas.

In some embodiments, the individual has Karnofsky Performance Status (KPS) score of about any of 10, 20, 30, 40, 50, 60, 70, 80, 90, or 100. In some embodiments, the individual has KPS score of greater than about any of 10, 20, 30, 40, 50, 60, 70, 80, 90, or 99. In some embodiments, the individual has KPS score of no greater than about any of 10, 20, 30, 40, 50, 60, 70, 80, 90, or 100. In some embodiments, the individual has KPS score of about any of 10-20, 20-30, 30-40, 40-50, 50-60, 60-70, 70-80, 80-90, or 90-100.

Thus, for example, in some embodiments, there is provided a method of treating pancreatic cancer (such as metastatic or locally advanced unresectable pancreatic cancer) in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the individual has KPS score of less than about 90 (for example about 70-80). In some embodiments, there is provided a method of treating pancreatic cancer (such as metastatic or locally advanced unresectable pancreatic cancer) in a human individual comprising administering to the individual (i) an effective amount of Nab-paclitaxel (for example about 5 mg/ml Nab-paclitaxel); and (ii) an effective amount of gemcitabine, wherein the individual has KPS score of less than about 90 (for example about 70-80). In some embodiments, the pancreatic cancer is pancreatic adenocarcinoma. In some embodiments, the individual has measurable disease. In some embodiments, the individual is a female. In some embodiments, the individual is a male. In some embodiments, the individual is under about 65 (or 70, 75) years old. In some embodiments, the individual is at least about 65 (or 70, or 75) years old. In some embodiments, the individual has at least about 3 (e.g., more than 3) metastatic sites. In some embodiments, the primary location of the pancreatic cancer is in the head of the pancreas. In some embodiments, the individual has a biliary stent. In some embodiments, the individual has previously received a Whipple procedure. In some embodiments, the individual has metastasis in the liver. In some embodiments, the individual has pulmonary metastasis. In some embodiments, the individual has peritoneal carcinomatosis. In some embodiments, the individual has serum CA19-9 level that is within ULN. In some embodiments, the individual has serum CA19-9 level that is between ULN and <59×ULN. In some embodiments, the individual has serum CA19-9 level that is ≥59×ULN. In some embodiments, the individual is human. In some embodiments, the taxane is paclitaxel. In some embodiments, the carrier protein is an albumin (such as human albumin or human serum albumin) In some embodiments, the treatment is first line treatment. In some embodiments, the individual has hENT1 overexpression (for example based on immunohistochemistry evaluation). In some embodiments, the individual has decreased (low) hENT1 expression (for example based on immunohistochemistry evaluation). In some embodiments, the metastatic pancreatic cancer is metastatic adenocarcinoma of the pancreas.

Any individual having pancreatic cancer (e.g., metastatic pancreatic cancer) may be treated using a method described herein. In some embodiments, the individual is chemotherapy-naïve or has not been treated with chemotherapy. In some embodiments, the individual has not been previously treated for the pancreatic cancer. In some embodiments, the individual has not been previously treated for the metastatic pancreatic cancer (such as metastatic adenocarcinoma of the pancreas). In some embodiments, the individual has not received prior therapy or prior chemotherapy (such as prior cytotoxic chemotherapy) for the pancreatic cancer (e.g., the metastatic pancreatic cancer). In some embodiments, the individual has not received radiotherapy or surgery for the pancreatic cancer (e.g., the metastatic pancreatic cancer). In some embodiments, the individual has not received prior adjuvant therapy (e.g., adjuvant cytotoxic chemotherapy). In some embodiments, the individual has previously been treated with 5-FU as a radiation sensitizer in the adjuvant setting (e.g., at least about 6 months prior to the start of a treatment method described herein). In some embodiments, the individual has previously been treated with gemcitabine as a radiation sensitizer in the adjuvant setting (e.g., at least about 6 months prior to the start of a treatment method described herein).

The methods provided herein may be practiced in an adjuvant setting. Adjuvant setting may refer to a clinical setting in which an individual has had a history of a cancer described herein, and generally (but not necessarily) been responsive to therapy, which includes, but is not limited to, surgery (e.g., surgery resection), radiotherapy, and chemotherapy; however, because of their history of cancer, these individuals are considered at risk of development of the disease. Treatment or administration in the adjuvant setting refers to a subsequent mode of treatment. The degree of risk (e.g., when an individual in the adjuvant setting is considered as "high risk" or "low risk") depends upon several factors, most usually the extent of disease when first treated.

In some embodiments, the method is practiced in a neoadjuvant setting, i.e., the method may be carried out before the primary/definitive therapy. In some embodiments, the method is used to treat an individual who has previously been treated. Any of the methods of treatment provided herein may be used to treat an individual who has not previously been treated.

Methods described herein may be used to treat an individual having pancreatic cancer who has previously been treated for the pancreatic cancer. The prior treatment may include a chemotherapy agent such as gemcitabine (e.g., GEMZAR). In some embodiments, the prior treatment comprises gemcitabine and/or erlotinib. In some embodiments, the prior treatment comprises 5-FU. In some embodiments, the individual has been previously treated for the pancreatic cancer and the individual is substantially refractory to the prior treatment. In some embodiments, the individual has been previously treated for the pancreatic cancer and is no longer or only partially responsive to the prior treatment. In some embodiments, the individual is initially responsive to the prior treatment but has progressed on the prior treatment. In some embodiments, the individual is not responsive to the prior treatment.

Methods described herein may be used as a first line therapy. For example, in some embodiments, there is provided a method of treating metastatic, locally advanced unresectable, or stage IV pancreatic cancer in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the treatment is first line treatment. In some embodiments, there is provided a method of treating metastatic, locally advanced unresectable, or stage IV pancreatic cancer in a human individual comprising administering to the individual (i) an effective amount of Nab-paclitaxel (for example about 5 mg/ml Nab-paclitaxel); and (ii) an effective amount of gemcitabine, wherein the treatment is first line treatment.

Methods described herein may also be used as a second line or third line therapy after the prior treatment for pancreatic cancer has failed or has substantially failed, or the pancreatic cancer is substantially refractory to the first line therapy. In some embodiments, the individual has received at least one line of therapy (e.g., chemotherapy or immunotherapy) for treating pancreatic cancer (e.g., metastatic pancreatic cancer) prior to receiving the treatment described herein. In some embodiments, the patient has received 1 line of therapy or 2 lines of therapy (e.g., 1 line of chemotherapy or immunotherapy or 2 lines of chemotherapy or immunotherapy). Thus, the treatment described herein may be used as a second line therapy or a third line therapy. The prior line of therapy described herein may be a prior line of chemotherapy or immunotherapy. The first line of therapy may comprise any of the following: gemcitabine, 5-FU, and/or erlotinib.

In some embodiments, there is provided a method of treating metastatic, locally advanced unresectable, or stage IV pancreatic cancer in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the individual has serum CA19-9 level that is ≥59×ULN, and wherein the primary location of the pancreatic cancer is in the head of the pancreas. In some embodiments, there is provided a method of treating metastatic, locally advanced unresectable, or stage IV pancreatic cancer in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the individual has serum CA19-9 level that is ≥59×ULN, and wherein the individual has metastasis in the liver. In some embodiments, there is provided a method of treating metastatic, locally advanced unresectable, or stage IV pancreatic cancer in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the individual has serum CA19-9 level that is ≥59×ULN, and wherein the individual has 3 or more metastatic sites. In some embodiments, there is provided a method of treating metastatic, locally advanced unresectable, or stage IV pancreatic cancer in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the individual has serum CA19-9 level that is ≥59×ULN, wherein the individual has metastasis in the liver, and wherein the individual has 3 or more metastatic sites. In some embodiments, there is provided a method of treating metastatic, locally advanced unresectable, or stage IV pancreatic cancer in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the individual has serum CA19-9 level that is ≥59×ULN, wherein the individual has metastasis in the liver, and wherein the primary location of the pancreatic cancer is in the head of the pancreas. In some embodiments, there is provided a method of treating metastatic, locally advanced unresectable, or stage IV pancreatic cancer in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the individual has serum CA19-9 level that is ≥59×ULN, wherein the primary location of the pancreatic cancer is in the head of the pancreas, and wherein the individual has 3 or more metastatic sites. In some embodiments, there is provided a method of treating metastatic, locally advanced unresectable, or stage IV pancreatic cancer in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the individual has serum CA19-9 level that is ≥59×ULN, wherein the individual has metastasis in the liver, wherein the individual has 3 or more metastatic sites, and wherein the primary location of the pancreatic cancer is in the head of the pancreas. In some embodiments, the treatment is first line treatment. In some embodiments, the individual has hENT1 overexpression (for example based on immunohistochemistry evaluation). In some embodiments, the individual has decreased (low) hENT1 expression (for example based on immunohistochemistry evaluation).

In some embodiments, there is provided a method of treating metastatic, locally advanced unresectable, or stage IV pancreatic cancer in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the individual has metastasis in the liver, and wherein the primary location of the pancreatic cancer is in the head of the pancreas. In some embodiments, there is provided a method of treating metastatic, locally advanced unresectable, or stage IV pancreatic cancer in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the individual has 3 or more metastatic sites, and wherein the primary location of the pancreatic cancer is in the head of the pancreas. In some embodiments, there is provided a method of treating metastatic, locally advanced unresectable, or stage IV pancreatic cancer in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the individual has metastasis in the liver, and wherein the individual has 3 or more metastatic sites. In some embodiments, there is provided a method of treating metastatic, locally advanced unresectable, or stage IV pancreatic cancer in an individual comprising administering to the individual (i) an effective amount of a composition comprising nanoparticles comprising paclitaxel coated with an albumin (including nanoparticles having an average diameter of no greater than about 200 nm); and (ii) an effective amount of gemcitabine, wherein the individual has metastasis in the liver, wherein the individual has 3 or more metastatic sites, and wherein the primary location of the pancreatic cancer is in the head of the pancreas. In some embodiments, the treatment is first line treatment. In some embodiments, the individual has hENT1 overexpression (for example based on immunohistochemistry evaluation).

The methods described herein are useful for various aspects of pancreatic cancer treatment. In some embodiments, there is provided a method for treatment of pancreatic cancer in an individual (e.g., human) using an effective amount of a composition comprising nanoparticles comprising a taxane (such as paclitaxel) and a carrier protein in combination with gemcitabine. In some embodiments, an effective amount is an amount sufficient to delay development of pancreatic cancer. In some embodiments, an effective amount is an amount sufficient to prevent or delay occurrence and/or recurrence of pancreatic cancer. In some embodiments, an effective amount comprises an amount sufficient to produce a complete response when an individual is treated with any of the methods described herein for pancreatic cancer. In some embodiments, an effective amount comprises an amount sufficient to produce a partial response when an individual is treated with any of the methods described herein for pancreatic cancer.

In some embodiments, the effective amount of a composition comprising nanoparticles comprising taxane (e.g., paclitaxel) and a carrier protein (e.g., an albumin) produces a complete response, a partial response, reduction in size of a pancreatic tumor, reduction in metastasis, stable disease, and/or an increase in overall response rate. In some embodiments, the taxane is paclitaxel. In some embodiments, the carrier protein is an albumin. The efficacy parameters (such as complete response or partial response) described herein may be determined by any of the methods known to one skilled in the art. For example, the efficacy parameters may be determined according to RECIST such as RECIST version 1.0 or 1.1 criteria. RECIST version 1.1 criteria are described in Eisenhauer E A et al. 2009, Eur J Cancer., 45(2):228-47, the disclosure of which is incorporated herein by reference in its entirety.

In some embodiments, there is provided a method of inhibiting pancreatic cancer cell proliferation in an individual, comprising administering to the individual (i) an effective amount of a composition comprising nanoparticles comprising a taxane (e.g., paclitaxel) and a carrier protein (e.g., an albumin), and (b) an effective amount of gemcitabine. In some embodiments, the taxane is paclitaxel. In some embodiments, the carrier protein is an albumin (such as human albumin or human serum albumin) In some embodiments, there is provided a method of inhibiting pancreatic cancer cell proliferation in an individual, comprising administering to the individual an effective amount of a composition comprising nanoparticles comprising paclitaxel and an albumin. In some embodiments, at least about 10% (including for example at least about any of 20%, 30%, 40%, 60%, 70%, 80%, 90%, 91%, 92%, 93%, 94%, 95%, 96%, 97%, 98%, 99%, or 100%) cell proliferation is inhibited. In some embodiments, the individual has stage IV or metastatic pancreatic cancer (such as metastatic adenocarcinoma of the pancreas). In some embodiments, the pancreatic cancer is pancreatic adenocarcinoma. In some embodiments, the individual has measurable disease. In some embodiments, the individual is a female. In some embodiments, the individual is a male. In some embodiments, the individual is under about 65 (or 70, 75) years old. In some embodiments, the individual is at least about 65 (or 70, or 75) years old. In some embodiments, the individual has at least about 3 (e.g., more than 3) metastatic sites. In some embodiments, the primary location of the pancreatic cancer is the head of the pancreas. In some embodiments, the individual has a biliary stent. In some embodiments, the individual has previously received a Whipple procedure. In some embodiments, the individual has metastasis in the liver. In some embodiments, the individual has pulmonary metastasis. In some embodiments, the individual has peritoneal carcinomatosis. In some embodiments, the individual has serum CA19-9 level that is within ULN. In some embodiments, the individual has serum CA19-9 level that is between ULN and <59×ULN. In some embodiments, the individual has serum CA19-9 level that is ≥59×ULN. In some embodiments, the individual is human. In some embodiments, the treatment is first line treatment. In some embodiments, the individual has hENT1 overexpression (for example based on immunohistochemistry evaluation). In some embodiments, the individual has decreased (low) hENT1 expression (for example based on immunohistochemistry evaluation).

In some embodiments, there is provided a method of preventing or inhibiting metastasis of pancreatic cancer in an individual, comprising administering to the individual an effective amount of a composition comprising nanoparticles comprising a taxane (e.g., paclitaxel) and a carrier protein (e.g., an albumin) in combination with an effective amount of gemcitabine. In some embodiments, the taxane is paclitaxel. In some embodiments, the carrier protein is an albumin (such as human albumin or human serum albumin). In some embodiments, there is provided a method of preventing or inhibiting metastasis of pancreatic cancer in an individual, comprising administering to the individual an effective amount of a composition comprising nanoparticles comprising paclitaxel and an albumin. In some embodiments, at least about 10% (including for example at least about any of 20%, 30%, 40%, 60%, 70%, 80%, 90%, 95%, or 100%) metastasis is inhibited. In some embodiments, there is provided a method of delaying or slowing metastasis of pancreatic cancer in an individual, comprising administering to the individual an effective amount of a composition comprising nanoparticles comprising a taxane and a carrier protein (e.g., an albumin) In some embodiments, the individual has stage IV or metastatic pancreatic cancer (such as metastatic adenocarcinoma of the pancreas). In some embodiments, the pancreatic cancer is pancreatic adenocarcinoma. In some embodiments, the individual has measurable disease. In some embodiments, the individual is a female. In some embodiments, the individual is a male. In some embodiments, the individual is under about 65 (or 70, 75) years old. In some embodiments, the individual is at least about 65 (or 70, or 75) years old. In some embodiments, the individual has at least about 3 (e.g., more than 3) metastatic sites. In some embodiments, the primary location of the pancreatic cancer is the head of the pancreas. In some embodiments, the individual has a biliary stent. In some embodiments, the individual has previously received a Whipple procedure. In some embodiments, the individual has metastasis in the liver. In some embodiments, the individual has pulmonary metastasis. In some embodiments, the individual has peritoneal carcinomatosis. In some embodiments, the individual has serum CA19-9 level that is within ULN. In some embodiments, the individual has serum CA19-9 level that is between ULN and <59×ULN. In some embodiments, the individual has serum CA19-9 level that is ≥59×ULN. In some embodiments, the treatment is first line treatment. In some embodiments, the individual has hENT1 overexpression (for example based on immunohistochemistry evaluation). In some embodiments, the individual has decreased (low) hENT1 expression (for example based on immunohistochemistry evaluation).

In some embodiments, there is provided a method of reducing size of a pancreatic tumor or reducing pancreatic tumor volume in an individual, comprising administering to the individual an effective amount of a composition comprising nanoparticles comprising a taxane (e.g., paclitaxel) and a carrier protein (e.g., an albumin such as human albumin or human serum albumin) in combination with an effective amount of gemcitabine. In some embodiments, at least about any of 10%, 20%, 30%, 40%, 50%, 60%, 70%, 80%, 90%, or 95% of the tumor size or tumor volume is reduced. In some embodiments, the individual has stage IV, locally advanced unresectable, or metastatic pancreatic cancer (such as metastatic adenocarcinoma of the pancreas). In some embodiments, the pancreatic cancer is pancreatic adenocarcinoma. In some embodiments, the individual has measurable disease. In some embodiments, the individual is a female. In some embodiments, the individual is a male. In some embodiments, the individual is under about 65 (or 70, 75) years old. In some embodiments, the individual is at least about 65 (or 70, or 75) years old. In some embodiments, the individual has at least about 3 (e.g., more than 3) metastatic sites. In some embodiments, the primary location of the pancreatic cancer is the head of the pancreas. In some embodiments, the individual has a biliary stent. In some embodiments, the individual has previously received a Whipple procedure. In some embodiments, the individual has metastasis in the liver. In some embodiments, the individual has pulmonary metastasis. In some embodiments, the individual has peritoneal carcinomatosis. In some embodiments, the individual has serum CA19-9 level that is within ULN. In some embodiments, the individual has serum CA19-9 level that is between ULN and <59×ULN. In some embodiments, the individual has serum CA19-9 level that is ≥59×ULN. In some embodiments, the individual is human. In some embodiments, the taxane is paclitaxel. In some embodiments, the carrier protein is an albumin (such as human albumin or human serum albumin) In some embodiments, the treatment is first line treatment. In some embodiments, the individual has hENT1 overexpression (for example based on immunohistochemistry evaluation). In some embodiments, the individual has low (decreased) hENT expression (for example based on immunohistochemistry evaluation).

In some embodiments, there is provided a method of prolonging time to disease progression of pancreatic cancer in an individual, comprising administering to the individual an effective amount of a composition comprising nanoparticles comprising a taxane (e.g., paclitaxel) and a carrier protein (e.g., an albumin) in combination with an effective amount of gemcitabine. In some embodiments, the taxane is paclitaxel. In some embodiments, the carrier protein is an albumin (such as human albumin or human serum albumin). In some embodiments, there is provided a method of prolonging time to disease progression of pancreatic cancer in an individual, comprising administering to the individual an effective amount of a composition comprising nanoparticles comprising paclitaxel and an albumin in combination with an effective amount of gemcitabine. In some embodiments, the method prolongs the time to disease progression by at least about any of 1, 2, 3, 4, 5, 6, 7, 8, 9, 10, 11, 12, 13, 14, 15, 16, 17, 18, 19, 20, 2, 24, 26, 28, 30, 35, 40, 45, or 50 weeks. In some embodiments, the individual has stage IV, locally advanced unresectable, or metastatic pancreatic cancer (such as metastatic adenocarcinoma of the pancreas). In some embodiments, the individual has stage IV or metastatic pancreatic cancer (such as metastatic adenocarcinoma of the pancreas). In some embodiments, the pancreatic cancer is pancreatic adenocarcinoma. In some embodiments, the individual has measurable disease. In some embodiments, the individual is a female. In some embodiments, the individual is a male. In some embodiments, the individual is under about 65 (or 70, 75) years old. In some embodiments, the individual is at least about 65 (or 70, or 75) years old. In some embodiments, the individual has at least about 3 (e.g., more than 3) metastatic sites. In some embodiments, the primary location of the pancreatic cancer is the head of the pancreas. In some embodiments, the individual has a biliary stent. In some embodiments, the individual has previously received a Whipple procedure. In some embodiments, the individual has metastasis in the liver. In some embodiments, the individual has pulmonary metastasis. In some embodiments, the individual has peritoneal carcinomatosis. In some embodiments, the individual has serum CA19-9 level that is within ULN. In some embodiments, the individual has serum CA19-9 level that is between ULN and <59×ULN. In some embodiments, the individual has serum CA19-9 level that is ≥59×ULN. In some embodiments, the treatment is first line treatment. In some embodiments, the individual has hENT1 overexpression (for example based on immunohistochemistry evaluation). In some embodiments, the individual has decreased (low) hENT1 expression (for example based on immunohistochemistry evaluation).

In some embodiments, there is provided a method of prolonging survival of an individual having pancreatic cancer, comprising administering to the individual an effective amount of a composition comprising nanoparticles comprising a taxane (e.g., paclitaxel) and a carrier protein (e.g., an albumin) in combination with an effective amount of gemcitabine. In some embodiments, the taxane is paclitaxel. In some embodiments, the carrier protein is an albumin (such as human albumin or human serum albumin) In some embodiments, there is provided a method of prolonging survival of an individual having pancreatic cancer, comprising administering to the individual an effective amount of a composition comprising nanoparticles comprising a paclitaxel and an albumin in combination with an effective amount of gemcitabine. In some embodiments, the method prolongs the survival of the individual by at least about any of 1, 2, 3, 4, 5, 6, 7, 8, 9, 10, 11, 12, 18, or 24 months. In some embodiments, the individual has stage IV, locally advanced unresectable, or metastatic pancreatic cancer (such as metastatic adenocarcinoma of the pancreas). In some embodiments, the individual has stage IV or metastatic pancreatic cancer (such as metastatic adenocarcinoma of the pancreas). In some embodiments, the pancreatic cancer is pancreatic adenocarcinoma. In some embodiments, the individual has measurable disease. In some embodiments, the individual is a female. In some embodiments, the individual is a male. In some embodiments, the individual is under about 65 (or 70, 75) years old. In some embodiments, the individual is at least about 65 (or 70, or 75) years old. In some embodiments, the individual has at least about 3 (e.g., more than 3) metastatic sites. In some embodiments, the primary location of the pancreatic cancer is the head of the pancreas. In some embodiments, the individual has a biliary stent. In some embodiments, the individual has previously received a Whipple procedure. In some embodiments, the individual has metastasis in the liver. In some embodiments, the individual has pulmonary metastasis. In some embodiments, the individual has peritoneal carcinomatosis. In some embodiments, the individual has serum CA19-9 level that is within ULN. In some embodiments, the individual has serum CA19-9 level that is between ULN and <59×ULN. In some embodiments, the individual has serum CA19-9 level that is ≥59×ULN. In some embodiments, the individual is human. In some embodiments, the treatment is first line treatment. In some embodiments, the individual has hENT1 overexpression (for example based on immunohistochemistry evaluation). In some embodiments, the individual has decreased (low) hENT1 expression (for example based on immunohistochemistry evaluation).

In some embodiments, levels of serum CA 19-9 in the individual treated with a method described herein decrease significantly. In some embodiments, there is provided a method of treating pancreatic cancer in an individual, comprising administering to the individual an effective amount of a composition comprising nanoparticles comprising a taxane (e.g., paclitaxel) and a carrier protein (e.g., an albumin) in combination with an effective amount of gemcitabine, wherein the levels of serum CA 19-9 in the individual are decreased by at least about 20% (including for example at least about any of 20%, 30%, 40%, 50%, 52%, 53%, 55%, 57%, 59%, 60%, 70%, 80%, 90%, 95%, or 100%) in comparison to the levels of serum CA 19-9 prior to the treatment. In some embodiments, the levels of serum CA 19-9 in the individual administered with the composition comprising nanoparticles comprising a taxane (such as paclitaxel) and an albumin in combination with gemcitabine are decreased by at least about 50% in comparison to the levels of serum CA 19-9 prior to the treatment. In some embodiments, the individual has stage IV, locally advanced unresectable, or metastatic pancreatic cancer (such as metastatic adenocarcinoma of the pancreas). In some embodiments, the individual has stage IV, locally advanced unresectable, or metastatic pancreatic cancer (such as metastatic adenocarcinoma of the pancreas). In some embodiments, the pancreatic cancer is pancreatic adenocarcinoma. In some embodiments, the individual has measurable disease. In some embodiments, the individual is a female. In some embodiments, the individual is a male. In some embodiments, the individual is under about 65 (or 70, 75) years old. In some embodiments, the individual is at least about 65 (or 70, or 75) years old. In some embodiments, the individual has at least about 3 (e.g., more than 3) metastatic sites. In some embodiments, the primary location of the pancreatic cancer is the head of the pancreas. In some embodiments, the individual has a biliary stent. In some embodiments, the individual has previously received a Whipple procedure. In some embodiments, the individual has metastasis in the liver. In some embodiments, the individual has pulmonary metastasis. In some embodiments, the individual has peritoneal carcinomatosis. In some embodiments, the individual has serum CA19-9 level that is within ULN. In some embodiments, the individual has serum CA19-9 level that is between ULN and <59×ULN. In some embodiments, the individual has serum CA19-9 level that is ≥59×ULN. In some embodiments, the individual is human. In some embodiments, the taxane is paclitaxel. In some embodiments, the carrier protein is an albumin (such as human albumin or human serum albumin). In some embodiments, the treatment is first line treatment. In some embodiments, the individual has hENT1 overexpression (for example based on immunohistochemistry evaluation). In some embodiments, the individual has decreased (low) hENT1 expression (for example based on immunohistochemistry evaluation).

In some embodiments, there is provided a method of treating metastatic pancreatic cancer (such as metastatic adenocarcinoma of the pancreas) in a human individual comprising administering (for example intravenously) to the individual (i) an effective amount of Nab-paclitaxel (for example about 5 mg/ml Nab-paclitaxel); and (ii) an effective amount of gemcitabine, wherein the dose of paclitaxel in the nanoparticle composition is between about 50 mg/m$^2$ and about 200 mg/m$^2$ (such as about 100 mg/m$^2$ and about 200 mg/m$^2$ or about 100 mg/m$^2$ and about 150 mg/m$^2$, for example about 125 mg/m$^2$). In some embodiments, the nanoparticle composition is administered weekly (for example three out of four weeks in a four week cycle). In some embodiments, the dose of gemcitabine is about 600 mg/m$^2$ to about 2000 mg/m$^2$ (such as about 1000 mg/m$^2$ to about 2000 mg/m$^2$, for example about 1000 mg/m$^2$). In some embodiments, the gemcitabine is administered weekly (for example three out of four weeks in a four week cycle). In some embodiments, the individual is treated for at least about 2 months, for example at least about any of 3, 4, 5, 6, 7, 8, 9, 10, 11, 12, or more months.

In some embodiments, there is provided a method of treating metastatic pancreatic cancer (such as metastatic adenocarcinoma of the pancreas) in a human individual comprising administering (for example intravenously) to the individual (i) an effective amount of Nab-paclitaxel (for example about 5 mg/ml Nab-paclitaxel); and (ii) an effective amount of gemcitabine, wherein the individual has at least about 3 (e.g., more than 3) metastatic sites, wherein the dose of paclitaxel in the nanoparticle composition is between about 50 mg/m$^2$ and about 200 mg/m$^2$ (such as between about 100 mg/m$^2$ and about 150 mg/m$^2$, for example about 125 mg/m$^2$). In some embodiments, the nanoparticle composition is administered weekly (for example three out of four weeks in a four week cycle). In some embodiments, the dose of gemcitabine is about 600 mg/m$^2$ to about 2000 mg/m$^2$ (such as about 1000 mg/m$^2$). In some embodiments, the gemcitabine is administered weekly (for example three out of four weeks in a four week cycle). In some embodiments, the individual is treated for at least about 2 months, for example at least about any of 3, 4, 5, 6, 7, 8, 9, 10, 11, 12, or more months.

In some embodiments, there is provided a method of treating stage IV or locally advanced unresectable pancreatic cancer in a human individual comprising administering (for example intravenously) to the individual (i) an effective amount of Nab-paclitaxel (for example about 5 mg/ml Nab-paclitaxel); and (ii) an effective amount of gemcitabine, wherein the dose of paclitaxel in the nanoparticle composition is between about 50 mg/m$^2$ and about 200 mg/m$^2$ (such as between about 100 mg/m$^2$ and about 150 mg/m$^2$, for example about mg/m$^2$). In some embodiments, the nanoparticle composition is administered weekly (for example three out of four weeks in a four week cycle). In some embodiments, the dose of gemcitabine is about 600 mg/m$^2$ to about 2000 mg/m$^2$ (such as about 1000 mg/m$^2$). In some embodiments, the gemcitabine is administered weekly (for example three out of four weeks in a four week cycle). In some embodiments, the individual is treated for at least about 2 months, for example at least about any of 3, 4, 5, 6, 7, 8, 9, 10, 11, 12, or more months.

In some embodiments, there is provided a method of treating metastatic pancreatic cancer (such as metastatic adenocarcinoma of the pancreas) in a human individual comprising administering (for example intravenously) to the individual (i) an effective amount of Nab-paclitaxel (for example about 5 mg/ml Nab-paclitaxel); and (ii) an effective amount of gemcitabine, wherein the primary location of the pancreatic cancer is in the head of the pancreas, wherein the dose amount of paclitaxel in the nanoparticle composition is between about 50 mg/m$^2$ and about 200 mg/m$^2$ (such as between about 100 mg/m$^2$ and about 150 mg/m$^2$, for example about mg/m$^2$). In some embodiments, the nanoparticle composition is administered weekly (for example three out of four weeks in a four week cycle). In some embodiments, the dose of gemcitabine is about 600 mg/m$^2$ to about 2000 mg/m$^2$ (such as about 1000 mg/m$^2$). In some embodiments, the gemcitabine is administered weekly (for example three out of four weeks in a four week cycle). In some embodiments, the individual is treated for at least about 2 months, for example at least about any of 3, 4, 5, 6, 7, 8, 9, 10, 11, 12, or more months.

In some embodiments, there is provided a method of treating metastatic pancreatic cancer (such as metastatic adenocarcinoma of the pancreas) in a human individual comprising administering (for example intravenously) to the individual (i) an effective amount of Nab-paclitaxel (for example about 5 mg/ml Nab-paclitaxel); and (ii) an effective amount of gemcitabine, wherein the individual has metastasis in the liver, wherein the dose of paclitaxel in the nanoparticle composition is between about 50 mg/m$^2$ and about 200 mg/m$^2$ (such as between about 100 mg/m$^2$ and about 150 mg/m$^2$, for example about mg/m$^2$). In some embodiments, the nanoparticle composition is administered weekly (for example three out of four weeks in a four week cycle). In some embodiments, the dose of gemcitabine is about 600 mg/m$^2$ to about 2000 mg/m$^2$ (such as about 1000 mg/m$^2$). In some embodiments, the gemcitabine is administered weekly (for example three out of four weeks in a four week cycle). In some embodiments, the individual is treated for at least about 2 months, for example at least about any of 3, 4, 5, 6, 7, 8, 9, 10, 11, 12, or more months.

In some embodiments, there is provided a method of treating pancreatic cancer (such as metastatic or locally advanced unresectable pancreatic cancer) in a human individual comprising administering (for example intravenously) to the individual (i) an effective amount of Nab-paclitaxel (for example about 5 mg/ml Nab-paclitaxel); and (ii) an effective amount of gemcitabine, wherein the individual has serum CA19-9 level that is ≥59×ULN, wherein the dose of paclitaxel in the nanoparticle composition is between about 50 mg/m$^2$ and about 200 mg/m$^2$ (such as between about 100 mg/m² and about 150 mg/m², for example about mg/m²). In some embodiments, the nanoparticle composition is administered weekly (for example three out of four weeks in a four week cycle). In some embodiments, the dose of gemcitabine is about 600 mg/m² to about 2000 mg/m² (such as about 1000 mg/m²). In some embodiments, the gemcitabine is administered weekly (for example three out of four weeks in a four week cycle). In some embodiments, the individual is treated for at least about 2 months, for example at least about any of 3, 4, 5, 6, 7, 8, 9, 10, 11, 12, or more months.

In some embodiments, there is provided a method of treating pancreatic cancer (such as metastatic or locally advanced unresectable pancreatic cancer) in a human individual comprising administering (for example intravenously) to the individual (i) an effective amount of Nab-paclitaxel (for example about 5 mg/ml Nab-paclitaxel); and (ii) an effective amount of gemcitabine, wherein the individual has KPS score of less than about 90 (for example about 70-80), wherein the dose of paclitaxel in the nanoparticle composition is between about 50 mg/m² and about 200 mg/m² (such as between about 100 mg/m² and about 150 mg/m², for example about mg/m²). In some embodiments, the nanoparticle composition is administered weekly (for example three out of four weeks in a four week cycle). In some embodiments, the dose of gemcitabine is about 600 mg/m² to about 2000 mg/m² (such as about 1000 mg/m²). In some embodiments, the gemcitabine is administered weekly (for example three out of four weeks in a four week cycle). In some embodiments, the individual is treated for at least about 2 months, for example at least about any of 3, 4, 5, 6, 7, 8, 9, 10, 11, 12, or more months.

In some embodiments, there is provided a method of treating locally advanced unresectable or metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 125 mg/m² on days 1, 8, and 15 of each 28 day cycle, and wherein the dose of gemcitabine is about 1000 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating locally advanced unresectable or metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 100 mg/m² on days 1, 8, and 15 of each 28 day cycle, and wherein the dose of gemcitabine is about 800 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating locally advanced unresectable or metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 75 mg/m² on days 1, 8, and 15 of each 28 day cycle, and wherein the dose of gemcitabine is about 600 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has at least about 3 (e.g., more than 3) metastatic sites, wherein the dose of paclitaxel in the nanoparticle composition is about 125 mg/m² on days 1, 8, and 15 of each 28 day cycle, and wherein the dose of gemcitabine is about 1000 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has at least about 3 (e.g., more than 3) metastatic sites, wherein the dose of paclitaxel in the nanoparticle composition is about 100 mg/m² on days 1, 8, and 15 of each 28 day cycle, and wherein the dose of gemcitabine is about 800 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has at least about 3 (e.g., more than 3) metastatic sites, wherein the dose of paclitaxel in the nanoparticle composition is about 75 mg/m² on days 1, 8, and 15 of each 28 day cycle, and wherein the dose of gemcitabine is about 600 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating locally advanced unresectable or metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the primary location of the pancreatic cancer is in the head of the pancreas, wherein the dose of paclitaxel in the nanoparticle composition is about 125 mg/m$^2$ on days 1, 8, and 15 of each 28 day cycle, and wherein the dose of gemcitabine is about 1000 mg/m$^2$ on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating locally advanced unresectable or metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the primary location of the pancreatic cancer is in the head of the pancreas, wherein the dose of paclitaxel in the nanoparticle composition is about 100 mg/m$^2$ on days 1, 8, and 15 of each 28 day cycle, and wherein the dose of gemcitabine is about 800 mg/m$^2$ on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating locally advanced unresectable or metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the primary location of the pancreatic cancer is in the head of the pancreas, wherein the dose of paclitaxel in the nanoparticle composition is about 75 mg/m$^2$ on days 1, 8, and 15 of each 28 day cycle, and wherein the dose of gemcitabine is about 600 mg/m$^2$ on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the dose of paclitaxel in the nanoparticle composition is about 125 mg/m$^2$ on days 1, 8, and 15 of each 28 day cycle, and wherein the dose of gemcitabine is about 1000 mg/m$^2$ on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the dose of paclitaxel in the nanoparticle composition is about 100 mg/m$^2$ on days 1, 8, and 15 of each 28 day cycle, and wherein the dose of gemcitabine is about 800 mg/m$^2$ on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the dose of paclitaxel in the nanoparticle composition is about 75 mg/m$^2$ on days 1, 8, and 15 of each 28 day cycle, and wherein the dose of gemcitabine is about 600 mg/m$^2$ on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating locally advanced unresectable or metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has serum CA19-9 level that is ≥59×ULN, wherein the dose of paclitaxel in the nanoparticle composition is about 125 mg/m$^2$ on days 1, 8, and 15 of each 28 day cycle, and wherein the dose of gemcitabine is about 1000 mg/m$^2$ on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating locally advanced unresectable or metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has serum CA19-9 level that is ≥59×ULN, wherein the dose of paclitaxel in the nanoparticle composition is about 100 mg/m² on days 1, 8, and 15 of each 28 day cycle, and wherein the dose of gemcitabine is about 800 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating locally advanced unresectable or metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has serum CA19-9 level that is ≥59×ULN, wherein the dose of paclitaxel in the nanoparticle composition is about 75 mg/m² on days 1, 8, and 15 of each 28 day cycle, and wherein the dose of gemcitabine is about 600 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has at least about 3 (e.g., more than 3) metastatic sites, wherein the primary location of the pancreatic cancer is in the head of the pancreas, wherein the dose of paclitaxel in the nanoparticle composition is about 125 mg/m² on days 1, 8, and 15 of each 28 day cycle, and wherein the dose of gemcitabine is about 1000 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has at least about 3 (e.g., more than 3) metastatic sites, wherein the primary location of the pancreatic cancer is in the head of the pancreas, wherein the dose of paclitaxel in the nanoparticle composition is about 100 mg/m² on days 1, 8, and 15 of each 28 day cycle, and wherein the dose of gemcitabine is about 800 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has at least about 3 (e.g., more than 3) metastatic sites, wherein the primary location of the pancreatic cancer is in the head of the pancreas, wherein the dose of paclitaxel in the nanoparticle composition is about 75 mg/m² on days 1, 8, and 15 of each 28 day cycle, and wherein the dose of gemcitabine is about 600 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has at least about 3 (e.g., more than 3) metastatic sites, wherein the individual has serum CA19-9 level that is ≥59×ULN, wherein the dose of paclitaxel in the nanoparticle composition is about 125 mg/m² on days 1, 8, and 15 of each 28 day cycle, and wherein the dose of gemcitabine is about 1000 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has at least about 3 (e.g., more than 3) metastatic sites, wherein the individual has serum CA19-9 level that is ≥59×ULN, wherein the dose of paclitaxel in the nanoparticle composition is about 100 mg/m² on days 1, 8, and 15 of each 28 day cycle, and wherein the dose of gemcitabine is about 800 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has at least about 3 (e.g., more than 3) metastatic sites, wherein the individual has serum CA19-9 level that is ≥59×ULN, wherein the dose of paclitaxel in the nanoparticle composition is about 75 mg/m² on days 1, 8, and 15 of each 28 day cycle, and wherein the dose of gemcitabine is about 600 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has at least about 3 (e.g., more than 3) metastatic sites, wherein the primary location of the pancreatic cancer is in the head of the pancreas, wherein the individual has serum CA19-9 level that is ≥59×ULN, wherein the dose of paclitaxel in the nanoparticle composition is about 125 mg/m² on days 1, 8, and 15 of each 28 day cycle, and wherein the dose of gemcitabine is about 1000 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has at least about 3 (e.g., more than 3) metastatic sites, wherein the primary location of the pancreatic cancer is in the head of the pancreas, wherein the individual has serum CA19-9 level that is ≥59×ULN, wherein the dose of paclitaxel in the nanoparticle composition is about 100 mg/m² on days 1, 8, and 15 of each 28 day cycle, and wherein the dose of gemcitabine is about 800 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has at least about 3 (e.g., more than 3) metastatic sites, wherein the primary location of the pancreatic cancer is in the head of the pancreas, wherein the individual has serum CA19-9 level that is ≥59×ULN, wherein the dose of paclitaxel in the nanoparticle composition is about 75 mg/m² on days 1, 8, and 15 of each 28 day cycle, and wherein the dose of gemcitabine is about 600 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating locally advanced unresectable or metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the primary location of the pancreatic cancer is in the head of the pancreas, wherein the individual has serum CA19-9 level that is ≥59×ULN, wherein the dose of paclitaxel in the nanoparticle composition is about 125 mg/m² on days 1, 8, and 15 of each 28 day cycle, and wherein the dose of gemcitabine is about 1000 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating locally advanced unresectable or metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the primary location of the pancreatic cancer is in the head of the pancreas, wherein the individual has serum CA19-9 level that is ≥59×ULN, wherein the dose of paclitaxel in the nanoparticle composition is about 100 mg/m² on days 1, 8, and 15 of each 28 day cycle, and wherein the dose of gemcitabine is about 800 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating locally advanced unresectable or metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the primary location of the pancreatic cancer is in the head of the pancreas, wherein the individual has serum CA19-9 level that is ≥59×ULN, wherein the dose of paclitaxel in the nanoparticle composition is about 75 mg/m² on days 1, 8, and 15 of each 28 day cycle, and wherein the dose of gemcitabine is about 600 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the primary location of the pancreatic cancer is in the head of the pancreas, wherein the dose of paclitaxel in the nanoparticle composition is about 125 mg/m$^2$ on days 1, 8, and 15 of each 28 day cycle, and wherein the dose of gemcitabine is about 1000 mg/m$^2$ on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the primary location of the pancreatic cancer is in the head of the pancreas, wherein the dose of paclitaxel in the nanoparticle composition is about 100 mg/m$^2$ on days 1, 8, and 15 of each 28 day cycle, and wherein the dose of gemcitabine is about 800 mg/m$^2$ on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the primary location of the pancreatic cancer is in the head of the pancreas, wherein the dose of paclitaxel in the nanoparticle composition is about 75 mg/m$^2$ on days 1, 8, and 15 of each 28 day cycle, and wherein the dose of gemcitabine is about 600 mg/m$^2$ on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has serum CA19-9 level that is ≥59×ULN, wherein the dose of paclitaxel in the nanoparticle composition is about 125 mg/m$^2$ on days 1, 8, and 15 of each 28 day cycle, and wherein the dose of gemcitabine is about 1000 mg/m$^2$ on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has serum CA19-9 level that is ≥59×ULN, wherein the dose of paclitaxel in the nanoparticle composition is about 100 mg/m$^2$ on days 1, 8, and 15 of each 28 day cycle, and wherein the dose of gemcitabine is about 800 mg/m$^2$ on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has serum CA19-9 level that is ≥59×ULN, wherein the dose of paclitaxel in the nanoparticle composition is about 75 mg/m$^2$ on days 1, 8, and 15 of each 28 day cycle, and wherein the dose of gemcitabine is about 600 mg/m$^2$ on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has serum CA19-9 level that is ≥59×ULN, wherein the primary location of the pancreatic cancer is in the head of the pancreas, wherein the dose of paclitaxel in the nanoparticle composition is about 125 mg/m$^2$ on days 1, 8, and 15 of each 28 day cycle, and wherein the dose of gemcitabine is about 1000 mg/m$^2$ on days 1, 8, and 15 of each 28 day cycle. In some embodiments, the gemcitabine is administered immediately after the completion of the administration of the nanoparticle composition. In some embodiments, the individual is treated for at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has serum CA19-9 level that is ≥59×ULN, wherein the primary location of the pancreatic cancer is in the head of the pancreas, wherein the dose of paclitaxel in the nanoparticle composition is about 100 mg/m² on days 1, 8, and 15 of each 28 day cycle, and wherein the dose of gemcitabine is about 800 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has serum CA19-9 level that is ≥59×ULN, wherein the primary location of the pancreatic cancer is in the head of the pancreas, wherein the dose of paclitaxel in the nanoparticle composition is about 75 mg/m² on days 1, 8, and 15 of each 28 day cycle, and wherein the dose of gemcitabine is about 600 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has at least 3 (e.g., more than 3) metastatic sites, wherein the dose of paclitaxel in the nanoparticle composition is about 125 mg/m² on days 1, 8, and 15 of each 28 day cycle, and wherein the dose of gemcitabine is about 1000 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has at least 3 (e.g., more than 3) metastatic sites, wherein the dose of paclitaxel in the nanoparticle composition is about 100 mg/m² on days 1, 8, and 15 of each 28 day cycle, and wherein the dose of gemcitabine is about 800 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has at least 3 (e.g., more than 3) metastatic sites, wherein the dose of paclitaxel in the nanoparticle composition is about 75 mg/m² on days 1, 8, and 15 of each 28 day cycle, and wherein the dose of gemcitabine is about 600 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has at least 3 (e.g., more than 3) metastatic sites, wherein the individual has serum CA19-9 level that is ≥59×ULN, wherein the dose of paclitaxel in the nanoparticle composition is about 125 mg/m² on days 1, 8, and 15 of each 28 day cycle, and wherein the dose of gemcitabine is about 1000 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has at least 3 (e.g., more than 3) metastatic sites, wherein the individual has serum CA19-9 level that is ≥59×ULN, wherein the dose of paclitaxel in the nanoparticle composition is about 100 mg/m² on days 1, 8, and 15 of each 28 day cycle, and wherein the dose of gemcitabine is about 800 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has at least 3 (e.g., more than 3) metastatic sites, wherein the individual has serum CA19-9 level that is ≥59×ULN, wherein the dose of paclitaxel in the nanoparticle composition is about 75 mg/m² on days 1, 8, and 15 of each 28 day cycle, and wherein the dose of gemcitabine is about 600 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has at least 3 (e.g., more than 3) metastatic sites, wherein the primary location of the pancreatic cancer is in the head of the pancreas, wherein the dose of paclitaxel in the nanoparticle composition is about 125 mg/m² on days 1, 8, and 15 of each 28 day cycle, and wherein the dose of gemcitabine is about 1000 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has at least 3 (e.g., more than 3) metastatic sites, wherein the primary location of the pancreatic cancer is in the head of the pancreas, wherein the dose of paclitaxel in the nanoparticle composition is about 100 mg/m² on days 1, 8, and 15 of each 28 day cycle, and wherein the dose of gemcitabine is about 800 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has at least 3 (e.g., more than 3) metastatic sites, wherein the primary location of the pancreatic cancer is in the head of the pancreas, wherein the dose of paclitaxel in the nanoparticle composition is about 75 mg/m² on days 1, 8, and 15 of each 28 day cycle, and wherein the dose of gemcitabine is about 600 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has at least 3 (e.g., more than 3) metastatic sites, wherein the individual has serum CA19-9 level that is ≥59×ULN, wherein the primary location of the pancreatic cancer is in the head of the pancreas, wherein the dose of paclitaxel in the nanoparticle composition is about 125 mg/m² on days 1, 8, and 15 of each 28 day cycle, and wherein the dose of gemcitabine is about 1000 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has at least 3 (e.g., more than 3) metastatic sites, wherein the individual has serum CA19-9 level that is ≥59×ULN, wherein the primary location of the pancreatic cancer is in the head of the pancreas, wherein the dose of paclitaxel in the nanoparticle composition is about 100 mg/m² on days 1, 8, and 15 of each 28 day cycle, and wherein the dose of gemcitabine is about 800 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating metastatic adenocarcinoma of the pancreas in a human individual comprising intravenously administering (such as by intravenous infusion over about 30 to about 40 minutes) to the individual (i) an effective amount of Nab-paclitaxel (for example about 5 mg/ml Nab-paclitaxel); and (ii) an effective amount of gemcitabine, wherein the individual has metastasis in the liver, wherein the individual has at least 3 (e.g., more than 3) metastatic sites, wherein the individual has serum CA19-9 level that is ≥59×ULN, wherein the primary location of the pancreatic cancer is in the head of the pancreas, wherein the dose of paclitaxel in the nanoparticle composition is about 75 mg/m² on days 1, 8, and 15 of each 28 day cycle, and wherein the dose of gemcitabine is about 600 mg/m² on days 1, 8, and 15 of each 28 day cycle. In some embodiments, the gemcitabine is administered immediately after the completion of the administration of the nanoparticle composition. In some embodiments, the individual is treated for at least about 2 months, for example at least about any of 3, 4, 5, 6, 7, 8, 9, 10, 11, 12, or more months.

In some embodiments, there is provided a method of treating pancreatic cancer in an individual (such as any of the individuals described herein) by following any one of the dosing regimens provided in Table 3.

TABLE 3

Dosing Regimens

| Pancreatic Cancer Patient Setting | Line of Treatment | Study Topic | Study Design |
|---|---|---|---|
| Metastatic, Advanced | Previously treated | Nab-paclitaxel (NP) in patients with advanced pancreatic cancer (PC) who have progressed on gemcitabine-based therapy. | Dosage Regimen: 28-day cycle: 100 mg/m$^2$ Nab-paclitaxel on days 1, 8, and 15. Treatment Duration: Until disease progression or intolerance. |
| Mucinous Cystic Neoplasms (Premalignant and Malignant) | N/A | EUS Guided Injection of Albumin Bound Paclitaxel Into Pancreatic Cysts | 5-10 mg Abraxane ® injected into cyst cavity after Endoscopic Ultrasound Fine Needle Aspiration (EUS-FNA) to remove the fluid. |
| Metastatic | First line, Chemo-naïve | Nab-paclitaxel (a), gemcitabine (gem), and capecitabine (x) in patients with metastatic pancreatic adenocarcinoma | Dosage Regimen: 14 day cycle: 100 to 150 mg/m$^2$ Nab-paclitaxel in combination with 750 to 1000 mg/m$^2$ gemcitabine on day 4 and 500 to 1000 mg/m$^2$ Capecitabine on days 1 to 7 in a 3 + 3 dose escalation design. Treatment Duration: Until progression or toxicity. |
| Resectable | Neo-adjuvant | Gemcitabine and Abraxane ® as preoperative therapy for potentially operable pancreatic cancer | Dosage Regimen: 28 day cycle: 125 mg/m$^2$ Abraxane ® in combination with 1000 mg/m$^2$ gemcitabine weekly for three weeks of cycle. Treatment Duration: For 3 months (3 cycles) prior to surgery. |
| Metastatic, Advanced, Stage IV | First line, Chemo-naïve | Nab-paclitaxel in combination with various regimens in patients with metastatic pancreatic cancer | Dosage Regimen: (Arm A) Nab-paclitaxel in combination with 5-Fluorouracil, Leucovorin, Oxaliplatin, and Bevacizumab; (Arm B) Nab-paclitaxel in combination with gemcitabine and Salirasib; (Arm C) Nab-paclitaxel in combination with gemcitabine and Sunitinib; and (Arm D) Nab-paclitaxel in combination with gemcitabine and Carfilzomib. |
| Stage IV | N/A | Induction consolidation and maintenance approach for patients with advanced pancreatic cancer | Dosage Regimen: 125 mg/m$^2$ Nab-paclitaxel in combination with 1000 mg/m$^2$ gemcitabine weekly for three weeks every four weeks followed by FOLFIRINOX (400 mg/m$^2$ 5-Fluorouracil, 400 mg/m$^2$ Leucovorin, 85 mg/m$^2$ Oxaliplatin, and 180 mg/m$^2$ Irinotecan on day 1 followed by 2400 mg/m$^2$ 5-Fluorouracil biweekly) and then by maintenance (Cox 2 receptor = Celecoxib, Wild type ras = Cetuximab, Vitamin D Receptor = Calcitriol, MGMT = Temozolomide, and PTEN deleted = Rapamycin). Treatment Duration: One cycle past normalization of serum marker, not to exceed six cycles. |
| Stage I, Stage II, Stage II | N/A | Nab-paclitaxel in combination with gemcitabine in operable pancreatic cancer | Dosage Regimen: 28 day cycle: 125 mg/m$^2$ Nab-paclitaxel in combination with 1000 mg/m$^2$ gemcitabine on days 1, 8, and 15. Treatment Duration: Two cycles prior to surgery. |
| Metastatic | Second line | Oral capecitabine in combination with Nab-paclitaxel as systemic second line chemotherapy for patients with metastatic pancreatic cancer after failure of first-line gemcitabine-based treatment | Dosage Regimen: 21 day cycle: 125 mg/m$^2$ Abraxane ® on days 1 and 8 in combination with two doses of 825 mg/m$^2$/d Capecitabine on days 1 to 14. Treatment Duration: Until disease progression or unacceptable toxicities. |

TABLE 3-continued

Dosing Regimens

| Pancreatic Cancer Patient Setting | Line of Treatment | Study Topic | Study Design |
|---|---|---|---|
| Resectable | Neo-adjuvant | Gemcitabine, Nab-paclitaxel and lde-225 (hedgehog inhibitor) as neoadjuvant therapy in patients with borderline resectable pancreatic adenocarcinoma | Dosage Regimen: 125 mg/m$^2$ Abraxane ® weekly in combination with 1000 mg/m$^2$ gemcitabine weekly and 800 mg LDE-225 daily or RP2 dose. (Arm 1) 125 mg/m$^2$ Abraxane ® weekly in combination with 1000 mg/m$^2$ gemcitabine weekly and LDE-225 RP2 dose; (Arm 2) 125 mg/m$^2$ Abraxane ® weekly in combination with 1000 mg/m$^2$ gemcitabine weekly; and (Arm 3) 1000 mg/m$^2$ gemcitabine weekly and LDE-225 RP2 dose. Treatment Duration: Four cycles prior to surgery followed by Intensity Modulated Radiation Therapy for margins + subjects or six cycles of treatment for margins − patients. |
| Resectable | N/A | Pre-operative chemotherapy and targeted exercise program for resectable pancreatic cancer | Dosage Regimen: 28 day cycle: (Pre-Op) 125 mg/m$^2$ Abraxane ® in combination with 1000 mg/m$^2$ gemcitabine on days 1, 8, and 15. Treatment Duration: Eight weeks. 28 day cycle: (Post-Op) 125 mg/m$^2$ Abraxane ® in combination with 1000 mg/m$^2$ gemcitabine on days 1, 8, and 15. Treatment Duration: Sixteen weeks. |
| Metastatic, Advanced | Chemo-naïve | Gemcitabine plus Nab-paclitaxel is an active regimen in Patients with advanced pancreatic cancer | Dosage Regimen: 28 day cycle: 100 to 150 mg/m$^2$ Nab-paclitaxel in combination with 1000 mg/m$^2$ gemcitabine on days 1, 8, and 15. |
| Metastatic | N/A | Weekly AB1-007 plus gemcitabine versus gemcitabine alone in patients with metastatic adenocarcinoma of the pancreas | Dosage Regimen: (Cohort 1) 125 mg/m$^2$ Nab-paclitaxel in combination with 1000 mg/m$^2$ gemcitabine weekly for 3 weeks followed by one week of rest vs. (Cohort 2) 1000 mg/m$^2$ gemcitabine administered for 7 weeks followed by a week of rest (cycle 1), followed by weekly administration for 3 weeks followed by a week of rest (cycle 2 and onward). |
| Stage IV, Resectable, Unresectable | Neo-adjuvant, Previously treated with (Nab)-paclitaxel | Neoadjuvant therapy with nanoparticle albumin-bound (Nab)-paclitaxel to enhance the resectability of locally advanced pancreatic cancer | Dosage Regimen: 100 to 125 mg/m$^2$ Abraxane ® on days 1, 8, and 15 in combination with gemcitabine or Carboplatin. Treatment Duration: Five cycles. |
| N/A | N/A | Effect of Nab-paclitaxel combination chemotherapy on response and survival in pancreatic cancer | Previously treated with Nab-paclitaxel in combination with gemcitabine or carboplatin. |
| Metastatic, unresectable | First line | Gemcitabine + Abraxane ® with or without ODSH (2-0, 3-0 desulfated heparin) as first line treatment of metastatic pancreatic cancer | Dosage Regimen: 28 day cycle: (Arm A) 125 mg/m$^2$ Nab-paclitaxel in combination with 1000 mg/m$^2$ gemcitabine and 4 mg/kg ODSH (2-O, 3-O Desulfated Heparin) weekly for 3 weeks followed by one week of rest vs. (Arm B) 125 mg/m$^2$ Nab-paclitaxel in combination with 1000 mg/m$^2$ gemcitabine weekly for 3 weeks followed by one week of rest. |
| Locally advanced, unresectable metastatic | Chemo-naïve, First line | Erlotinib in combination with gemcitabine and Nab-paclitaxel in patients with previously untreated advanced pancreatic cancer | Dosage Regimen: Nab-paclitaxel weekly in combination with gemcitabine (weekly) and Erlotinib daily. |

TABLE 3-continued

Dosing Regimens

| Pancreatic Cancer Patient Setting | Line of Treatment | Study Topic | Study Design |
|---|---|---|---|
| Locally advanced, unresectable metastatic | First line | Evaluation of tumoral perfusion modification by dynamic imaging after chemotherapy combining gemcitabine and Nab-paclitaxel (Abraxane ®) in patients with potentially operable, locally advanced or metastatic pancreatic adenocarcinoma | Dosage Regimen: 28 day cycle: (Cohort 1, resectable) 125 mg/m² Abraxane ® in combination with 1000 mg/m² gemcitabine on days 1, 8, and 15. Treatment Duration: 1 cycle before surgery 28 day cycle: (Cohort 2, locally advanced and metastatic) 125 mg/m² Abraxane ® in combination with 1000 mg/m² gemcitabine on days 1, 8, and 15. Treatment Duration: Ay least 2 cycles or more in case of response of stable disease. |
| Metastatic | First line | Gemcitabine and Nab-paclitaxel in combination with GDC-0449 (hedgehog inhibitor) in patients with previously untreated metastatic adenocarcinoma of the pancreas | Dosage Regimen: 125 mg/m² Nab-paclitaxel in combination with 1000 mg/m² gemcitabine on days 1, 8, and 15 for one cycle (28 day cycle) then followed with 125 mg/m² Nab-paclitaxel in combination with 1000 mg/m² gemcitabine on days 1, 8, and 15 and 150 mg GDC-0449 daily every 28 day cycle. Treatment Duration: Until progressive disease, unacceptable toxicity or requirement of palliative radiotherapy. |
| Stage IV | First line, previously treated | Induction Consolidation and Maintenance Approach for Patients With Advanced Pancreatic Cancer | Dosage Regimen: 28 day cycle: 125 mg/m² Nab-paclitaxel in combination with 1000 mg/m² gemcitabine, 2400 mg/m² 5-Fluorouracil, 400 mg/m² Leucovorin, 85 mg/m² Oxaliplatin, and 180 mg/m² Irinotecan on days 1, 8, and 15. Followed by maintenance phase with 500 mg Metformin daily. |
| Stage III, Stage IV | Chemo-naïve | PAXG in Stage III-IV Pancreatic Adenocarcinoma | Dosage Regimen: 28 day cycle: (Arm A) Nab-paclitaxel at RP2D on days 1 and 15 in combination with 30 mg/m² cisplatin on days 1 and 15, 800 mg/m² gemcitabine on days 1 and 15, and 1250 mg/m² capecitabine on days 1 to 28 vs. (Arm B) PAXG regimen 30 mg/m² cisplatin on days 1 and 15, 30 mg/m² epirubicin on days 1 and 15, 800 mg/m² gemcitabine on days 1 and 15, and 1250 mg/m² capecitabine on days 1 to 28. Treatment Duration: A maximum of 6 cycles or until there is a clinical benefit. |
| Locally advanced, Unresectable | N/A | Gemcitabine/Abraxane ® Chemotherapy and Dose Escalated Radiotherapy for Locally Advanced, Unresectable Pancreatic Cancer | Dosage Regimen: (Prior to chemoradiation) 100 mg/m² Abraxane ® in combination with 1000 mg/m² gemcitabine on days 1, 8, and 15 for 2 cycles (28 day cycle); (Post chemoradiation) 100 mg/m² Abraxane ® in combination with 450 mg/m² gemcitabine weekly for 6 weeks. Treatment Duration: After last two cycles will be continued if well tolerated. |

TABLE 3-continued

Dosing Regimens

| Pancreatic Cancer Patient Setting | Line of Treatment | Study Topic | Study Design |
|---|---|---|---|
| Low-risk resectable, high-risk resectable, borderline resectable | Chemo-naïve | Gemcitabine With Abraxane ® and Other Investigational Therapies in Neoadjuvant Treatment of Pancreatic Adenocarcinoma | Dosage Regimen: 28 day cycle: (Low Risk): 100 mg/m² Nab-paclitaxel in combination with 1000 mg/m² gemcitabine on days 1, 8, and 15. Treatment Duration: Four cycles prior to resection. 28 day cycle: (High Risk and Borderline): 100 mg/m² Nab-paclitaxel in combination with 1000 mg/m² gemcitabine on days 1, 8, and 15 and radiation therapy. Treatment Duration: Two cycles prior to resection. |
| Metastatic | Chemo-naïve, Previously treated | Gemcitabine (Gemzar ®) plus Nab-paclitaxel (Abraxane ®) in patients with advanced metastatic pancreatic cancer | Dosage Regimen: 3 patients entered at low dose A, if no DLT-3 more patients enrolled at dose B. Treatment Duration: Until progression or inacceptable toxicity develops. |
| Resectable, borderline resectable | Previously treated | Molecular Profiling to Guide Neoadjuvant Therapy for Resectable and Borderline Resectable Adenocarcinoma of the Pancreas | Dosage Regimen: (Arm A, presurgery): Eight weeks targeted chemotherapy, restaging; (Arm B, presurgery): Chemoradiotherapy, restaging; (Arm C1, presurgery): Eight weeks targeted chemotherapy; restaging, Chemoradiotherapy, restaging; (Arm C2, presurgery): Eight weeks standard chemotherapy, restaging, standard chemoradiotherapy, restaging; (Arm D1, postsurgery): Eight weeks target chemotherapy, restaging, chemoradiotherapy, restaging; (Arm D2, postsurgery): Eight weeks gemcitabine, restaging, chemoradiotherapy, restaging; (Arm E, postsurgery): chemoradiotherapy, restaging; (Arm F1, postsurgery): Eight weeks targeted chemotherapy, restaging, eight weeks targeted chemotherapy, restaging; (Arm F2, postsurgery): Eight weeks gemcitabine, restaging, eight weeks gemcitabine, restaging; and (Arm G, postsurgery): No additional therapy after surgery. |
| Metastatic | N/A | Abraxane ® plus gemcitabine in Combination with IPI-926 in Patients with Metastatic Cancer | N/A |
| Advanced | Previously untreated | Hydroxychloroquine in combination with gemcitabine plus Abraxane ® to inhibit autophagy in pancreatic cancer | Dosage Regimen: 28 day cycle, 125 mg/m² Abraxane ® in combination with 1000 mg/m² gemcitabine on days 1, 8, and 15 and 800 to 1200 mg/day Hydroxychloroquine daily at a dose escalation starting from day 1. Treatment Duration Until disease progression. Dosage Regimen: 28 day cycle, (Arm 1) 125 mg/m² Abraxane ® in combination with 1000 mg/m² gemcitabine and Hydroxychloroquine MTD on days 1, 8, and 15 vs. (Arm 2) 125 mg/m² Abraxane ® in combination with 1000 mg/m² gemcitabine on days 1, 8, and 15. Treatment Duration Until disease progression. |

TABLE 3-continued

| Pancreatic Cancer Patient Setting | Line of Treatment | Study Topic | Study Design |
|---|---|---|---|
| Non-downstageable | N/A | Abraxane ® plus gemcitabine plus FG-3019 as neoadjuvant therapy for locally advanced, non-downstageable pancreatic cancer with surgical intent | Dosage Regimen: 28 day cycle: 125 mg/m$^2$ Abraxane ® in combination with 1000 mg/m$^2$ gemcitabine weekly every 3 weeks of cycle and FG-3019. Treatment Duration: Six cycles prior to surgery. |
| Unresectable, Locally advanced | N/A | Gemcitabine plus Abraxane ® plus Hedgehog Inhibition (HHI) and Stereotactic Body Radiation Therapy (SBRT) for patients with unresectable locally advanced pancreatic cancer. | Dosage Regimen: 125 mg/m$^2$ Abraxane ® in combination with 1000 mg/m$^2$ gemcitabine weekly every 3 weeks of 4 week cycle and Vismodegib for 4 cycles followed by SBRT hen followed by Abraxane ® in combination with gemcitabine and Vismodegib for two cycles followed Vismodegib. Treatment Duration: Until disease progression. |
| Resectable, Borderline resectable | N/A | Per-operative chemotherapy with gemcitabine and Abraxane ® (Nab-paclitaxel) with chemoradiotherapy for borderline resectable and node-positive pancreatic adenocarcinoma | Dosage Regimen: 125 mg/m$^2$ Abraxane ® in combination with 1000 mg/m$^2$ gemcitabine weekly for 3 weeks of 4 week cycle for two cycles followed by chemoradiotherapy followed by surgery then 4 post-operative cycles of Abraxane ® in combination with gemcitabine. |
| Metastatic | N/A | Nab-paclitaxel, 5-Flurouracil, Leucovorin, Oxaliplatin and Bevacizumab for Patients with Metastatic Pancreatic Adenocarcinoma | Dosage Regimen: 28 day cycle: Nab-paclitaxel in combination with Leucovorin, Oxaliplatin on days 1, 8, and 15 and Bevacizumab on days 1 and 15 and 5-Fluorouracil on days 1 to 14. Treatment Duration: Until disease progression or intolerance. |
| Metastatic | N/A | Gemcitabine/Nab-paclitaxel versus gemcitabine in Select[1]Patients with Metastatic Pancreatic Cancer | Dosage Regimen: 28 day cycle: (Arm 1) 1000 mg/m$^2$ gemcitabine on days 1, 8, and 15 vs. (Arm 2) 100 mg/m$^2$ Abraxane ® in combination with 1000 mg/m$^2$ gemcitabine on days 1 and 15. Treatment Duration: For six cycles or clinician discretion. |
| N/A | Adjuvant | Gemcitabine plus Nab-paclitaxel as adjuvant therapy for resected adenocarcinoma of the pancreas. | N/A |
| Stage IV | First line | N/a[2] | Dosage Regimen (Old Design): After resection, (Arm A) high immunohistochemistry for hENT1 treat with gemcitabine, (Arm B) low hENT1 treat with 5-Fluorouracil and Leucovorin; and (Arm C) Nab-paclitaxel and gemcitabine independent of hENT1. Dosage Regimen (New Design): After resection, (Arm A) high immunohistochemistry for hENT1 treat with gemcitabine, (Arm B) high hENT1 treat with Nab-paclitaxel and gemcitabine, (Arm C) low hENT1 treat with 5-Fluorouracil and Leucovorin; and (Arm D) low hENT1 treat with Nab-paclitaxel and gemcitabine. |
| Metastatic | First line | Gemcitabine plus Nab-paclitaxel followed by FOLFIRINOX in patients with first-line metastatic pancreatic adenocarcinoma (Phase I/II) | Dosage Regimen: Abraxane ® followed by FOLFIRINOX |

TABLE 3-continued

Dosing Regimens

| Pancreatic Cancer Patient Setting | Line of Treatment | Study Topic | Study Design |
|---|---|---|---|
| Locally advanced | First line | Combination of Abraxane ® and gemcitabine versus a combination of gemcitabine and Oxaliplatin as first line treatment in locally advanced unresectable pancreatic cancer. | Dosage Regimen: (Arm A) Abraxane ® in combination with gemcitabine vs. (Arm B) gemcitabine in combination with Oxaliplatin |
| Metastatic | First line | Two different schedules of Nab-paclitaxel (Abraxane ®) combined with gemcitabine with gemcitabine alone as first line treatment for metastatic pancreatic adenocarcinoma | Dosage Regimen: (Arm A) Abraxane ® in combination with gemcitabine vs. (Arm B) gemcitabine |
| Metastatic | First line | Weekly Nab-paclitaxel plus gemcitabine or Simplified LV5FU2 as First-line Therapy in Patients with Metastatic Pancreatic Cancer | Dosage Regimen: (Arm A) Abraxane ® in combination with gemcitabine vs. (Arm B) Leucovorin in combination with 5-Fluorouracil |
| Metastatic | N/A | The biological effect of Nab-paclitaxel combined to gemcitabine, in patients with metastatic pancreatic adenocarcinoma | Dosage Regimen: Abraxane ® in combination with gemcitabine |
| Locally advanced | N/A | Gemcitabine plus Nab-paclitaxel for locally advanced pancreatic cancer | Dosage Regimen: Abraxane ® in combination with gemcitabine |
| N/A | N/A | The combination of Nab-paclitaxel (Abraxane ®) with CO-101 (Clovis compound) a lipophilic pro-drug of gemcitabine | Dosage Regimen: Abraxane ® in combination with CO-101 |
| Locally advanced, Metastatic | N/A | A novel therapy for locally advanced and/or metastatic pancreatic cancer based on nanoparticle albumin-bound paclitaxel in combination with gemcitabine: Circulating tumor cells as a potential biomarker for treatment monitoring, -response and survival | Dosage Regimen: Abraxane ® in combination with gemcitabine and biomarker |
| Nonresectable, Locally advanced | Neo-adjuvant | Alternating neoadjuvant chemotherapy regimes in locally advanced, non-resectable adenocarinoma of the pancreas | N/A |
| Metastatic | N/A | Abraxane ®-gemcitabine for metastatic pancreatic cancer | Dosage Regimen: Abraxane ® in combination with gemcitabine |
| N/A | N/A | Abraxane ® + capecitabine | Dosage Regimen: Abraxane ® in combination with Capecitabine |
| N/A | N/A | Nab-FOLFIRI, Nab-FOLFOX | Dosage Regimen: (Arm A) Abraxane ® in combination with FOLFIRI and (Arm B) Abraxane ® in combination with FOLFOX |
| N/A | N/A | Abraxane ® + gemcitabine neoadjuvant vs. Adjuvant | Dosage Regimen: (Arm A) Abraxane ® in combination with gemcitabine as neoadjuvant vs. (Arm B) Abraxane ® in combination with gemcitabine as adjuvant |
| Advanced, Stage IV | N/A | Low-dose continuous infusion 5-fluorouracil combined with weekly leucovorin, Nab-paclitaxel, oxaliplatin, and bevacizumab for patients with advanced pancreatic cancer: | Dosage Regimen: 100 mg/m² Nab-paclitaxel in combination with 20 mg/m² Leucovorin, 50 mg/m² Oxaliplatin, 5 mg/m² Bevacizumab on days 1 and 15, and 180 mg/m²/d 5-Fluorouracil on days 1 to 15. Cycle repeated every 28 to 35 days. |

[1]"Select patients" also referred to as "fragile patients".
[2]A phase II study In some embodiments, there is provided a method of treating metastatic or locally advanced unresectable pancreatic cancer (such as metastatic adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of capecitabine (Xeloda). Capecitabine is an orally-administered chemotherapeutic agent that is enzymatically converted to 5-fluorouracil in the tumor, where it can inhibit DNA synthesis and slow tumor growth. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of 5-FU (fluorouracil) (Efudex). 5-FU is an antimetabolite that acts primarily as a thymidylate synthase inhibitor that can block the synthesis of dTMP, thus disrupting DNA synthesis and cell division in cancer cells. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of FOLFIRINOX. FOLFIRINOX is a drug combination that includes fluorouracil (described above), Leucovorin Calcium (Folinic Acid, which can enhance the effectiveness of fluorouracil), Irinotecan Hydrochloride (a topoisomerase inhibitor that can prevent DNA replication), and Oxaliplatin (a platinum-based compound that can inhibit DNA synthesis by forming inter- and intrastrand crosslinks in DNA). In some embodiments, the administration of FOLFIRINOX comprises administration of about 400 mg/m$^2$ 5-flurouracil, 400 mg/m$^2$ leucovorin, 85 mg/m$^2$ oxaliplatin, and 180 mg/m$^2$ irinotecan on day 1 followed by 2400 mg/m$^2$ 5-fluorouracil biweekly.

In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of FOLFIRI. FOLFIRI is a drug combination that includes Folinic Acid, fluorouracil, and Irinotecan, each of which is described above. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of FOLFOX. FOLFOX is a drug combination that includes Folinic acid (leucovorin), fluorouracil, and oxaliplatin, each of which is described above.

In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of oxaliplatin, a platinum-based compound that can inhibit DNA synthesis. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of a Hedgehog inhibitor. In some embodiments, the Hedgehog inhibitor inhibits the activity of Smoothened (SMO). In some embodiments, the Hedgehog inhibitor is a cyclopamine or derivative thereof. In some embodiments, the Hedgehog inhibitor is XL139, IP1926, or IPI609. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of vismodegib (also known as GDC-0449 or Erivedge™), a cyclopamine-competitive antagonist of the smoothened (SMO) receptor that can inhibit Hedgehog signaling. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of LDE-225, an orally available SMO antagonist that can inhibit Hedgehog signaling.

In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of leucovorin (or folinic acid), a folic acid analog that can enhance the activity of fluorouracil and can prevent harmful effects of methotrexate. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of bevacizumab, an antibody that can inhibit angiogenesis by targeting the VEGF-A protein. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of salirasib (farnesyl thiosalicylic acid), a salicylic acid derivative that can inhibit the activity of Ras. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of sunitinib (Sutent or SU11248), an anti-angiogenic agent that can inhibits receptor tyrosine kinases (such as PDGF-Rs, VEGFRs, and KIT (CD117)). In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of carfilzomib (CFZ or Kyprolis), an epoxomicin derivative that can cause cell cycle arrest by inhibiting the chymotrypsin-like activity of the 20S proteasome. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of irinotecan (Camptosar or Campto), a topoisomerase inhibitor that can inhibit DNA replication. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of celecoxib (Celebrex), a sulfonamide non-steroidal anti-inflammatory drug (NSAID) that can inhibit the activity of COX-2. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of cetuximab (Erbitux), an antibody that targets EFGR inhibitor and can inhibit cell division in patients with epidermal growth factor receptor (EGFR)-expressing, KRAS wild-type cancers. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of calcitriol (1,25-dihydroxycholecalciferol, 1,25-dihydroxyvitamin $D_3$, Rocaltrol, Calcijex, or Vectical), the hormonally active form of vitamin D that can exhibit antineoplastic activity.

In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of temozolomide (TMZ, Temodar, Temodal, or Temcad), a imidazotetrazine derivative of the alkylating agent dacarbazine that can inhibit DNA replication and cell division. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of rapamycin (Sirolimus), which can inhibit mTORC1, a downstream effector of the PI3K/AKT signaling pathway. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of cisplatin (Platin), a platinum compound that can bind to DNA, cause crosslinking, and trigger apoptosis. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of carboplatin (Paraplatin, Paraplatin-AQ), a platinum compound that can bind to DNA, causes crosslinking, and trigger apoptosis.

In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of ODSH (2-0, 3-0 Desulfated Heparin). ODSH is a desulfated heparin with minimal anticoagulation properties that can exhibit anti-metastatic effects and can enhance the effect of chemotherapy.

In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of metformin (Glucophage), an anti-diabetic drug that can reduce the risk of cancer. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of epirubicin (Ellence), an anthracycline drug that can inhibit DNA and RNA synthesis and topoisomerase II activity. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of erlotinib (Tarceva), which can inhibit EFGR signaling by targeting the EFGR tyrosine kinase. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of hydroxychloroquine (Plaquenil, Axemal, Dolquine, or Quensyl), an antimalarial drug that can inhibit the growth of tumors. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of FG-3019, a human monoclonal antibody against connective tissue growth factor (CTGF). FG-3019 can alter disease progression in Stage III and Stage IV cancer patients. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of CO-101, an antimetabolite deoxynucleoside analogue that can inhibit DNA synthesis and cell division. In some embodiments, there is provided a method of treating metastatic or locally advanced pancreatic cancer (such as adenocarcinoma of the pancreas) in a human individual comprising administering (for example intravenously) to the individual (i) an effective amount of Nab-paclitaxel (for example about 5 mg/ml Nab-paclitaxel), (ii) an effective amount of gemcitabine, and iii) an effective amount of IPI-926 (Saridegib), which can inhibit Hedgehog signaling by inhibiting the G protein-coupled receptor Smoothened (SMO).

In some embodiments according to (or as applied to) any of the triple or multiple combination therapy methods (e.g., Nab-paclitaxel plus gemcitabine plus another agent) described above, the individual has metastatic pancreatic cancer (such as metastatic adenocarcinoma of the pancreas). In some embodiments according to (or as applied to) any of the triple or multiple combination therapy methods (e.g., Na-paclitaxel plus gemcitabine plus another agent) described above, the individual has stage IV pancreatic cancer. In some embodiments according to (or as applied to) any of the triple or multiple combination therapy methods (e.g., Nab-paclitaxel plus gemcitabine plus another agent) described above, the individual has locally advanced unresectable pancreatic cancer. In some embodiments, the pancreatic cancer is pancreatic adenocarcinoma. In some embodiments according to (or as applied to) any of the triple or multiple combination therapy methods (e.g., Nab-paclitaxel plus gemcitabine plus another agent) described above, the individual is at least about 65 (or 70, or 75) years old. In some embodiments according to (or as applied to) any of the triple or multiple combination therapy methods (e.g., Nab-paclitaxel plus gemcitabine plus another agent) described above, the individual has at least about 3 (e.g., more than 3) metastatic sites. In some embodiments according to (or as applied to) any of the triple or multiple combination therapy methods (e.g., Nab-paclitaxel plus gemcitabine plus another agent) described above, the primary location of the pancreatic cancer is the head of the pancreas. In some embodiments according to (or as applied to) any of the triple or multiple combination therapy methods (e.g., Nab-paclitaxel plus gemcitabine plus another agent) described above, the individual has metastasis in the liver. In some embodiments according to (or as applied to) any of the triple or multiple combination therapy methods (e.g., Nab-paclitaxel plus gemcitabine plus another agent) described above, the individual has pulmonary metastasis. In some embodiments, the individual has peritoneal carcinomatosis. In some embodiments, the individual has serum CA19-9 level that is ≥59× ULN. In some embodiments according to (or as applied to) any of the triple or multiple combination therapy methods (e.g., Nab-paclitaxel plus gemcitabine plus another agent) described above, the treatment is first line treatment. In some embodiments according to (or as applied to) any of the triple or multiple combination therapy methods (e.g., Nab-paclitaxel plus gemcitabine plus another agent) described above, the individual has hENT1 overexpression (for example based on immunohistochemistry evaluation).

In some embodiments, there is provided a method of treating advanced metastatic pancreatic cancer in an individual, comprising intravenously administering to the individual an effective amount of a composition comprising nanoparticles comprising paclitaxel and human serum albumin (such as Nab-paclitaxel, for example Nab-paclitaxel at about 100 mg/m$^2$ on days 1, 8, and 15 of a 28 day cycle), wherein the individual has progressed on gemcitabine-based therapy. In some embodiments, there is provided a method of treating mucinous cystic neoplasm, comprising injecting to the cyst cavity of the individual an effective amount of a composition comprising nanoparticles comprising paclitaxel and human serum albumin (such as Nab-paclitaxel, for example about 5-10 mg Nab-paclitaxel). In some embodiments, there is provided a method of treating advanced stage IV metastatic pancreatic cancer in a chemotherapy naïve individual, comprising administering to the individual (a) an effective amount of a composition comprising nanoparticles comprising paclitaxel and human serum albumin (such as Nab-paclitaxel, for example Nab-paclitaxel at about 100 mg/m$^2$ on days 1, 8, and 15 of a 28 day cycle), (b) an effective amount of 5-fluorouracil, leucovorin, oxaliplatin, and bevacizumab. In some embodiments, there is provided a method of treating metastatic pancreatic cancer in an individual who has failed a gemcitabine-based therapy, comprising administering to the individual (a) an effective amount of a composition comprising nanoparticles comprising paclitaxel and human serum albumin (such as Nab-paclitaxel, for example Nab-paclitaxel at about 125 mg/m$^2$ on days 1, 8 of a 21 day cycle), (b) an effective amount of capecitabine (for example about 825 mg/m$^2$ orally on days 1-14 in a 21 day cycle). In some embodiments, there is provided a method of treating metastatic pancreatic cancer, comprising administering to the individual (a) an effective amount of a composition comprising nanoparticles comprising paclitaxel and human serum albumin (such as Nab-paclitaxel, for example Nab-paclitaxel at about 125 mg/m$^2$ on days 1, 8 of a 21 day cycle), (b) an effective amount of FOLFIRINOX. In some embodiments, there is provided a method of treating metastatic pancreatic cancer, comprising administering to the individual (a) an effective amount of a composition comprising nanoparticles comprising paclitaxel and human serum albumin (such as Nab-paclitaxel, for example Nab-paclitaxel at about 125 mg/m$^2$ on days 1, 8 of a 21 day cycle), (b) an effective amount of FOLFOX. In some embodiments, the pancreatic cancer is pancreatic adenocarcinoma. In some embodiments, the individual is at least about 65 (or 70, or 75) years old. In some embodiments, the individual has at least about 3 (e.g., more than 3) metastatic sites. In some embodiments, the primary location of the pancreatic cancer is the head of the pancreas. In some embodiments, the individual has metastasis in the liver. In some embodiments, the individual has peritoneal carcinomatosis. In some embodiments, the individual has serum CA19-9 level that is ≥59×ULN. In some embodiments, the treatment is first line treatment. In some embodiments, the individual has hENT1 overexpression (for example based on immunohistochemistry evaluation).

The methods described herein may further comprise selecting patients for treatment (e.g., identifying an individual who is suitable for treatment for pancreatic cancer). Thus, for example, in some embodiments, a method described herein further comprises identifying the individual having one of the characteristics described herein, such as pancreatic cancer subtype or staging characteristics, age, gender, CA19-9 level, metastases status, or Whipple procedure status described herein. In some embodiments, there is provided a method of treating pancreatic cancer (e.g., metastatic pancreatic adenocarcinoma) in an individual comprising administering to the individual (i) an effective amount of a composition comprising nanoparticles comprising a taxane (such as paclitaxel) and a carrier protein; and (ii) an effective amount of gemcitabine, wherein the individual is selected for treatment based on pancreatic cancer subtype or staging characteristics, age, gender, CA19-9 level, metastases status, or Whipple procedure status described herein.

In some embodiments, there is provided a method of treating pancreatic cancer in an individual (e.g., human) comprising the steps of (i) determining whether the individual has pancreatic cancer such as a pancreatic cancer described herein, and (ii) administering to the individual an effective amount of a composition comprising nanoparticles comprising a taxane (e.g., paclitaxel) and a carrier protein (e.g., an albumin) in combination with an effective amount of gemcitabine. In some embodiments, there is provided a method of treating pancreatic cancer in an individual (e.g., human) comprising the steps of (i) determining whether the individual has gender or age described herein, and (ii) administering to the individual an effective amount of a composition comprising nanoparticles comprising a taxane (e.g., paclitaxel) and a carrier protein (e.g., an albumin) in combination with an effective amount of gemcitabine. In some embodiments, there is provided a method of treating pancreatic cancer in an individual (e.g., human) comprising the steps of (i) determining whether the individual has pancreatic cancer such as CA19-9 level described herein, and (ii) administering to the individual an effective amount of a composition comprising nanoparticles comprising a taxane (e.g., paclitaxel) and a carrier protein (e.g., an albumin) in combination with an effective amount of gemcitabine. In some embodiments, there is provided a method of treating pancreatic cancer in an individual (e.g., human) comprising the steps of (i) determining whether the individual has metastasis status (e.g., location of metastasis sites, or number of metastasis sites), and (ii) administering to the individual an effective amount of a composition comprising nanoparticles comprising a taxane (e.g., paclitaxel) and a carrier protein (e.g., an albumin) in combination with an effective amount of gemcitabine. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating metastatic pancreatic cancer (such as metastatic adenocarcinoma of the pancreas) in an individual comprising administering (for example intravenously) to the individual wherein the individual is selected for treatment based on the metastatic status of the individual (for example the number of metastatic sites or the location of the metastases (such as liver)). In some embodiments, there is provided a method of treating metastatic pancreatic cancer (such as metastatic adenocarcinoma of the pancreas) in an individual comprising administering (for example intravenously) to the individual (i) an effective amount of Nab-paclitaxel (for example about 5 mg/ml Nab-paclitaxel); and (ii) an effective amount of gemcitabine, wherein the individual is selected for treatment based on the individual having 3 or more metastatic sites. In some embodiments, there is provided a method of treating metastatic pancreatic cancer (such as metastatic adenocarcinoma of the pancreas) in an individual comprising administering (for example intravenously) to the individual (i) an effective amount of Nab-paclitaxel (for example about 5 mg/ml Nab-paclitaxel); and (ii) an effective amount of gemcitabine, wherein the individual is selected for treatment based on the individual having metastasis in the liver. In some embodiments, there is provided a method of treating metastatic pancreatic cancer (such as metastatic adenocarcinoma of the pancreas) in an individual comprising administering (for example intravenously) to the individual (i) an effective amount of Nab-paclitaxel (for example about 5 mg/ml Nab-paclitaxel); and (ii) an effective amount of gemcitabine, wherein the individual is selected for treatment based on the individual having 3 or more metastatic sites and metastasis in the liver. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating metastatic pancreatic cancer (such as metastatic adenocarcinoma of the pancreas) in an individual comprising: a) determining the metastatic status of the individual, and administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating metastatic pancreatic cancer (such as metastatic adenocarcinoma of the pancreas) in an individual comprising: a) determining the metastatic status of the individual, and administering (for example intravenously) to the individual (i) an effective amount of Nab-paclitaxel (for example about 5 mg/ml Nab-paclitaxel); and (ii) an effective amount of gemcitabine, wherein the individual is selected for administration if the individual has 3 or more metastatic sites. In some embodiments, there is provided a method of treating metastatic pancreatic cancer (such as metastatic adenocarcinoma of the pancreas) in an individual comprising: a) determining the metastatic status of the individual, and administering (for example intravenously) to the individual (i) an effective amount of Nab-paclitaxel (for example about 5 mg/ml Nab-paclitaxel); and (ii) an effective amount of gemcitabine, wherein the individual is selected for treatment if the individual has metastasis in the liver. In some embodiments, there is provided a method of treating metastatic pancreatic cancer (such as metastatic adenocarcinoma of the pancreas) in an individual comprising: a) determining the metastatic status of the individual, and administering (for example intravenously) to the individual (i) an effective amount of Nab-paclitaxel (for example about 5 mg/ml Nab-paclitaxel); and (ii) an effective amount of gemcitabine, wherein the individual is selected for treatment if the individual has 3 or more metastatic sites and has metastasis in the liver. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating metastatic pancreatic cancer (such as metastatic adenocarcinoma of the pancreas) in an individual comprising: a) selecting the individual for treatment based on the metastatic status of the individual; and b) administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating metastatic pancreatic cancer (such as metastatic adenocarcinoma of the pancreas) in an individual comprising: a) selecting the individual for treatment based on the individual having 3 or more metastatic sites; and b) administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating metastatic pancreatic cancer (such as metastatic adenocarcinoma of the pancreas) in an individual comprising: a) selecting the individual for treatment based on the individual having metastasis in the liver; and b) administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating metastatic pancreatic cancer (such as metastatic adenocarcinoma of the pancreas) in an individual comprising: a) selecting the individual for treatment based on the individual having 3 or more metastatic sites and metastasis in the liver; and b) administering (for example intravenously) to the individual (i) an effective amount of Nab-paclitaxel (for example about 5 mg/ml Nab-paclitaxel); and (ii) an effective amount of gemcitabine. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating metastatic pancreatic cancer (such as metastatic adenocarcinoma of the pancreas) in an individual comprising: a) determining the metastatic status of the individual; b) selecting the individual for treatment based on the metastatic status of the individual; and c) administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating metastatic pancreatic cancer (such as metastatic adenocarcinoma of the pancreas) in an individual comprising: a) determining the metastatic status of the individual; b) selecting the individual for treatment based on the individual having 3 or more metastatic sites; and c) administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating metastatic pancreatic cancer (such as metastatic adenocarcinoma of the pancreas) in an individual comprising: a) determining the metastatic status of the individual; b) selecting the individual for treatment based on the individual having metastasis in the liver; and c) administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating metastatic pancreatic cancer (such as metastatic adenocarcinoma of the pancreas) in an individual comprising: a) determining the metastatis status of the individual; b) selecting the individual for treatment based on the individual having 3 or more metastatic sites and metastasis in the liver; and c) administering (for example intravenously) to the individual (i) an effective amount of Nab-paclitaxel (for example about 5 mg/ml Nab-paclitaxel); and (ii) an effective amount of gemcitabine. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m2 to about 150 mg/m2 (including for example about 75, about 80, or about 100 mg/m2) on days 1, 8, and 15 of each 28 day cycle, and wherein the dose of gemcitabine is about 500 mg/m2 to about 2000 mg/m2 (including for example about 600, about 800, or about 1000 mg/m2) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating pancreatic cancer (such as metastatic or locally advanced unresectable pancreatic cancer) in an individual comprising administering (for example intravenously) to the individual (i) an effective amount of Nab-paclitaxel (for example about 5 mg/ml Nab-paclitaxel); and (ii) an effective amount of gemcitabine, wherein the individual is selected for treatment based on the cancer stage of the individual. In some embodiments, there is provided a method of treating pancreatic cancer (such as metastatic or locally advanced unresectable pancreatic cancer) in an individual comprising administering (for example intravenously) to the individual (i) an effective amount of Nab-paclitaxel (for example about 5 mg/ml Nab-paclitaxel); and (ii) an effective amount of gemcitabine, wherein the individual is selected for treatment based on the individual having stage IV pancreatic cancer. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating pancreatic cancer (such as metastatic or locally advanced unresectable pancreatic cancer) in an individual comprising: a) determining the cancer stage of the individual, and administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating pancreatic cancer (such as metastatic or locally advanced unresectable pancreatic cancer) in an individual comprising: a) determining the cancer stage of the individual, and administering (for example intravenously) to the individual (i) an effective amount of Nab-paclitaxel (for example about 5 mg/ml Nab-paclitaxel); and (ii) an effective amount of gemcitabine, wherein the individual is selected for treatment if the individual has stage IV pancreatic cancer. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating pancreatic cancer (such as metastatic or locally advanced unresectable pancreatic cancer) in an individual comprising: a) selecting the individual for treatment based on the cancer stage of the individual; and b) administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating pancreatic cancer (such as metastatic or locally advanced unresectable pancreatic cancer) in an individual comprising: a) selecting the individual for treatment based on the individual having stage IV pancreatic cancer; and b) administering (for example intravenously) to the individual (i) an effective amount of Nab-paclitaxel (for example about 5 mg/ml Nab-paclitaxel); and (ii) an effective amount of gemcitabine. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating pancreatic cancer (such as metastatic or locally advanced unresectable pancreatic cancer) in an individual comprising: a) determining the stage of the pancreatic cancer in the individual; b) selecting the individual for treatment based on the cancer stage of the individual; and c) administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating pancreatic cancer (such as metastatic or locally advanced unresectable pancreatic cancer) in an individual comprising: a) determining the stage of the pancreatic cancer in the individual; b) selecting the individual for treatment based on the individual having stage IV pancreatic cancer; and c) administering (for example intravenously) to the individual (i) an effective amount of Nab-paclitaxel (for example about 5 mg/ml Nab-paclitaxel); and (ii) an effective amount of gemcitabine. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, the individual is selected for treatment based on the primary location of the pancreatic cancer. In some embodiments, the primary location of the pancreatic cancer is determined by computerized tomography (CT scan), magnetic resonance imaging (MRI scan), positron emission tomography (PET scan), endoscopic retrograde cholangio pancreatography (ERCP), abdominal ultrasound, cholangiogram, chest X-ray, laparoscopy, or by examination (e.g., microscopic examination) of tissue removed during surgery or biopsy.

In some embodiments, there is provided a method of treating pancreatic cancer (such as metastatic or locally advanced unresectable pancreatic cancer) in an individual comprising administering (for example intravenously) to the individual (i) an effective amount of Nab-paclitaxel (for example about 5 mg/ml Nab-paclitaxel); and (ii) an effective amount of gemcitabine, wherein the individual is selected for treatment based on the primary location of the pancreatic cancer. In some embodiments, there is provided a method of treating pancreatic cancer (such as metastatic or locally advanced unresectable pancreatic cancer) in an individual comprising administering (for example intravenously) to the individual (i) an effective amount of Nab-paclitaxel (for example about 5 mg/ml Nab-paclitaxel); and (ii) an effective amount of gemcitabine, wherein the individual is selected for treatment based on the primary location of the cancer being in the head of the pancreas. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating pancreatic cancer (such as metastatic or locally advanced unresectable pancreatic cancer) in an individual comprising: a) determining the primary location of the pancreatic cancer in the individual, and administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating pancreatic cancer (such as metastatic or locally advanced unresectable pancreatic cancer) in an individual comprising: a) determining the primary location of the pancreatic cancer the individual, and administering (for example intravenously) to the individual (i) an effective amount of Nab-paclitaxel (for example about 5 mg/ml Nab-paclitaxel); and (ii) an effective amount of gemcitabine, wherein the individual is selected for treatment if the primary location of the pancreatic cancer is in the head of the pancreas. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating pancreatic cancer (such as metastatic or locally advanced unresectable pancreatic cancer) in an individual comprising: a) selecting the individual for treatment based on the primary location of the pancreatic cancer; and b) administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating pancreatic cancer (such as metastatic or locally advanced unresectable pancreatic cancer) in an individual comprising: a) selecting the individual for treatment based on the primary location of the cancer being in the head of the pancreas; and b) administering (for example intravenously) to the individual (i) an effective amount of Nab-paclitaxel (for example about 5 mg/ml Nab-paclitaxel); and (ii) an effective amount of gemcitabine. In some embodiments, the metastatic pancreatic cancer is metastatic adenocarcinoma of the pancreas.

In some embodiments, there is provided a method of treating pancreatic cancer (such as metastatic or locally advanced unresectable pancreatic cancer) in an individual comprising: a) determining the primary location of the pancreatic cancer; b) selecting the individual for treatment based on the primary location of the pancreatic cancer; and c) administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating pancreatic cancer (such as metastatic or locally advanced unresectable pancreatic cancer) in an individual comprising: a) determining the primary location of the pancreatic cancer; b) selecting the individual for treatment based on the primary location of the cancer being in the head of the pancreas; and c) administering (for example intravenously) to the individual (i) an effective amount of Nab-paclitaxel (for example about 5 mg/ml Nab-paclitaxel); and (ii) an effective amount of gemcitabine. In some embodiments, the metastatic pancreatic cancer is metastatic adenocarcinoma of the pancreas.

In some embodiments, the individual is selected for treatment based on CA19-9 level. In some embodiments, the CA19-9 level is determined via immunoassay, e.g., ELISA or sandwich ELISA. In some embodiments, the individual is treated for at least about 2 months, for example at least about any of 3, 4, 5, 6, 7, 8, 9, 10, 11, 12, or more months.

In some embodiments, there is provided a method of treating pancreatic cancer (such as metastatic or locally advanced unresectable pancreatic cancer) in an individual comprising administering (for example intravenously) to the individual (i) an effective amount of Nab-paclitaxel (for example about 5 mg/ml Nab-paclitaxel); and (ii) an effective amount of gemcitabine, wherein the individual is selected for treatment based on the CA 19-9 level of the individual. In some embodiments, there is provided a method of treating pancreatic cancer (such as metastatic or locally advanced unresectable pancreatic cancer) in an individual comprising administering (for example intravenously) to the individual (i) an effective amount of Nab-paclitaxel (for example about 5 mg/ml Nab-paclitaxel); and (ii) an effective amount of gemcitabine, wherein the individual is selected for treatment based on the individual having CA 19-9 level of ≥59 ULN. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating pancreatic cancer (such as metastatic or locally advanced unresectable pancreatic cancer) in an individual comprising: a) determining the CA 19-9 level of the individual, and administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating pancreatic cancer (such as metastatic or locally advanced unresectable pancreatic cancer) in an individual comprising: a) determining the CA 19-9 level of the individual, and administering (for example intravenously) to the individual (i) an effective amount of Nab-paclitaxel (for example about 5 mg/ml Nab-paclitaxel); and (ii) an effective amount of gemcitabine, wherein the individual is selected for treatment if the individual has CA 19-9 level of ≥59 ULN. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating pancreatic cancer (such as metastatic or locally advanced unresectable pancreatic cancer) in an individual comprising: a) selecting the individual for treatment based on the CA 19-9 level of the individual; and b) administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating pancreatic cancer (such as metastatic or locally advanced unresectable pancreatic cancer) in an individual comprising: a) selecting the individual for treatment based on CA 19-9 level of the individual ≥59 ULN; and b) administering (for example intravenously) to the individual (i) an effective amount of Nab-paclitaxel (for example about 5 mg/ml Nab-paclitaxel); and (ii) an effective amount of gemcitabine. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating pancreatic cancer (such as metastatic or locally advanced unresectable pancreatic cancer) in an individual comprising: a) determining the CA19-9 level of the individual; b) selecting the individual for treatment based on the CA 19-9 level of the individual; and c) administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating pancreatic cancer (such as metastatic or locally advanced unresectable pancreatic cancer) in an individual comprising: a) determining the CA19-9 level of the individual; b) selecting the individual for treatment based on CA 19-9 level of the individual ≥59 ULN; and c) administering (for example intravenously) to the individual (i) an effective amount of Nab-paclitaxel (for example about 5 mg/ml Nab-paclitaxel); and (ii) an effective amount of gemcitabine. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, the individual is selected for treatment based on KPS (Karnofsky Performance Status) of the individual. KPS quantifies cancer patients' general well-being and activities of daily life. This measure is used to determine whether a patient can receive chemotherapy, whether dose adjustment is necessary, and whether the patient is receiving the required intensity of palliative care. In some embodiments, the individual has a KPS between about 90% and about 100%, where the individual is able to carry on normal activity with minor signs or symptoms of the pancreatic cancer. In some embodiments, the individual has a KPS between about 80% and about 90%, where the individual is able to carry on normal activity with effort and has some signs of the pancreatic cancer. In some embodiments, the individual has a KPS between about 80% and about 70%, where the individual can care for him- or herself, but is unable to carry on normal activity or do normal work. In some embodiments, the individual has a KPS of about 60% and about 70%, where the individual requires personal assistance, but is able to care for most of his or her personal needs. In some embodiments, the patient has a KPS between about 50% and 60%, wherein the individual requires considerable assistance and frequent medical care. In some embodiments, the individual has a KPS between about 40% and about 50%, where the individual is disabled and requires special care and assistance. In some embodiments, the individual has a KPS between about 30% and about 40%, where the individual is severely disabled and requires hospital admission although death is not imminent. In some embodiments, the individual has a KPS between about 20% and about 30%, where the patient is very sick and requires hospital admission and active supportive treatment. In some embodiments, the patient has a KPS between about 10% and about 20%, where the patient is moribund and in whom fatal processes are progressing rapidly.

In some embodiments, there is provided a method of treating pancreatic cancer (such as metastatic or locally advanced unresectable pancreatic cancer) in an individual comprising administering (for example intravenously) to the individual (i) an effective amount of Nab-paclitaxel (for example about 5 mg/ml Nab-paclitaxel); and (ii) an effective amount of gemcitabine, wherein the individual is selected for treatment based on the KPS (Karnofsky performance status) of the individual. In some embodiments, there is provided a method of treating pancreatic cancer (such as metastatic or locally advanced unresectable pancreatic cancer) in an individual comprising administering (for example intravenously) to the individual (i) an effective amount of Nab-paclitaxel (for example about 5 mg/ml Nab-paclitaxel); and (ii) an effective amount of gemcitabine, wherein the individual is selected for treatment based on the individual having KPS of less than about 90 (for example about 70-80). In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating pancreatic cancer (such as metastatic or locally advanced unresectable pancreatic cancer) in an individual comprising: a) determining the KPS of the individual, and administering (for example intravenously) to the individual (i) an effective amount of Nab-paclitaxel (for example about 5 mg/ml Nab-paclitaxel); and (ii) an effective amount of gemcitabine. In some embodiments, the metastatic pancreatic cancer is metastatic adenocarcinoma of the pancreas. In some embodiments, there is provided a method of treating pancreatic cancer (such as metastatic or locally advanced unresectable pancreatic cancer) in an individual comprising: a) determining the KPS of the individual, and administering (for example intravenously) to the individual (i) an effective amount of Nab-paclitaxel (for example about 5 mg/ml Nab-paclitaxel); and (ii) an effective amount of gemcitabine, wherein the individual is selected for treatment if the individual has KPS of less than about 90 (for example about 700-80). In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating pancreatic cancer (such as metastatic or locally advanced unresectable pancreatic cancer) in an individual comprising: a) selecting the individual for treatment based on the KPS of the individual; and b) administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating pancreatic cancer (such as metastatic or locally advanced unresectable pancreatic cancer) in an individual comprising: a) selecting the individual for treatment based on t the individual having KPS of less than about 90 (for example about 70-80); and b) administering (for example intravenously) to the individual (i) an effective amount of Nab-paclitaxel (for example about 5 mg/ml Nab-paclitaxel); and (ii) an effective amount of gemcitabine. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating pancreatic cancer (such as metastatic or locally advanced unresectable pancreatic cancer) in an individual comprising: a) determining the KPS of the individual; b) selecting the individual for treatment based on the KPS of the individual; and c) administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating pancreatic cancer (such as metastatic or locally advanced unresectable pancreatic cancer) in an individual comprising: a) determining the KPS of the individual; b) selecting the individual for treatment based on t the individual having KPS of less than about 90 (for example about 70-80); and c) administering (for example intravenously) to the individual (i) an effective amount of Nab-paclitaxel (for example about 5 mg/ml Nab-paclitaxel); and (ii) an effective amount of gemcitabine. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m2 to about 150 mg/m2 (including for example about 75, about 80, or about 100 mg/m2) on days 1, 8, and 15 of each 28 day cycle, and wherein the dose of gemcitabine is about 500 mg/m2 to about 2000 mg/m2 (including for example about 600, about 800, or about 1000 mg/m2) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, the individual is selected for treatment based on hENT1 levels. The methods described herein in some embodiments comprise determining the level of hENT1 (Human Equilibrative Nucleoside Transporter 1) in an individual. In some embodiments, the level is the activity level of hENT1 in a sample, and the activity level can encompass, for example, a measure of the total amount of hydrophilic nucleosides that are moved across the membrane by hENT1 in a cell, a sample, or a tumor. In some embodiments the level is an expression level that correlates to the activity level. In some embodiments the level is a measure of a hENT1 protein present in a cell (for example the surface of a cell), a sample, or a tumor. In some aspects the level is a measure of a nucleic acid present in a cell, a sample, or a tumor. In some embodiments, the level is based on a mutation or polymorphism in the hENT1 gene that correlates with the protein or mRNA level of hENT1. In some embodiments, the level is the protein expression level. In some embodiments, the level is the mRNA level.

The levels of nucleoside transporters such as hENT1 can be determined by methods known in the art. See, for example, Spratlin et al., Cancers 2010, 2, 2044-2054; Santini et al., Current Cancer Drug Targets, 2011, 11, 123-129; Kawada et al. J. Hepatobiliary Pancreat. Sci., 2012, 19:17-722; Morinaga et al., Ann. Surg. Oncol., 2012, 19, S558-S564. See also US Pat. Pub. No. 2013/0005678.

Levels of hENT1 an individual may be determined based on a sample (e.g., sample from the individual or reference sample). In some embodiments, the sample is from a tissue, organ, cell, or tumor. In some embodiments, the sample is a biological sample. In some embodiments, the biological sample is a biological fluid sample or a biological tissue sample. In further embodiments, the biological fluid sample is a bodily fluid. Bodily fluids include, but are not limited to, blood, lymph, saliva, semen, peritoneal fluid, cerebrospinal fluid, breast milk, and pleural effusion. In some embodiments, the sample is a blood sample which includes, for example, platelets, lymphocytes, polymorphonuclear cells, macrophages, and erythrocytes.

In some embodiments, the sample is a tumor tissue, normal tissue adjacent to said tumor, normal tissue distal to said tumor, blood sample, or other biological sample. In some embodiments, the sample is a fixed sample. Fixed samples include, but are not limited to, a formalin fixed sample, a paraffin-embedded sample, or a frozen sample. In some embodiments, the sample is a biopsy containing cancer cells. In a further embodiment, the biopsy is a fine needle aspiration of pancreatic cancer cells. In a further embodiment, the biopsy is laparoscopy obtained pancreatic cancer cells. In some embodiments, the biopsied cells are centrifuged into a pellet, fixed, and embedded in paraffin. In some embodiments, the biopsied cells are flash frozen. In some embodiments, the biopsied cells are mixed with an antibody that recognizes hENT1. In some embodiments, a biopsy is taken to determine whether an individual has cancer and is then used as a sample. In some embodiments, the sample comprises surgically obtained tumor cells. In some embodiments, samples may be obtained at different times than when the determining of hENT1 levels occurs.

In some embodiments, the sample comprises a circulating metastatic pancreatic cancer cell. In some embodiments, the sample is obtained by sorting pancreatic circulating tumor cells (CTCs) from blood. In a further embodiment, the CTCs have detached from a primary tumor and circulate in a bodily fluid. In yet a further embodiment, the CTCs have detached from a primary tumor and circulate in the bloodstream. In a further embodiment, the CTCs are an indication of metastasis.

In some embodiments, the protein expression level of hENT1 is determined. In some embodiments, the mRNA level of the hENT1 is determined. In some embodiments, the level of hENT1 is determined by an immunohistochemistry method.

The level of hENT1 may be a high level or a low level as compared to a control sample. In some embodiments, the level of hENT1 in an individual is compared to the level of hENT1 in a control sample. In some embodiments the level of hENT1 in a subject is compared to the level of hENT1 in multiple control samples. In some embodiments, multiple control samples are used to generate a statistic that is used to classify the level of hENT1in an individual with cancer.

In some embodiments, the DNA copy number is determined, and a high DNA copy number for the gene encoding hENT1 (for example a high DNA copy number as compared to a control sample) is indicative of a high level of hENT1.

The classification or ranking of hENT1 level (i.e., high or low) may be determined relative to a statistical distribution of control levels. In some embodiments, the classification or ranking is relative to a control sample obtained from the individual. In some embodiment the levels of hENT1 is classified or ranked relative to a statistical distribution of control levels. In some embodiments, the level of hENT1 is classified or ranked relative to the level from a control sample obtained from the subject.

Control samples can be obtained using the same sources and methods as non-control samples. In some embodiments, the control sample is obtained from a different individual (for example an individual not having cancer and/or an individual sharing similar ethnic, age, and gender identity). In some embodiments when the sample is a tumor tissue sample, the control sample may be a non-cancerous sample from the same individual. In some embodiments, multiple control samples (for example from different individuals) are used to determine a range of levels of hENT1 in a particular tissue, organ, or cell population. In some embodiments, the control sample is a cultured tissue or cell that has been determined to be a proper control. In some embodiments, the control is a cell that does not express hENT1. In some embodiments, a clinically accepted normal level in a standardized test is used as a control level for determining hENT1 level. In some embodiments, the reference level of hENT1 in the subject is classified as high, medium or low according to a scoring system, such as an immunohistochemistry-based scoring system, for example an H-Score as further discussed herein. In some embodiments, the reference level of hENT1 in the subject is classified as a low sample when the H-Score is less than or equal to the overall median H-Score.

In some embodiments, the hENT1 level is determined by measuring the level hENT1 in an individual and comparing to a control or reference (e.g., the median level for the given patient population or level of a second individual). For example, if the level of hENT1 for the single individual is determined to be above the median level of the patient population, that individual is determined to have high expression of hENT1. Alternatively, if the level of hENT1 for the single individual is determined to be below the median level of the patient population, that individual is determined to have low expression of the hENT1. In some embodiments, the individual is compared to a second individual and/or a patient population which is responsive to treatment. In some embodiments, the individual is compared to a second individual and/or a patient population which is not responsive to treatment. In any of the embodiments herein, the levels are determined by measuring the level of a nucleic acid encoding hENT1. For example, if the level of an mRNA encoding hENT1 for the single individual is determined to be above the median level of the patient population, that individual is determined to have a high level of an mRNA encoding hENT1. Alternatively, if the level of mRNA encoding hENT1 for the single individual is determined to be below the median level of the patient population, that individual is determined to have a low level of an mRNA encoding hENT1.

In some embodiments, the reference level of hENT1 is determined by obtaining a statistical distribution of hENT1 levels.

In some embodiments, hENT1 mRNA level is determined, and a low level is an mRNA level less than about 1.1, 1.2, 1.3, 1.5, 1.7, 2, 2.2, 2.5, 2.7, 3, 5, 7, 10, 20, 50, 70, 100, 200, 500, 1000 times or less than 1000 times to that of what is considered as clinically normal or to the level obtained from a control. In some embodiments, high level is an mRNA level more than about 1.1, 1.2, 1.3, 1.5, 1.7, 2, 2.2, 2.5, 2.7, 3, 5, 7, 10, 20, 50, 70, 100, 200, 500, 1000 times or more than 1000 times to that of what is considered as clinically normal or to the level obtained from a control.

In some embodiments, hENT1 protein expression level is determined, for example by immunohistochemistry. For example, the criteria for low or high levels can be made based on the number of positive staining cells and/or the intensity of the staining, for example by using an antibody that specifically recognizes the hENT1 protein. In some embodiments, the hENT1 level is low if less than about 1%, 5%, 10%, 15%, 20%, 25%, 30%, 35%, 40%, 45%, or 50% cells have positive staining. In some embodiments, the hENT1 level is low if the staining is 1%, 5%, 10%, 15%, 20%, 25%, 30%, 35%, 40%, 45%, or 50% less intense than a positive control staining.

In some embodiments, the hENT1 level is high if more than about 40%, 45%, 50%, 55%, 60%, 65%, 70%, 75%, 80%, 85%, or 90%, cells have positive staining. In some embodiments, the hENT1 level is high if the staining is as intense as positive control staining. In some embodiments, the hENT1 level is high if the staining is 80%, 85%, or 90% as intense as positive control staining.

In some embodiments, the scoring is based on an "H-score" as described in US Pat. Pub. No. 2013/0005678. An H-score is obtained by the formula: 3×percentage of strongly staining cells+2×percentage of moderately staining cells+percentage of weakly staining cells, giving a range of 0 to 300.

In some embodiments, strong staining, moderate staining, and weak staining are calibrated levels of staining, wherein a range is established and the intensity of staining is binned within the range. In some embodiments, strong staining is staining above the 75th percentile of the intensity range, moderate staining is staining from the 25th to the 75th percentile of the intensity range, and low staining is staining is staining below the 25th percentile of the intensity range. In some aspects one skilled in the art, and familiar with a particular staining technique, adjusts the bin size and defines the staining categories.

In some embodiments, the label high hENT1 staining is assigned where greater than 50% of the cells stained exhibited strong reactivity, the label no hENT1 staining is assigned where no staining was observed in less than 50% of the cells stained, and the label low hENT1 staining is assigned for all of other cases.

In some embodiments, the assessment and scoring of the hENT1 level in a sample, patient, etc., is performed by one or more experienced clinicians, i.e., those who are experienced with hENT1 expression and hENT1 staining patterns. For example, in some embodiments, the clinician(s) is blinded to clinical characteristics and outcome for the samples, patients, etc. being assessed and scored.

In some embodiments, there is provided a method of treating pancreatic cancer (such as metastatic or locally advanced unresectable pancreatic cancer) in an individual comprising administering (for example intravenously) to the individual (i) an effective amount of Nab-paclitaxel (for example about 5 mg/ml Nab-paclitaxel); and (ii) an effective amount of gemcitabine, wherein the individual is selected for treatment based on the hENT1 level (such as hENT1 expression level) of the individual. In some embodiments, there is provided a method of treating pancreatic cancer (such as metastatic or locally advanced unresectable pancreatic cancer) in an individual comprising: a) determining the hENT1 level (such as hENT1 expression level) of the individual, and administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating pancreatic cancer (such as metastatic or locally advanced unresectable pancreatic cancer) in an individual comprising: a) selecting the individual for treatment based on the hENT1 level (such as hENT1 expression level) of the individual; and b) administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating pancreatic cancer (such as metastatic or locally advanced unresectable pancreatic cancer) in an individual comprising: a) determining the hENT1 level (such as hENT1 expression level) of the individual b) selecting the individual for treatment based on the hENT1 level (such as hENT1 expression level) of the individual; and c) administering (for example intravenously) to the individual (i) an effective amount of Nab-paclitaxel (for example about 5 mg/ml Nab-paclitaxel); and (ii) an effective amount of gemcitabine. In some embodiments, the individual having a high hENT1 level (such as hENT1 expression level) is treated. In some embodiments, the individual having a low hENT1 level (such as hENT1 expression level) is treated. High or low hENT1 level (such as hENT1 expression level) can be determined by methods known in the art, for example immunohistochemistry assays. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, there is provided a method of treating pancreatic cancer (such as metastatic or locally advanced unresectable pancreatic cancer) in an individual comprising administering (for example intravenously) to the individual (i) an effective amount of Nab-paclitaxel (for example about 5 mg/ml Nab-paclitaxel); and (ii) an effective amount of gemcitabine, wherein the individual is selected for treatment based on the individual having a high hENT1 level (such as hENT1 expression level). In some embodiments, there is provided a method of treating pancreatic cancer (such as metastatic or locally advanced unresectable pancreatic cancer) in an individual comprising: a) determining the hENT1 level (such as hENT1 expression level) of the individual, and administering (for example intravenously) to the individual (i) an effective amount of Nab-paclitaxel (for example about 5 mg/ml Nab-paclitaxel); and (ii) an effective amount of gemcitabine, wherein the individual is selected for treatment if the individual having a high hENT1 level (such as hENT1 expression level). In some embodiments, there is provided a method of treating pancreatic cancer (such as metastatic or locally advanced unresectable pancreatic cancer) in an individual comprising: a) selecting the individual for treatment based on the individual having a high hENT1 level (such as hENT1 expression level); and b) administering (for example intravenously) to the individual (i) an effective amount of Nab-paclitaxel (for example about 5 mg/ml Nab-paclitaxel); and (ii) an effective amount of gemcitabine. In some embodiments, there is provided a method of treating pancreatic cancer (such as metastatic or locally advanced unresectable pancreatic cancer) in an individual comprising: a) determining the hENT1 level (such as hENT1 expression level) of the individual; b) selecting the individual for treatment based on the individual having a high hENT1 level (such as hENT1 expression level); and c) administering (for example intravenously) to the individual (i) an effective amount of Nab-paclitaxel (for example about 5 mg/ml Nab-paclitaxel); and (ii) an effective amount of gemcitabine. In some embodiments, the metastatic pancreatic cancer is metastatic adenocarcinoma of the pancreas. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

In some embodiments, the selection of the individual is based on at least 2, 3, 4, 5, or more characteristics described herein. Thus, for example, the methods may comprise selecting an individual based on (i) having 3 or more metastatic sites, (ii) having metastasis in the liver, (iii) having pancreatic cancer at the primary location in the head of the pancreas; and/or (iv) having CA19-9 level of ≥59 UNL. In some embodiments, the methods comprise determining the metastatic status, the primary location, and/or the CA19-9 level in the individual, wherein the individual is selected for treatment if the individual (i) has 3 or more metastatic sites, (ii) has metastasis in the liver, (iii) has pancreatic cancer at the primary location in the head of the pancreas; and/or (iv) hasCA19-9 level of ≥59 UNL. In some embodiments, the individual is assessed (or further assessed) for KPS and/or hENT1 level, wherein the individual is selected for treatment if the individual: (i) has KPS of less than about 90 (for example about 70-80), and/or (ii) has high hENT1 level (such as hENT1 expression level). Other combinations of the various characteristics are also contemplated. In some embodiments, the method comprises intravenously administering to the individual (i) an effective amount of Nab-paclitaxel (for example about 5 mg/ml Nab-paclitaxel); and (ii) an effective amount of gemcitabine, wherein the dose of paclitaxel in the nanoparticle composition is about 50 mg/m$^2$ to about 150 mg/m$^2$ (including for example about 75, about 80, or about 100 mg/m$^2$) on days 1, 8, and 15 of each 28 day cycle, and wherein the dose of gemcitabine is about 500 mg/m$^2$ to about 2000 mg/m$^2$ (including for example about 600, about 800, or about 1000 mg/m$^2$) on days 1, 8, and 15 of each 28 day cycle. In some embodiments, the individual is treated for at least about 2 months, for example at least about any of 3, 4, 5, 6, 7, 8, 9, 10, 11, 12, or more months.

Modes of Administration

The dose of the taxane (such as paclitaxel) nanoparticle compositions and/or the dose of gemcitabine administered to an individual (such as a human) according to (or as applied to) a method described herein may vary with the particular composition, the mode of administration, and the type of pancreatic cancer described herein being treated. The dose of the taxane (such as paclitaxel) nanoparticle compositions and/or the dose of gemcitabine administered to an individual (such as a human) may also be adjusted (such as reduced) based on an individual's symptoms (such as adverse reactions). In some embodiments, the dose or amount is effective to result in a response. In some embodiments, the dose or amount is effective to result in an objective response (such as a partial response or a complete response). In some embodiments, the dose of the taxane (such as paclitaxel) nanoparticle composition (and/or the dose of gemcitabine) administered is sufficient to produce an overall response rate of more than about any of 20%, 25%, 30%, 35%, 40%, 45%, 50%, 55%, 60%, 64%, 65%, 70%, 75%, 80%, 85%, or 90% among a population of individuals treated with the taxane (such as paclitaxel) nanoparticle composition and/or gemcitabine. Responses of an individual to the treatment of the methods described herein can be determined using methods known in the field.

In some embodiments, the amount of the taxane (such as paclitaxel) nanoparticle composition and/or the amount of gemcitabine are sufficient to prolong progression-free survival of the individual. In some embodiments, the amount of the composition (and/or the dose of gemcitabine) is sufficient to prolong survival of the individual. In some embodiments, the amount of the composition (and/or the dose of gemcitabine) is sufficient to improve quality of life of the individual. In some embodiments, the amount of the composition (and/or the dose of gemcitabine) is sufficient to produce clinical benefit of more than about any of 50%, 60%, 70%, or 77% among a population of individuals treated with the taxane (such as paclitaxel) nanoparticle composition and/or gemcitabine.

In some embodiments, the amount of the taxane (such as paclitaxel) nanoparticle composition, or gemcitabine is an amount sufficient to decrease the size of a pancreatic tumor, decrease the number of pancreatic tumor cells, or decrease the growth rate of a pancreatic tumor by at least about any of 10%, 20%, 30%, 40%, 50%, 60%, 70%, 80%, 90%, 95% or 100% compared to the corresponding tumor size, number of pancreatic tumor cells, or tumor growth rate in the same individual prior to treatment or compared to the corresponding activity in other individuals not receiving the treatment. Methods that can be used to measure the magnitude of this effect are known in the field.

In some embodiments, the amount of the taxane (e.g., paclitaxel) in the composition (and/or gemcitabine) is below the level that induces a toxicological effect (i.e., an effect above a clinically acceptable level of toxicity) or is at a level where a potential side effect can be controlled or tolerated when the composition (and/or gemcitabine) is administered to the individual.

In some embodiments, the amount of the composition (and/or gemcitabine) is close to a maximum tolerated dose (MTD) of the composition (and/or gemcitabine) following the same dosing regimen. In some embodiments, the amount of the composition (and/or gemcitabine) is more than about any of 80%, 90%, 95%, or 98% of the MTD.

In some embodiments, the amount (dose) of a taxane (e.g., paclitaxel) in the composition is included in any of the following ranges: about 0.1 mg to about 500 mg, about 0.1 mg to about 2.5 mg, about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount (dose) of a taxane (e.g., paclitaxel) in the composition (e.g., a unit dosage form) is in the range of about 5 mg to about 500 mg, such as about 30 mg to about 300 mg or about 50 mg to about 200 mg. In some embodiments, the concentration of the taxane (e.g., paclitaxel) in the composition is dilute (about 0.1 mg/ml) or concentrated (about 100 mg/ml), including for example any of about 0.1 to about 50 mg/ml, about 0.1 to about 20 mg/ml, about 1 to about 10 mg/ml, about 2 mg/ml to about 8 mg/ml, about 4 to about 6 mg/ml, or about 5 mg/ml. In some embodiments, the concentration of the taxane (e.g., paclitaxel) is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml. In some embodiments, the concentration of the taxane (e.g., paclitaxel) is no more than about any of 100 mg/ml, 90 mg/ml, 80 mg/ml, 70 mg/ml, 60 mg/ml, 50 mg/ml, 40 mg/ml, 30 mg/ml, 20 mg/ml, 10 mg/ml, or 5 mg/ml.

Exemplary amounts (doses) of a taxane (e.g., paclitaxel) in the nanoparticle composition include, but are not limited to, at least about any of 25 mg/m$^2$, 30 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 125 mg/m$^2$, 150 mg/m$^2$, 160 mg/m$^2$, 175 mg/m$^2$, 180 mg/m$^2$, 200 mg/m$^2$, 210 mg/m$^2$, 220 mg/m$^2$, 250 mg/m$^2$, 260 mg/m$^2$, 300 mg/m$^2$, 350 mg/m$^2$, 400 mg/m$^2$, 500 mg/m$^2$, 540 mg/m$^2$, 750 mg/m$^2$, 1000 mg/m$^2$, or 1080 mg/m$^2$ of a taxane (e.g., paclitaxel). In various embodiments, the composition includes less than about any of 350 mg/m$^2$, 300 mg/m$^2$, 250 mg/m$^2$, 200 mg/m$^2$, 150 mg/m$^2$, 120 mg/m$^2$, 100 mg/m$^2$, 90 mg/m$^2$, 50 mg/m$^2$, or 30 mg/m$^2$ of a taxane (e.g., paclitaxel). In some embodiments, the amount of the taxane (e.g., paclitaxel) per administration is less than about any of 25 mg/m$^2$, 22 mg/m$^2$, 20 mg/m$^2$, 18 mg/m$^2$, 15 mg/m$^2$, 14 mg/m$^2$, 13 mg/m$^2$, 12 mg/m$^2$, 11 mg/m$^2$, 10 mg/m$^2$, 9 mg/m$^2$, 8 mg/m$^2$, 7 mg/m$^2$, 6 mg/m$^2$, 5 mg/m$^2$, 4 mg/m$^2$, 3 mg/m$^2$, 2 mg/m$^2$, or 1 mg/m$^2$. In some embodiments, the amount (dose) of a taxane (e.g., paclitaxel) in the composition is included in any of the following ranges: about 1 to about 5 mg/m$^2$, about 5 to about 10 mg/m$^2$, about 10 to about 25 mg/m$^2$, about 25 to about 50 mg/m$^2$, about 50 to about 75 mg/m$^2$, about 75 to about 100 mg/m$^2$, about 100 to about 125 mg/m$^2$, about 125 to about 150 mg/m$^2$, about 125 to about 175 mg/m$^2$, about 150 to about 175 mg/m$^2$, about 175 to about 200 mg/m$^2$, about 200 to about 225 mg/m$^2$, about 225 to about 250 mg/m$^2$, about 250 to about 300 mg/m$^2$, about 300 to about 350 mg/m$^2$, or about 350 to about 400 mg/m$^2$. In some embodiments, the effective amount of a taxane (e.g., paclitaxel) in the composition is included in any of the following ranges: about 10 mg/m$^2$ to about 400 mg/m$^2$, about 25 mg/m$^2$ to about 400 mg/m$^2$, about 50 mg/m$^2$ to about 400 mg/m$^2$, about 75 mg/m$^2$ to about 350 mg/m$^2$, about 75 mg/m$^2$ to about 300 mg/m$^2$, about 75 mg/m$^2$ to about 250 mg/m$^2$, about 75 mg/m$^2$ to about 200 mg/m$^2$, about 75 mg/m$^2$ to about 150 mg/m$^2$, about 75 mg/m$^2$ to about 125 mg/m$^2$, about 100 mg/m$^2$ to about 260 mg/m$^2$, about 100 mg/m$^2$ to about 250 mg/m$^2$, about 100 mg/m$^2$ to about 200 mg/m$^2$, or about 125 mg/m$^2$ to about 175 mg/m$^2$. In some embodiments, the amount (dose) of a taxane (e.g., paclitaxel) in the composition is about 5 to about 300 mg/m$^2$, about 100 to about 200 mg/m$^2$, about 100 to about 150 mg/m$^2$, about 50 to about 150 mg/m$^2$, about 75 to about 150 mg/m$^2$, about 75 to about 125 mg/m$^2$, or about 70 mg/m$^2$, about 80 mg/m$^2$, about 90 mg/m$^2$, about 100 mg/m$^2$, about 110 mg/m$^2$, about 120 mg/m$^2$, about 130 mg/m$^2$, about 140 mg/m$^2$, about 150 mg/m$^2$, about 160 mg/m$^2$, about 170 mg/m$^2$, about 180 mg/m$^2$, about 190 mg/m$^2$, about 200 mg/m$^2$, about 250 mg/m$^2$, about 260 mg/m$^2$, or about 300 mg/m$^2$.

In some embodiments of any of the above aspects, the amount (dose) of a taxane (e.g., paclitaxel) in the composition includes at least about any of 1 mg/kg, 2.5 mg/kg, 3.5 mg/kg, 5 mg/kg, 6.5 mg/kg, 7.5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, or 60 mg/kg. In various embodiments, the amount (dose) of a taxane (e.g., paclitaxel) in the composition includes less than about any of 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 7.5 mg/kg, 6.5 mg/kg, 5 mg/kg, 3.5 mg/kg, 2.5 mg/kg, or 1 mg/kg of a taxane (e.g., paclitaxel).

Exemplary dosing frequencies for the administration of the nanoparticle compositions include, but are not limited to, daily, every two days, every three days, every four days, every five days, every six days, weekly without break, weekly for three out of four weeks, once every three weeks, once every two weeks, or two out of three weeks. In some embodiments, the composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 14 days, 13 days, 12 days, 11 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

In some embodiments, the dosing frequency is once every two days for one time, two times, three times, four times, five times, six times, seven times, eight times, nine times, ten times, and eleven times. In some embodiments, the dosing frequency is once every two days for five times. In some embodiments, the taxane (e.g., paclitaxel) is administered over a period of at least ten days, wherein the interval between each administration is no more than about two days, and wherein the dose of the taxane (e.g., paclitaxel) at each administration is about 0.25 mg/m$^2$ to about 250 mg/m$^2$, about 0.25 mg/m$^2$ to about 150 mg/m$^2$, about 0.25 mg/m$^2$ to about 75 mg/m$^2$, such as about 0.25 mg/m$^2$ to about 25 mg/m$^2$, about 25 mg/m$^2$ to about 50 mg/m$^2$, or about 50 mg/m$^2$ to about 100 mg/m$^2$.

The administration of the composition can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months.

In some embodiments, the dosage of a taxane (e.g., paclitaxel) in a nanoparticle composition can be in the range of 5-400 mg/m$^2$ when given on a 3 week schedule, or 5-250 mg/m$^2$ (such as 75-200 mg/m$^2$, 100-200 mg/m$^2$, for example 125-175 mg/m$^2$) when given on a weekly schedule. For example, the amount of a taxane (e.g., paclitaxel) is about 60 to about 300 mg/m$^2$ (e.g., about 100 mg/m$^2$, 125 mg/m$^2$, 150 mg/m$^2$, 175 mg/m$^2$, 200 mg/m$^2$, 225 mg/m$^2$, 250 mg/m$^2$, or 260 mg/m$^2$) on a three week schedule. In some embodiments, the amount of a taxane (e.g., paclitaxel) is about 60 to about 300 mg/m$^2$ (e.g., about 100 mg/m$^2$, 125 mg/m$^2$, 150 mg/m$^2$, 175 mg/m$^2$, 200 mg/m$^2$, 225 mg/m$^2$, 250 mg/m$^2$, or 260 mg/m$^2$) administered weekly. In some embodiments, the amount of a taxane (e.g., paclitaxel) is about 60 to about 300 mg/m$^2$ (e.g., about 100 mg/m$^2$, 125 mg/m$^2$, 150 mg/m$^2$, 175 mg/m$^2$, 200 mg/m$^2$, 225 mg/m$^2$, 250 mg/m$^2$, or 260 mg/m$^2$) administered weekly for three out of a four week schedule.

Other exemplary dosing schedules for the administration of the nanoparticle composition (e.g., paclitaxel/albumin nanoparticle composition) include, but are not limited to, 100 mg/m$^2$, weekly, without break; 75 mg/m$^2$ weekly, 3 out of four weeks; 100 mg/m2, weekly, 3 out of 4 weeks; 125 mg/m$^2$, weekly, 3 out of 4 weeks; 150 mg/m$^2$, weekly, 3 out of 4 weeks; 175 mg/m$^2$, weekly, 3 out of 4 weeks; 125 mg/m$^2$, weekly, 2 out of 3 weeks; 130 mg/m$^2$, weekly, without break; 175 mg/m$^2$, once every 2 weeks; 260 mg/m$^2$, once every 2 weeks; 260 mg/m$^2$, once every 3 weeks; 180-300 mg/m$^2$, every three weeks; 60-175 mg/m$^2$, weekly, without break; 20-150 mg/m$^2$ twice a week; 150-250 mg/m$^2$ twice a week; 50-70 mg/m$^2$ twice a week; 50-70 mg/m$^2$ three times a week; and 30-70 mg/m$^2$ daily. The dosing frequency of the composition may be adjusted over the course of the treatment based on the judgment of the administering physician.

In some embodiments, the individual is treated for at least about any of one, two, three, four, five, six, seven, eight, nine, or ten treatment cycles.

The compositions described herein allow infusion of the composition to an individual over an infusion time that is shorter than about 24 hours. For example, in some embodiments, the composition is administered over an infusion period of no greater than (such as less than) about any of 24 hours, 12 hours, 8 hours, 5 hours, 3 hours, 2 hours, 1 hour, 50 minutes, 40 minutes, 30 minutes, 20 minutes, or 10 minutes. In some embodiments, the composition is administered over an infusion period of about 30 minutes. In some embodiments, the composition is administered over an infusion period of about 30-40 minutes.

Other exemplary doses of the taxane (in some embodiments paclitaxel) in the nanoparticle composition include, but are not limited to, about any of 50 mg/m$^2$, 60 mg/m$^2$, 75 mg/m$^2$, 80 mg/m$^2$, 90 mg/m$^2$, 100 mg/m$^2$, 120 mg/m$^2$, 140 mg/m$^2$, 150 mg/m$^2$, 160 mg/m$^2$, 175 mg/m$^2$, 200 mg/m$^2$, 210 mg/m$^2$, 220 mg/m$^2$, 260 mg/m$^2$, and 300 mg/m$^2$. For example, the dosage of paclitaxel in a nanoparticle composition can be in the range of about 100-400 mg/m$^2$ when given on a 3 week schedule, or about 50-250 mg/m$^2$ when given on a weekly schedule.

Gemcitabine administered to an individual according to (or as applied to) a method described herein may be in the range of about 100 mg/m$^2$ to about 5000 mg/m$^2$, about 100 mg/m$^2$ to about 2000 mg/m$^2$, about 200 to about 4000 mg/m$^2$, about 300 to about 3000 mg/m$^2$, about 400 to about 2000 mg/m$^2$, about 500 to about 1500 mg/m$^2$, about 500 mg/m$^2$ to about 2000 mg/m$^2$ about 750 to about 1500 mg/m$^2$, about 800 to about 1500 mg/m$^2$, about 900 to about 1400 mg/m$^2$, about 900 to about 1250 mg/m$^2$, about 1000 to about 1500 mg/m$^2$, about 800 mg/m$^2$, about 850 mg/m$^2$, about 900 mg/m$^2$, about 950 mg/m$^2$, about 1000 mg/m$^2$, about 1050 mg/m$^2$, about 1100 mg/m$^2$, about 1150 mg/m$^2$, about 1200 mg/m$^2$, about 1250 mg/m$^2$, about 1300 mg/m$^2$, about 1350 mg/m$^2$, about 1400 mg/m$^2$, about 1450 mg/m$^2$, 1500 mg/m$^2$, 1550 mg/m$^2$, 1600 mg/m$^2$, 1700 mg/m$^2$, 1800 mg/m$^2$, 1900 mg/m$^2$, or 2000 mg/m$^2$. Gemcitabine may be administered by intravenous (IV) infusion, e.g., over a period of about 10 to about 300 minutes, about 15 to about 180 minutes, about 20 to about 60 minutes, about 10 minutes, about 20 minutes, or about 30 minutes.

Exemplary dosing frequencies for the administration of gemcitabine include, but are not limited to, daily, every two days, every three days, every four days, every five days, every six days, weekly without break, weekly for three out of four weeks, once every three weeks, once every two weeks, or two out of three weeks. In some embodiments, gemcitabine is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 14 days, 13 days, 12 days, 11 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

In some embodiments, the dosing frequency is once every two days for one time, two times, three times, four times, five times, six times, seven times, eight times, nine times, ten times, and eleven times. In some embodiments, the dosing frequency is once every two days for five times. In some embodiments, gemcitabine is administered over a period of at least ten days, wherein the interval between each administration is no more than about two days, and wherein the dose of the gemcitabine at each administration is about 0.25 mg/m$^2$ to about 1500 mg/m$^2$, about 10 mg/m$^2$ to about 1000 mg/m$^2$, about 25 mg/m$^2$ to about 750 mg/m$^2$, such as about 25 mg/m$^2$ to about 500 mg/m$^2$, about 25 mg/m$^2$ to about 250 mg/m$^2$, or about 25 mg/m$^2$ to about 100 mg/m$^2$.

Other exemplary amounts of gemcitabine include, but are not limited to, any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, about 450 to about 500 mg, about 500 to about 600 mg, about 600 to about 700 mg, about 700 to about 800 mg, about 800 to about 900 mg, about 900 to about 1000 mg, about 1000 to about 1250 mg, or about 1250 to about 1500 mg.

The administration of gemcitabine can be extended over an extended period of time, such as from about a month up to about seven years. In some embodiments, gemcitabine is administered over a period of at least about any of 2, 3, 4, 5, 6, 7, 8, 9, 10, 11, 12, 18, 24, 30, 36, 48, 60, 72, or 84 months.

The composition comprising nanoparticles comprising a taxane (such as paclitaxel) (also referred to as "nanoparticle composition") and gemcitabine can be administered simultaneously (i.e., simultaneous administration) and/or sequentially (i.e., sequential administration).

In some embodiments, the nanoparticle composition and gemcitabine are administered simultaneously. The term "simultaneous administration," as used herein, means that the nanoparticle composition and the other agent are administered with a time separation of no more than about 15 minute(s), such as no more than about any of 10, 5, or 1 minutes. When the drugs are administered simultaneously, the drug in the nanoparticles and the other agent may be contained in the same composition (e.g., a composition comprising both the nanoparticles and the other agent) or in separate compositions (e.g., the nanoparticles are contained in one composition and the other agent is contained in another composition).

In some embodiments, the nanoparticle composition and gemcitabine are administered sequentially. The term "sequential administration" as used herein means that the drug in the nanoparticle composition and the other agent are administered with a time separation of more than about 15 minutes, such as more than about any of 20, 30, 40, 50, 60 or more minutes. Either the nanoparticle composition or gemcitabine may be administered first. In some embodiments, gemcitabine is administered immediately after the completion of the administration of the nanoparticle composition. The nanoparticle composition and gemcitabine are contained in separate compositions, which may be contained in the same or different packages.

In some embodiments, the administration of the nanoparticle composition and gemcitabine are concurrent, i.e., the administration period of the nanoparticle composition and that of gemcitabine overlap with each other. In some embodiments, the nanoparticle composition is administered for at least one cycle (for example, at least any of 2, 3, or 4 cycles) prior to the administration of gemcitabine. In some embodiments, gemcitabine is administered for at least any of one, two, three, or four weeks. In some embodiments, the administrations of the nanoparticle composition and gemcitabine are initiated at about the same time (for example, within any one of 1, 2, 3, 4, 5, 6, or 7 days). In some embodiments, the administrations of the nanoparticle composition and gemcitabine are terminated at about the same time (for example, within any one of 1, 2, 3, 4, 5, 6, or 7 days). In some embodiments, the administration of gemcitabine continues (for example for about any one of 1, 2, 3, 4, 5, 6, 7, 8, 9, 10, 11, or 12 months) after the termination of the administration of the nanoparticle composition. In some embodiments, the administration of gemcitabine is initiated after (for example after about any one of 1, 2, 3, 4, 5, 6, 7, 8, 9, 10, 11, or 12 months) the initiation of the administration of the nanoparticle composition. In some embodiments, the administrations of the nanoparticle composition and gemcitabine are initiated and terminated at about the same time. In some embodiments, the administrations of the nanoparticle composition and gemcitabine are initiated at about the same time and the administration of gemcitabine continues (for example for about any one of 1, 2, 3, 4, 5, 6, 7, 8, 9, 10, 11, or 12 months) after the termination of the administration of the nanoparticle composition. In some embodiments, the administration of the nanoparticle composition and gemcitabine stop at about the same time and the administration of gemcitabine is initiated after (for example after about any one of 1, 2, 3, 4, 5, 6, 7, 8, 9, 10, 11, or 12 months) the initiation of the administration of the nanoparticle composition.

In some embodiments, the method comprises more than one treatment cycle, wherein at least one of the treatment cycles comprises the administration of (i) an effective amount of a composition comprising nanoparticles comprising a taxane (such as paclitaxel) and a carrier protein (e.g., an albumin); and (ii) an effective amount of gemcitabine. In some embodiments, the treatment cycle comprises no less than about (such as about) 21 days (e.g., 4 weeks). In some embodiments, the treatment cycle comprises less than about 21 days (for example weekly or daily). In some embodiments, the treatment cycle comprises about 28 days.

In some embodiments, the administration of the nanoparticle composition and gemcitabine are non-concurrent. For example, in some embodiments, the administration of the nanoparticle composition is terminated before gemcitabine is administered. In some embodiments, the administration of gemcitabine is terminated before the nanoparticle composition is administered. The time period between these two non-concurrent administrations can range from about two to eight weeks, such as about four weeks.

The dosing frequency of the drug-containing nanoparticle composition and gemcitabine may be adjusted over the course of the treatment, based on the judgment of the administering physician. When administered separately, the drug-containing nanoparticle composition and gemcitabine can be administered at different dosing frequency or intervals. For example, the drug-containing nanoparticle composition can be administered weekly, while gemcitabine can be administered more or less frequently. In some embodiments, sustained continuous release formulation of the drug-containing nanoparticle and/or gemcitabine may be used. Various formulations and devices for achieving sustained release are known in the art. Exemplary dosing frequencies are further provided herein.

The nanoparticle composition and gemcitabine can be administered using the same route of administration or different routes of administration. Exemplary administration routes are further provided herein. In some embodiments (for both simultaneous and sequential administrations), the taxane (such as paclitaxel) in the nanoparticle composition and gemcitabine are administered at a predetermined ratio. For example, in some embodiments, the ratio by weight of the taxane (such as paclitaxel) in the nanoparticle composition and gemcitabine is about 1 to 1. In some embodiments, the weight ratio may be between about 0.001 to about 1 and about 1000 to about 1, or between about 0.01 to about 1 and 100 to about 1. In some embodiments, the ratio by weight of the taxane (such as paclitaxel) in the nanoparticle composition and gemcitabine is less than about any of 100:1, 50:1, 30:1, 10:1, 9:1, 8:1, 7:1, 6:1, 5:1, 4:1, 3:1, 2:1, and 1:1

In some embodiments, the ratio by weight of the taxane (such as paclitaxel) in the nanoparticle composition and gemcitabine is more than about any of 1:1, 2:1, 3:1, 4:1, 5:1, 6:1, 7:1, 8:1, 9:1, 30:1, 50:1, 100:1. Other ratios are contemplated.

The doses required for the taxane (such as paclitaxel) and/or gemcitabine may be lower than what is normally required when each agent is administered alone. Thus, in some embodiments, a subtherapeutic amount of the drug in the nanoparticle composition and/or gemcitabine are administered. "Subtherapeutic amount" or "subtherapeutic level" refer to an amount that is less than therapeutic amount, that is, less than the amount normally used when the drug in the nanoparticle composition and/or gemcitabine are administered alone. The reduction may be reflected in terms of the amount administered at a given administration and/or the amount administered over a given period of time (reduced frequency).

In some embodiments, enough gemcitabine is administered so as to allow reduction of the normal dose of the drug in the nanoparticle composition required to effect the same degree of treatment by at least about any of 5%, 10%, 20%, 30%, 50%, 60%, 70%, 80%, 90%, or more. In some embodiments, enough taxane (such as paclitaxel) in the nanoparticle composition is administered so as to allow reduction of the normal dose of gemcitabine required to effect the same degree of treatment by at least about any of 5%, 10%, 20%, 30%, 50%, 60%, 70%, 80%, 90%, or more.

In some embodiments, the dose of both the taxane (such as paclitaxel) in the nanoparticle composition and gemcitabine are reduced as compared to the corresponding normal dose of each when administered alone. In some embodiments, both the taxane (such as paclitaxel) in the nanoparticle composition and gemcitabine are administered at a subtherapeutic, i.e., reduced, level. In some embodiments, the dose of the nanoparticle composition and/or gemcitabine is substantially less than the established maximum toxic dose (MTD). For example, the dose of the nanoparticle composition and/or gemcitabine is less than about 50%, 40%, 30%, 20%, or 10% of the MTD.

In some embodiments, the dose of taxane (such as paclitaxel) and/or the dose of gemcitabine is higher than what is normally required when each agent is administered alone. For example, in some embodiments, the dose of the nanoparticle composition and/or gemcitabine is substantially higher than the established maximum toxic dose (MTD). For example, the dose of the nanoparticle composition and/or gemcitabine is more than about 50%, 40%, 30%, 20%, or 10% of the MTD of the agent when administered alone.

As will be understood by those of ordinary skill in the art, the appropriate doses of gemcitabine will be approximately those already employed in clinical therapies wherein the gemcitabine is administered alone or in combination with other agents. Variation in dosage will likely occur depending on the condition being treated. As described above, in some embodiments, gemcitabine may be administered at a reduced level.

The nanoparticle compositions and/or gemcitabine can be administered to an individual (such as human) via various routes, including, for example, parenteral, intravenous, intraventricular, intra-arterial, intraperitoneal, intrapulmonary, oral, inhalation, intravesicular, intramuscular, intratracheal, subcutaneous, intraocular, intrathecal, transmucosal, and transdermal. In some embodiments, sustained continuous release formulation of the composition and/or gemcitabine may be used. In some embodiments, the composition (and/or gemcitabine) is administered intravenously. In some embodiments, the composition (and/or gemcitabine) is administered intraportally. In some embodiments, the composition (and/or gemcitabine) is administered intraarterially. In some embodiments, the composition (and/or gemcitabine) is administered intraperitoneally. In some embodiments, the composition (and/or gemcitabine) is administered intrathecally. In some embodiments, the composition (and/or gemcitabine) is administered through a ported catheter to spinal fluid. In some embodiments, the composition (and/or gemcitabine) is administered intraventricularly. In some embodiments, the composition (and/or gemcitabine) is administered systemically. In some embodiments, the composition (and/or gemcitabine) is administered by infusion. In some embodiments, the composition (and/or gemcitabine) is administered by infusion through implanted pump. In some embodiments, the composition (and/or gemcitabine) is administered by a ventricular catheter. In some embodiments, the composition (and/or gemcitabine) is administered through a port or portacath. In some embodiments, the port or portacath is inserted into a vein (such as jugular vein, subclavian vein, or superior vena cava).

In some embodiments, there is provided a method of treating pancreatic cancer (e.g., metastatic pancreatic adenocarcinoma) in an individual comprising administering to the individual (i) an effective amount of a composition comprising nanoparticles comprising a taxane (such as paclitaxel) and a carrier protein; and (ii) an effective amount of gemcitabine, wherein the dose of taxane (such as paclitaxel) in the nanoparticle composition is between about 50 mg/m$^2$ to about 400 mg/m$^2$ (including for example about 100 mg/m$^2$ to about 300 mg/m$^2$, about 100 mg/m$^2$ to about 200 mg/m$^2$, or about 100 mg/m$^2$ to about 150 mg/m$^2$, or about 100 mg/m$^2$, or about 125 mg/m$^2$, or about 150 mg/m$^2$) and the dose of gemcitabine is about 500 mg/m$^2$ to about 2000 mg/m$^2$ (for example, about 750 mg/m$^2$ to about 1500 mg/m$^2$, about 800 mg/m$^2$ to about 1200 mg/m$^2$, about 750 mg/m$^2$, about 1000 mg/m$^2$, about 1250 mg/m$^2$, or about 1500 mg/m$^2$). In some embodiments, the nanoparticle composition is administered weekly for three weeks of four weeks or weekly. In some embodiments, gemcitabine is administered weekly for three weeks of four weeks or weekly.

A combination of the administration configurations described herein can be used. A method described herein may be performed alone or in conjunction with an additional therapy, such as chemotherapy, radiation therapy, surgery, hormone therapy, gene therapy, immunotherapy, chemoimmunotherapy, cryotherapy, ultrasound therapy, liver transplantation, local ablative therapy, radiofrequency ablation therapy, photodynamic therapy, and the like.

Nanoparticle Compositions

The nanoparticle compositions described herein comprise nanoparticles comprising (in various embodiments consisting essentially of) a taxane (such as paclitaxel) and a carrier protein (e.g., an albumin such as human serum albumin or human albumin) Nanoparticles of poorly water soluble drugs (such as taxane) have been disclosed in, for example, U.S. Pat. Nos. 5,916,596; 6,506,405; 6,749,868, 6,537,579, 7,820,788, and also in U.S. Pat. Pub. Nos. 2006/0263434, and 2007/0082838; PCT Patent Application WO08/137148, each of which is incorporated by reference in their entirety.

In some embodiments, the composition comprises nanoparticles with an average or mean diameter of no greater than about 1000 nanometers (nm), such as no greater than about (or less than about) any of 900, 800, 700, 600, 500, 400, 300, 200, and 100 nm. In some embodiments, the average or mean diameters of the nanoparticles is no greater than about 200 nm (such as less than about 200 nm). In some embodiments, the average or mean diameters of the nanoparticles is no greater than about 150 nm. In some embodiments, the average or mean diameters of the nanoparticles is no greater than about 100 nm. In some embodiments, the average or mean diameter of the nanoparticles is about 20 to about 400 nm. In some embodiments, the average or mean diameter of the nanoparticles is about 40 to about 200 nm. In some embodiments, the nanoparticles are sterile-filterable.

In some embodiments, the nanoparticles in the composition described herein have an average diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least about any one of 60%, 70%, 80%, 90%, 95%, or 99%) of the nanoparticles in the composition have a diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least any one of 60%, 70%, 80%, 90%, 95%, or 99%) of the nanoparticles in the composition fall within the range of about 20 to about 400 nm, including for example about 20 to about 200 nm, about 40 to about 200 nm, about 30 to about 180 nm, and any one of about 40 to about 150, about 50 to about 120, and about 60 to about 100 nm.

In some embodiments, the carrier protein (e.g., an albumin) has sulfhydryl groups that can form disulfide bonds. In some embodiments, at least about 5% (including for example at least about any one of 10%, 15%, 20%, 25%, 30%, 40%, 50%, 60%, 70%, 80%, or 90%) of carrier protein (e.g., an albumin) in the nanoparticle portion of the composition are crosslinked (for example crosslinked through one or more disulfide bonds).

In some embodiments, the nanoparticles comprising the taxane (such as paclitaxel) are coated with a carrier protein (e.g., an albumin such as human albumin or human serum albumin) In some embodiments, the composition comprises a taxane (such as paclitaxel) in both nanoparticle and non-nanoparticle forms (e.g., in the form of paclitaxel solutions or in the form of soluble carrier protein/nanoparticle complexes), wherein at least about any one of 50%, 60%, 70%, 80%, 90%, 95%, or 99% of the taxane (such as paclitaxel) in the composition are in nanoparticle form. In some embodiments, the taxane (such as paclitaxel) in the nanoparticles constitutes more than about any one of 50%, 60%, 70%, 80%, 90%, 95%, or 99% of the nanoparticles by weight. In some embodiments, the nanoparticles have a non-polymeric matrix. In some embodiments, the nanoparticles comprise a core of a taxane (such as paclitaxel) that is substantially free of polymeric materials (such as polymeric matrix).

In some embodiments, the composition comprises a carrier protein (e.g., an albumin) in both nanoparticle and non-nanoparticle portions of the composition, wherein at least about any one of 50%, 60%, 70%, 80%, 90%, 95%, or 99% of the carrier protein (e.g., an albumin) in the composition are in non-nanoparticle portion of the composition.

In some embodiments, the weight ratio of an albumin (such as human albumin or human serum albumin) and a taxane in the nanoparticle composition is about 18:1 or less, such as about 15:1 or less, for example about 10:1 or less. In some embodiments, the weight ratio of an albumin (such as human albumin or human serum albumin) and a taxane (such as paclitaxel) in the composition falls within the range of any one of about 1:1 to about 18:1, about 2:1 to about 15:1, about 3:1 to about 13:1, about 4:1 to about 12:1, about 5:1 to about 10:1. In some embodiments, the weight ratio of an albumin and a taxane (such as paclitaxel) in the nanoparticle portion of the composition is about any one of 1:2, 1:3, 1:4, 1:5, 1:9, 1:10, 1:15, or less. In some embodiments, the weight ratio of the albumin (such as human albumin or human serum albumin) and the taxane (such as paclitaxel) in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 1:1 to about 1:1.

In some embodiments, the nanoparticle composition comprises one or more of the above characteristics.

The nanoparticles described herein may be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

In some embodiments, the pharmaceutically acceptable carrier comprises a carrier protein (e.g., an albumin such as human albumin or human serum albumin) Examples of suitable carrier proteins include proteins normally found in blood or plasma, which include, but are not limited to, an albumin, immunoglobulin including IgA, lipoproteins, apolipoprotein B, α-acid glycoprotein, β-2-macroglobulin, thyroglobulin, transferrin, fibronectin, factor VII, factor VIII, factor IX, factor X, and the like. In some embodiments, the carrier protein is non-blood protein, such as casein, α-lactalbumin, β-lactoglobulin. The proteins may either be natural in origin or synthetically prepared. In some embodiments, the protein is an albumin, such as human albumin or human serum albumin. In some embodiments, the albumin is a recombinant albumin.

Human serum albumin (HSA) is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulfide bridges, one free thiol (Cys 34), and a single tryptophan (Trp 214). Intravenous use of HSA solution has been indicated for the prevention and treatment of hypovolumic shock (see, e.g., Tullis, *JAMA*, 237: 355-360, 460-463, (1977)) and Houser et al., *Surgery, Gynecology and Obstetrics*, 150: 811-816 (1980)) and in conjunction with exchange transfusion in the treatment of neonatal hyperbilirubinemia (see, e.g., Finlayson, Seminars in Thrombosis and Hemostasis, 6, 85-120, (1980)). Other albumins are contemplated, such as bovine serum albumin Use of such non-human albumins could be appropriate, for example, in the context of use of these compositions in non-human mammals, such as the veterinary (including domestic pets and agricultural context). Human serum albumin (HSA) has multiple hydrophobic binding sites (a total of eight for fatty acids, an endogenous ligand of HSA) and binds a diverse set of taxanes, especially neutral and negatively charged hydrophobic compounds (Goodman et al., *The Pharmacological Basis of Therapeutics*, 9th ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.*, 30, 687-92 (198a), Vorum, *Dan. Med. Bull.*, 46, 379-99 (1999), Kragh-Hansen, *Dan. Med. Bull.*, 1441, 131-40 (1990), Curry et al., *Nat. Struct. Biol.*, 5, 827-35 (1998), Sugio et al., *Protein. Eng.*, 12, 439-46 (1999), He et al., *Nature*, 358, 209-15 (199b), and Carter et al., *Adv. Protein. Chem.*, 45, 153-203 (1994)). Paclitaxel and propofol have been shown to bind HSA (see, e.g., Paal et al., *Eur. J. Biochem.*, 268(7), 2187-91 (200a), Purcell et al., *Biochim. Biophys. Acta*, 1478(a), 61-8 (2000), Altmayer et al., *Arzneimittelforschung*, 45, 1053-6 (1995), and Garrido et al., *Rev. Esp. Anestestiol. Reanim.*, 41, 308-12 (1994)). In addition, docetaxel has been shown to bind to human plasma proteins (see, e.g., Urien et al., *Invest. New Drugs*, 14(b), 147-51 (1996)).

The carrier protein (e.g., an albumin such as human albumin or human serum albumin) in the composition generally serves as a carrier for the taxane, i.e., the albumin in the composition makes the taxane (such as paclitaxel)

more readily suspendable in an aqueous medium or helps maintain the suspension as compared to compositions not comprising a carrier protein. This can avoid the use of toxic solvents (or surfactants) for solubilizing the taxane, and thereby can reduce one or more side effects of administration of the taxane (such as paclitaxel) into an individual (such as a human). Thus, in some embodiments, the composition described herein is substantially free (such as free) of surfactants, such as Cremophor (or polyoxyethylated castor oil) (including Cremophor EL® (BASF)). In some embodiments, the nanoparticle composition is substantially free (such as free) of surfactants. A composition is "substantially free of Cremophor" or "substantially free of surfactant" if the amount of Cremophor or surfactant in the composition is not sufficient to cause one or more side effect(s) in an individual when the nanoparticle composition is administered to the individual. In some embodiments, the nanoparticle composition contains less than about any one of 20%, 15%, 10%, 7.5%, 5%, 2.5%, or 1% organic solvent or surfactant. In some embodiments, the carrier protein is an albumin. In some embodiments, the albumin is human albumin or human serum albumin. In some embodiments, the albumin is recombinant albumin.

The amount of a carrier protein such as an albumin in the composition described herein will vary depending on other components in the composition. In some embodiments, the composition comprises a carrier protein such as an albumin in an amount that is sufficient to stabilize the taxane (such as paclitaxel) in an aqueous suspension, for example, in the form of a stable colloidal suspension (such as a stable suspension of nanoparticles). In some embodiments, the carrier protein such as an albumin is in an amount that reduces the sedimentation rate of the taxane (such as paclitaxel) in an aqueous medium. For particle-containing compositions, the amount of the carrier protein such as an albumin also depends on the size and density of nanoparticles of the taxane.

A taxane (such as paclitaxel) is "stabilized" in an aqueous suspension if it remains suspended in an aqueous medium (such as without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (such as human). Stability of the suspension is generally (but not necessarily) evaluated at a storage temperature (such as room temperature (such as 20-25° C.) or refrigerated conditions (such as 4° C.)). For example, a suspension is stable at a storage temperature if it exhibits no flocculation or particle agglomeration visible to the naked eye or when viewed under the optical microscope at 1000 times, at about fifteen minutes after preparation of the suspension. Stability can also be evaluated under accelerated testing conditions, such as at a temperature that is higher than about 40° C.

In some embodiments, the carrier protein (e.g., an albumin) is present in an amount that is sufficient to stabilize the taxane (such as paclitaxel) in an aqueous suspension at a certain concentration. For example, the concentration of the taxane (such as paclitaxel) in the composition is about 0.1 to about 100 mg/ml, including for example any of about 0.1 to about 50 mg/ml, about 0.1 to about 20 mg/ml, about 1 to about 10 mg/ml, about 2 mg/ml to about 8 mg/ml, about 4 to about 6 mg/ml, or about 5 mg/ml. In some embodiments, the concentration of the taxane (such as paclitaxel) is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the carrier protein (e.g., an albumin) is present in an amount that avoids use of surfactants (such as Cremophor), so that the composition is free or substantially free of surfactant (such as Cremophor).

In some embodiments, the composition, in liquid form, comprises from about 0.1% to about 50% (w/v) (e.g. about 0.5% (w/v), about 5% (w/v), about 10% (w/v), about 15% (w/v), about 20% (w/v), about 30% (w/v), about 40% (w/v), or about 50% (w/v)) of carrier protein (e.g., an albumin). In some embodiments, the composition, in liquid form, comprises about 0.5% to about 5% (w/v) of carrier protein (e.g., an albumin).

In some embodiments, the weight ratio of a carrier protein (e.g., an albumin) to the taxane (such as paclitaxel) in the nanoparticle composition is such that a sufficient amount of taxane binds to, or is transported by, the cell. While the weight ratio of a carrier protein (e.g., an albumin) to taxane will have to be optimized for different carrier protein (e.g., an albumin) and taxane combinations, generally the weight ratio of carrier protein (e.g., an albumin), to taxane (such as paclitaxel) (w/w) is about 0.01:1 to about 100:1, about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, or about 9:1. In some embodiments, the carrier protein (e.g., an albumin) to taxane weight ratio is about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less. In some embodiments, the carrier protein is an albumin. In some embodiments, the weight ratio of the albumin (such as human albumin or human serum albumin) to the taxane in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 1:1 to about 1:1.

In some embodiments, the carrier protein (e.g., an albumin) allows the composition to be administered to an individual (such as human) without significant side effects. In some embodiments, the carrier protein (e.g., an albumin such as human serum albumin or human albumin) is in an amount that is effective to reduce one or more side effects of administration of the taxane (such as paclitaxel) to a human. The term "reducing one or more side effects of administration of the taxane (such as paclitaxel)" refers to reduction, alleviation, elimination, or avoidance of one or more undesirable effects caused by the taxane, as well as side effects caused by delivery vehicles (such as solvents that render the taxanes suitable for injection) used to deliver the taxane. Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with taxanes (such as paclitaxel) can be reduced.

In some embodiments, the nanoparticle compositions described herein comprises nanoparticles comprising a taxane (such as paclitaxel) and an albumin (such as human albumin or human serum albumin), wherein the nanoparticles have an average diameter of no greater than about 200 nm. In some embodiments, the nanoparticle compositions described herein comprises nanoparticles comprising a taxane (such as paclitaxel) and an albumin (such as human albumin or human serum albumin), wherein the nanoparticles have an average diameter of no greater than about 150 nm. In some embodiments, the nanoparticle compositions described herein comprises nanoparticles comprising a taxane (such as paclitaxel) and an albumin (such as human albumin or human serum albumin), wherein the nanoparticles have an average diameter of about 130 nm. In some embodiments, the nanoparticle compositions described herein comprises nanoparticles comprising paclitaxel and human albumin (such as human serum albumin), wherein the nanoparticles have an average diameter of about 130 nm.

In some embodiments, the nanoparticle compositions described herein comprises nanoparticles comprising a taxane (such as paclitaxel) and an albumin (such as human albumin or human serum albumin), wherein the nanoparticles have an average diameter of no greater than about 200 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) and an albumin (such as human albumin or human serum albumin), wherein the nanoparticles have an average diameter of no greater than about 150 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) and an albumin (such as human albumin or human serum albumin), wherein the nanoparticles have an average diameter of about 150 nm, wherein the weight ratio of the albumin and the taxane in the composition is no greater than about 9:1 (such as about 9:1). In some embodiments, the nanoparticle compositions described herein comprises nanoparticles comprising paclitaxel and human albumin (such as human serum albumin), wherein the nanoparticles have an average diameter of about 130 nm, wherein the weight ratio of albumin and the taxane in the composition is about 9:1.

In some embodiments, the nanoparticle compositions described herein comprises nanoparticles comprising a taxane (such as paclitaxel) coated with an albumin (such as human albumin or human serum albumin). In some embodiments, the nanoparticle compositions described herein comprises nanoparticles comprising a taxane (such as paclitaxel) coated with an albumin (such as human albumin or human serum albumin), wherein the nanoparticles have an average diameter of no greater than about 200 nm. In some embodiments, the nanoparticle compositions described herein comprises nanoparticles comprising a taxane (such as paclitaxel) coated with an albumin (such as human albumin or human serum albumin), wherein the nanoparticles have an average diameter of no greater than about 150 nm. In some embodiments, the nanoparticle compositions described herein comprises nanoparticles comprising a taxane (such as paclitaxel) coated with an albumin (such as human albumin or human serum albumin), wherein the nanoparticles have an average diameter of about 130 nm. In some embodiments, the nanoparticle compositions described herein comprises nanoparticles comprising paclitaxel coated with human albumin (such as human serum albumin), wherein the nanoparticles have an average diameter of about 130 nm.

In some embodiments, the nanoparticle compositions described herein comprises nanoparticles comprising a taxane (such as paclitaxel) coated with an albumin (such as human albumin or human serum albumin), wherein the weight ratio of the albumin and the taxane in the composition is no greater than about 9:1 (such as about 9:1). In some embodiments, the nanoparticle compositions described herein comprises nanoparticles comprising a taxane (such as paclitaxel) coated with an albumin (such as human albumin or human serum albumin), wherein the nanoparticles have an average diameter of no greater than about 200 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) coated with an albumin (such as human albumin or human serum albumin), wherein the nanoparticles have an average diameter of no greater than about 150 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) coated with an albumin (such as human albumin or human serum albumin), wherein the nanoparticles have an average diameter of about 150 nm, wherein the weight ratio of the albumin and the taxane in the composition is no greater than about 9:1 (such as about 9:1). In some embodiments, the nanoparticle compositions described herein comprises nanoparticles comprising paclitaxel coated with human albumin (such as human serum albumin), wherein the nanoparticles have an average diameter of about 130 nm, wherein the weight ratio of albumin and the taxane in the composition is about 9:1.

In some embodiments, the nanoparticle compositions described herein comprises nanoparticles comprising a taxane (such as paclitaxel) stabilized by an albumin (such as human albumin or human serum albumin). In some embodiments, the nanoparticle compositions described herein comprises nanoparticles comprising a taxane (such as paclitaxel) stabilized by an albumin (such as human albumin or human serum albumin), wherein the nanoparticles have an average diameter of no greater than about 200 nm. In some embodiments, the nanoparticle compositions described herein comprises nanoparticles comprising a taxane (such as paclitaxel) stabilized by an albumin (such as human albumin or human serum albumin), wherein the nanoparticles have an average diameter of no greater than about 150 nm. In some embodiments, the nanoparticle compositions described herein comprises nanoparticles comprising a taxane (such as paclitaxel) stabilized by an albumin (such as human albumin or human serum albumin), wherein the nanoparticles have an average diameter of about 130 nm. In some embodiments, the nanoparticle compositions described herein comprises nanoparticles comprising paclitaxel stabilized by human albumin (such as human serum albumin), wherein the nanoparticles have an average diameter of about 130 nm.

In some embodiments, the nanoparticle compositions described herein comprises nanoparticles comprising a taxane (such as paclitaxel) stabilized by an albumin (such as human albumin or human serum albumin), wherein the weight ratio of the albumin and the taxane in the composition is no greater than about 9:1 (such as about 9:1). In some embodiments, the nanoparticle compositions described herein comprises nanoparticles comprising a taxane (such as paclitaxel) stabilized by an albumin (such as human albumin or human serum albumin), wherein the nanoparticles have an average diameter of no greater than about 200 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) stabilized by an albumin (such as human albumin or human serum albumin), wherein the nanoparticles have an average diameter of no greater than about 150 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) stabilized by an albumin (such as human albumin or human serum albumin), wherein the nanoparticles have an average diameter of about 150 nm, wherein the weight ratio of the albumin and the taxane in the composition is no greater than about 9:1 (such as about 9:1). In some embodiments, the nanoparticle compositions described herein comprises nanoparticles comprising paclitaxel stabilized by human albumin (such as human serum albumin), wherein the nanoparticles have an average diameter of about 130 nm, wherein the weight ratio of albumin and the taxane in the composition is about 9:1.

In some embodiments, the nanoparticle composition comprises Nab-paclitaxel (or Abraxane®). In some embodiments, the nanoparticle composition is Nab-paclitaxel (or Abraxane®). Abraxane® is a formulation of paclitaxel stabilized by human albumin USP, which can be dispersed in directly injectable physiological solution. The weight ratio of human albumin and paclitaxel is about 9:1. When dispersed in a suitable aqueous medium such as 0.9% sodium chloride injection or 5% dextrose injection, Nab-paclitaxel (or Abraxane®) forms a stable colloidal suspension of paclitaxel. The mean particle size of the nanoparticles in the colloidal suspension is about 130 nanometers. Since HSA is freely soluble in water, Nab-paclitaxel (or Abraxane®) can be reconstituted in a wide range of concentrations ranging from dilute (0.1 mg/ml paclitaxel) to concentrated (20 mg/ml paclitaxel), including for example about 2 mg/ml to about 8 mg/ml, or about 5 mg/ml.

Methods of making nanoparticle compositions are known in the art. For example, nanoparticles containing taxanes (such as paclitaxel) and carrier protein (e.g., an albumin such as human serum albumin or human albumin) can be prepared under conditions of high shear forces (e.g., sonication, high pressure homogenization, or the like). These methods are disclosed in, for example, U.S. Pat. Nos. 5,916,596; 6,506,405; 6,749,868, 6,537,579 and 7,820,788 and also in U.S. Pat. Pub. Nos. 2007/0082838, 2006/0263434 and PCT Application WO08/137148.

Briefly, the taxane (such as paclitaxel) is dissolved in an organic solvent, and the solution can be added to a carrier protein solution such as an albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride or chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

Other Components in the Nanoparticle Compositions

The nanoparticles described herein can be present in a composition that includes other agents, excipients, or stabilizers. For example, to increase stability by increasing the negative zeta potential of nanoparticles, one or more of negatively charged components may be added. Such negatively charged components include, but are not limited to bile salts of bile acids consisting of glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine, stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearyolphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

In some embodiments, the composition is suitable for administration to a human. In some embodiments, the composition is suitable for administration to a mammal such as, in the veterinary context, domestic pets and agricultural animals. There are a wide variety of suitable formulations of the nanoparticle composition (see, e.g., U.S. Pat. Nos. 5,916,596, 6,096,331, and 7,820,788). The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Examples of suitable carriers, excipients, and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl and propylhydroxybenzoates, talc, magnesium stearate, and mineral oil. The formulations can additionally include lubricating agents, wetting agents, emulsifying and suspending agents, preserving agents, sweetening agents or flavoring agents.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

In some embodiments, the composition is formulated to have a pH range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 8). The composition can also be made to be isotonic with blood by the addition of a suitable tonicity modifier, such as glycerol.

Articles of Manufacture, Kits, Compositions, and Medicines

The invention also provides kits, medicines, compositions, unit dosage forms, and articles of manufacture for use in any of the methods described herein.

Kits of the invention include one or more containers comprising taxane-containing nanoparticle compositions (or unit dosage forms and/or articles of manufacture) and/or gemcitabine, and in some embodiments, further comprise instructions for use in accordance with any of the methods described herein. The kit may further comprise a description of selection of individual suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising nanoparticles comprising a taxane (such as paclitaxel) and a carrier protein (e.g., an albumin such as human serum albumin or human albumin) In some embodiments, the kit further comprises instructions for administering the nanoparticle composition in combination with gemcitabine for treatment of pancreatic cancer in an individual. For another example, in some embodiments, the kit comprises a) a composition comprising nanoparticles comprising a taxane (e.g., paclitaxel) and a carrier protein (e.g., an albumin such as human serum albumin or human albumin), b) an effective amount of gemcitabine. In some embodiments, the kit further comprises instructions for administering the nanoparticle composition and gemcitabine for treatment of pancreatic cancer in an individual. The nanoparticles and gemcitabine can be present in separate containers or in a single container. For example, the kit may comprise one distinct composition or two or more compositions wherein one composition comprises nanoparticles and one composition comprises gemcitabine. The instructions may be on a package insert or a package label. The treatment may be according to (or as applied to) any one of the methods described herein.

The kits of the invention are in suitable packaging. Suitable packaging include, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), unit dosages or unit dosage forms, bottles, jars, flexible packaging, and the like.

The instructions relating to the use of the nanoparticle compositions and/or gemcitabine generally include information as to dosage, dosing schedule, and route of administration for the intended treatment. The containers may be unit doses, bulk packages (e.g., multi-dose packages) or sub-unit doses. For example, kits may be provided that contain sufficient dosages of the taxane (such as paclitaxel) and/or gemcitabine as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the taxane (such as paclitaxel) (and/or gemcitabine) and pharmaceutical compositions and instructions for use and packaged in quantities sufficient for storage and use in pharmacies, for example, hospital pharmacies and compounding pharmacies.

Also provided are medicines, compositions, and unit dosage forms useful for the methods described herein. In some embodiments, there is provided a medicine (or composition or the unit dosage form) for use in treating pancreatic cancer in an individual, comprising effective amount of nanoparticles comprising a taxane (e.g., paclitaxel) and a carrier protein (e.g., an albumin such as human serum albumin or human albumin), and/or an effective amount of gemcitabine. In some embodiments, there is provided a medicine (or composition or a unit dosage form) for use in treating pancreatic cancer in an individual in conjunction with gemcitabine, comprising nanoparticles comprising a taxane (such as paclitaxel) and a carrier protein (e.g., an albumin such as human serum albumin).

EXEMPLARY EMBODIMENTS

The present application in some embodiments provides a method of treating metastatic pancreatic cancer in a human individual comprising administering to the individual (i) an effective amount of a composition comprising nanoparticles comprising paclitaxel and an albumin; and (ii) an effective amount of gemcitabine. In some embodiments there is provided a method of treating locally advanced pancreatic cancer in a human individual comprising administering to the individual (i) an effective amount of a composition comprising nanoparticles comprising paclitaxel and an albumin; and (ii) an effective amount of gemcitabine.

In some embodiments according to (or as applied to) any of the embodiments above, the pancreatic cancer is pancreatic adenocarcinoma.

In some embodiments according to (or as applied to) any of the embodiments above, the individual is a female or, in an alternative embodiment, a male.

In some embodiments according to (or as applied to) any of the embodiments above, the individual under 65 years old or, in an alternative embodiments, is at least about 65 years old (for example at least about 75 years old).

In some embodiments according to (or as applied to) any of the embodiments above, the primary location of the pancreatic cancer is the head of the pancreas. Alternatively, the primary location of the pancreatic cancer is the body of the pancreas or in the tail of the pancreas.

In some embodiments according to (or as applied to) any of the embodiments above, the individual has metastasis in the liver. Alternatively or in addition, the individual has pulmonary metastasis.

In some embodiments according to (or as applied to) any of the embodiments above, the individual has peritoneal carcinomatosis.

In some embodiments according to (or as applied to) any of the embodiments above, the individual has stage IV pancreatic cancer at the time of diagnosis of pancreatic cancer.

In some embodiments according to (or as applied to) any of the embodiments above, the individual has 3 or more metastatic sites.

In some embodiments according to (or as applied to) any of the embodiments above, the individual has more than 3 metastatic sites.

In some embodiments according to (or as applied to) any of the embodiments above, the individual has a serum CA19-9 level that is ≥59×ULN (Upper Limit of Normal).

In some embodiments according to (or as applied to) any of the embodiments above, the individual has Karnofsky performance status (KPS) of no more than about 90 (for example between 70 and 80).

In some embodiments according to (or as applied to) any of the embodiments above, the individual has a high level of hENT1.

In some embodiments according to (or as applied to) any of the embodiments above, the composition comprising nanoparticles comprising paclitaxel and an albumin is administered intravenously.

In some embodiments according to (or as applied to) any of the embodiments above, the dose of paclitaxel in the nanoparticle composition is about 50 mg/m$^2$ m$^2$ to about 400 mg/m$^2$.

In some embodiments according to (or as applied to) any of the embodiments above, the dose of paclitaxel in the nanoparticle composition is about 50 to about 200, such as about 100 mg/m$^2$ to about 200 mg/m$^2$, for example about 125 mg/m$^2$.

In some embodiments according to (or as applied to) any of the embodiments above, the composition comprising nanoparticles comprising paclitaxel and an albumin is administered weekly, for example weekly, three out of four weeks.

In some embodiments according to (or as applied to) any of the embodiments above, the albumin is human serum albumin.

In some embodiments according to (or as applied to) any of the embodiments above, the nanoparticles in the composition have an average diameter of no greater than about 200 nm.

In some embodiments according to (or as applied to) any of the embodiments above, the weight ratio of an albumin and paclitaxel in the nanoparticle composition is about 9:1 or less, such as about 9:1.

In some embodiments according to (or as applied to) any of the embodiments above, the paclitaxel in the nanoparticles is coated with the albumin.

In some embodiments according to (or as applied to) any of the embodiments above, the gemcitabine is administered to the individual at about 500 mg/m$^2$ to about 2000 mg/m$^2$, such as about 750 mg/m$^2$ to about 1500 mg/m$^2$, for example about 1000 mg/m$^2$.

In some embodiments according to (or as applied to) any of the embodiments above, the gemcitabine is administered weekly, for example weekly, three out of four weeks.

In some embodiments according to (or as applied to) any of the embodiments above, the gemcitabine is administered intravenously.

In some embodiments according to (or as applied to) any of the embodiments above, the method further comprises administering another chemotherapeutic agent.

In some embodiments according to (or as applied to) any of the embodiments above, the method is for first-line treatment.

Those skilled in the art will recognize that several embodiments are possible within the scope and spirit of this invention. The invention will now be described in greater detail by reference to the following non limiting examples. The following examples further illustrate the invention but, of course, should not be construed as in any way limiting its scope.

EXAMPLES

Example 1

A Randomized Phase 3 Study of Weekly Nab-Paclitaxel Plus Gemcitabine Versus Gemcitabine Alone in Patients with Metastatic Adenocarcinoma of the Pancreas (MPACT)

The MPACT study was an open-label, randomized, international, multicenter, Phase 3 study designed to compare Nab-paclitaxel plus gemcitabine administered weekly to standard treatment (gemcitabine monotherapy) with respect to overall survival (OS), progression-free survival (PFS), and tumor response in patients diagnosed with metastatic adenocarcinoma of the pancreas.

Patients were assigned to one of two treatment arms, which were: (1) Nab-paclitaxel (125 mg/m$^2$) as a 30-minute intravenous (IV) infusion, followed by gemcitabine (1000 mg/m$^2$) as a 30-minute IV infusion with Cycle 1 consisting of an 8-week cycle with Nab-paclitaxel plus gemcitabine administered on Days 1, 8, 15, 29, 36, and 43, and Cycle 2 onwards consisting of 4-week cycles with weekly administration for 3 weeks (on Days 1, 8, and 15) followed by a week of rest; or (2) gemcitabine (1000 mg/m$^2$) as a 30-minute IV infusion with Cycle 1 consisting of an 8-week cycle with gemcitabine administered on Days 1, 8, 15, 22, 29, 36, and 43, and Cycle 2 onwards consisting of 4-week cycles with weekly administration for 3 weeks (on Days 1, 8, and 15) followed by a week of rest. Treatment was continued until the patient experienced disease progression (based on investigator's assessment) or unacceptable toxicity, required palliative radiotherapy, withdrew consent, or the patient's physician felt it was no longer in the best interest of the patient to continue on treatment. Patients who had not experienced disease progression were followed with regularly scheduled spiral CT/MRI scans every 8 weeks in both arms. Patients were followed for survival until death or study closure.

The 1:1 randomization was stratified by: (1) Karnofsky performance status (PS) (70-80 versus 90-100); (2) Region (Australia, North America, Eastern/Western Europe); (3) Presence of liver metastasis (Yes vs. No).

The primary efficacy endpoint was overall survival (OS). Secondary efficacy endpoints were progression-free survival (PFS) (measured by blinded, independent radiology assessments done at 8 weeks), objective tumor response according to Response Evaluation Criteria in Solid Tumors (RECIST v. 1.0) based on Spiral computed tomography (CT) scans/magnetic resonance imaging (MRI). Other endpoints included were progression-free survival and objective response rate (ORR) by investigator review, disease control rate (DCR), time to failure (TTF), and safety/tolerability by National Cancer Institute Common Terminology Criteria for Adverse Events v. 3.0 (NCI CTCAE).

The sample size was increased prior to the interim analysis to increase the power from 80% to 90% (842 patients, 608 events) to detect a hazard ratio (HR) of 0.769 (2-sided α:0.049). 1 interim survival analysis was planned for futility. The intent-to-treat (ITT) population was evaluated for efficacy, the treated population for safety. Treatment differences in overall survival and progression-free survival were tested using stratified log-rank; objective response rates were tested using the chi-squared test.

Study endpoints were determined by analyzing the following criteria: (1) changes in serum CA 19-9 levels; (2) changes in plasma SPARC (secreted protein, acidic and rich in cysteine) levels; (3) time and duration of response (using RECIST v. 1.0); (4) disease control rate based on objective response or stable disease ≥16 weeks; (5) time to treatment failure; (6) progression-free survival and overall response rate by investigator; and (7) tumor response by PET scans using EORTC criteria and blinded radiology assessments. When assessing study endpoints, researchers examined correlations between objective tumor response as determined by CT and PET scans, molecular marker expression and efficacy, and objective tumor response as determined by PET, progression-free survival, CA 19-9 levels, SPARC levels and overall survival.

Each patient had to meet the following study inclusion criteria: (1) definitive histologically or cytologically confirmed metastatic pancreatic adenocarcinoma (definitive diagnosis was made by integrating the histopathological data within the context of the clinical and radiographic data; patients with islet cell neoplasms were excluded); (2) initial diagnosis of metastatic disease must have occurred ≤6 weeks prior to randomization in the study; (3) one or more metastatic tumors measurable by CT scan (or MRI, if patient was allergic to CT contrast media); (4) patient was a male or a non-pregnant and non-lactating female, and was ≥18 years of age (female patients of child-bearing potential, as evidenced by regular menstrual periods, must have had a negative serum pregnancy test (β-hCG) documented 72 hours prior to first administration of the study drug/s); (5) patient must not have previously received radiotherapy, surgery, chemotherapy or investigational therapy for the treatment of metastatic disease (prior treatment with 5-FU or gemcitabine administered as a radiation sensitizer in the adjuvant setting was allowed, provided at least 6 months had elapsed since completion of the last dose and no lingering toxicities were present; patients that received cytotoxic doses of gemcitabine or any other chemotherapy in the adjuvant setting were excluded); (6) adequate biological parameters as demonstrated by the following blood counts at Baseline (obtained ≤14 days prior to randomization): (a) absolute neutrophil count (ANC) ≥1.5×10$^9$/L; (b) platelet count ≥100,000/mm$^3$ (100×10$^9$/L); (c) hemoglobin (Hgb) ≥9 g/dL; (7) blood chemistry levels at baseline (obtained ≤14 days prior to randomization) of: (a) AST (SGOT), ALT (SGPT) ≤2.5× upper limit of normal range (ULN), unless liver metastases were clearly present, then ≤5×ULN was allowed; (b) total bilirubin ≤ULN; (c) Serum creatinine within normal limits or calculated clearance ≥60 mL/min/1.73 m$^2$ for patients with serum creatinine levels above or below the institutional normal value (when using creatinine clearance, actual body weight was used for calculating creatinine clearance (e.g., using the Cockroft-Gault formula; for patients with a Body Mass Index (BMI) >30 kg/m², lean body weight was used instead); (8) acceptable coagulation studies (obtained ≤14 days prior to randomization) as demonstrated by prothrombin time (PT) and partial thromboplastin time (PTT) within normal limits (±15%); (9) no clinically significant abnormalities in urinalysis results (obtained ≤14 days prior to randomization); (10) a Karnofsky performance status (KPS) ≥70 (two observers were required to assess KPS; if discrepant, the lowest assessment was considered true); (11) asymptomatic for jaundice prior to Day 1 (significant or symptomatic amounts of ascites had to have been drained prior to Day 1, and pain symptoms had to have been stable and not required modification in analgesic management prior to Day 1); and (12) patient had been informed about the nature of the study, agreed to participate, and signed the Informed Consent Form (ICF) prior to participation in any study-related activities.

A patient was ineligible for inclusion in this study if any of the following exclusion criteria applied: (1) the patient had known brain metastases, unless previously treated and well-controlled for at least 3 months (defined as clinically stable, no edema, no steroids and stable in 2 scans at least 4 weeks apart); (2) the patient had only locally advanced disease; (3) the patient had experienced a ≥10% decrease in KPS between baseline visit and within 72 hours prior to randomization; (4) the patient had a ≥20% decrease in serum albumin level between baseline visit and within 72 hours prior to randomization; (5) the patient had a history of malignancy in the last 5 years (patients with prior history of in situ cancer or basal or squamous cell skin cancer were eligible, and patients with other malignancies were eligible if they were cured by surgery alone or surgery plus radiotherapy and had been continuously disease-free for at least 5 years); (6) the patient had used Coumadin; (7) the patient had active, uncontrolled bacterial, viral, or fungal infection(s) that required systemic therapy; (8) the patient had known historical or active infection with HIV, hepatitis B, or hepatitis C; (9) the patient had undergone major surgery, other than diagnostic surgery (i.e.—surgery done to obtain a biopsy for diagnosis without removal of an organ), within 4 weeks prior to Day 1 of treatment in this study; (10) the patient had a history of allergy or hypersensitivity to any of the study drugs or any of their excipients, or the patient exhibited any of the events outlined in the Contraindications or Special Warnings and Precautions sections of the product or comparator SmPC or Prescribing Information; (11) the patient had a history of connective tissue disorders (e.g., lupus, scleroderma, arteritis nodosa); (12) the patient had a history of interstitial lung disease; (13) the patient had a history of chronic leukemias (e.g., chronic lymphocytic leukemia); (14) the patient had a high cardiovascular risk, including, but not limited to, coronary stenting or myocardial infarction in the year prior to Day 1 of the study; (15) the patient had a history of peripheral artery disease (e.g., claudication, Leo Buerger's disease); (16) the patient had serious medical risk factors involving any of the major organ systems, or serious psychiatric disorders, which could compromise the patient's safety or the study data integrity; (17) the patient was enrolled in any other clinical protocol or investigational trial; or (18) the patient was unwilling or unable to comply with study procedures, or was planning to take vacation for 7 or more consecutive days during the course of the study.

The MPACT study enrolled 861 patients (431 in the Nab-paclitaxel plus gemcitabine arm, 430 in the gemcitabine arm) with metastatic pancreatic cancer in the United States (N=476), Canada (N=63), Australia (N=120), Western Europe (N=76), and Eastern Europe (N=126).

FIG. 1 shows the MPACT study design, and Tables 4 and 5 provide patient demographics and baseline characteristics, respectively.

TABLE 4

Patient Demographics

| Variable Category/Statistic | Nab-paclitaxel + Gemcitabine (N = 431) | Gemcitabine (N = 430) | All Patients (N = 861) |
|---|---|---|---|
| Age (years) | | | |
| Median | 62.0 | 63.0 | 63.0 |
| Min, Max | 27, 86 | 32, 88 | 27, 88 |
| Age Category | | | |
| <65 years | 254 (59) | 242 (56) | 496 (58) |
| ≥65 years | 177 (41) | 188 (44) | 365 (42) |
| <75 years | 390 (90) | 381 (89) | 771 (90) |
| ≥75 years | 41 (10) | 49 (11) | 90 (10) |
| Sex, n (%) | | | |
| Female | 186 (43) | 173 (40) | 359 (42) |
| Male | 245 (57) | 257 (60) | 502 (58) |
| KPS | N = 429 | N = 429 | N = 858 |
| 90-100 | 248 (58) | 268 (62) | 516 (60) |
| 70-80 | 179 (42) | 161 (38) | 340 (40) |
| 60 | 2 (<1) | 0 | 2 (<1) |
| Time from Primary Diagnosis to Randomization | | | |
| Median (months) | 0.85 | 0.92 | 0.89 |
| Histology of Primary Diagnosis, n (%) | 431 | 429 | 860 |
| Adenocarcinoma | 426 (99) | 425 (99) | 851 (99) |
| Other | 5 (1) | 4 (1) | 9 (1) |
| Stage at Primary Diagnosis, n (%) | 431 | 430 | 861 |
| I | 10 (2) | 9 (2) | 19 (2) |
| II | 28 (6) | 16 (4) | 44 (5) |
| III | 25 (6) | 18 (4) | 43 (5) |
| IV | 336 (78) | 354 (82) | 690 (80) |
| Unknown | 32 (7) | 33 (8) | 65 (8) |
| Stage at Current Diagnosis, n (%) | 431 | 430 | 861 |
| I-III | 0 | 0 | 0 |
| IV | 431 (100) | 429 (>99) | 860 (>99) |
| Unknown | 0 | 1 (<1) | 1 (<1) |
| Current Site(s) of Metastasis, n (%) | 431 | 430 | 861 |
| Lung | 153 (35) | 184 (43) | 337 (39) |
| Peritoneal Carcinomatosis | 19 (4) | 10 (2) | 29 (3) |
| Liver | 365 (85) | 360 (84) | 725 (84) |
| Pancreatic Primary Location, n (%) | 431 | 427 | 858 |
| Head | 191 (44) | 180 (42) | 371 (43) |
| Body | 132 (31) | 136 (32) | 268 (31) |
| Tail | 105 (24) | 110 (26) | 215 (25) |
| Unknown | 3 (1) | 1 (<1) | 4 (<1) |
| Presence of Biliary Stent at Screen, n (%) | 431 | 430 | 861 |
| Yes | 80 (19) | 68 (16) | 148 (17) |
| No | 351 (81) | 362 (84) | 713 (83) |
| Previous Whipple Procedure Done, n (%) | 431 | 430 | 861 |
| Yes | 32 (7) | 30 (7) | 62 (7) |
| No | 399 (93) | 400 (93) | 799 (93) |

TABLE 5

Baseline Characteristics

| Variable | | Nab-p + Gem (n = 431) | Gem (n = 430) | All Patients (N = 861) |
|---|---|---|---|---|
| Age | Median years (min, max) | 62.0 (27, 86) | 63.0 (32, 88) | 63.0 (27, 88) |
| | ≥65 years old, % | 41 | 44 | 42 |
| Sex | Male, % | 57 | 60 | 58 |
| Karnofsky PS* | 90-100, % | 58 | 62 | 60 |
| | 70-80, % | 42 | 38 | 40 |
| Pancreatic Primary Location* | Head, % | 44 | 42 | 43 |
| | Body, % | 31 | 32 | 31 |
| | Tail, % | 24 | 26 | 25 |
| Current Site(s) of Metastasis | Lung, % | 35 | 43 | 39 |
| | Liver, % | 85 | 84 | 84 |
| # of Metastatic Sites | 1 | <1 | 0 | <1 |
| | 2 | 9 | 7 | 8 |
| | ≥3 | 90 | 93 | 92 |
| Stage at Primary Diagnosis* | I-III | 14 | 10 | 12 |
| | IV | 78 | 82 | 80 |
| Previous Whipple | Yes, % | 7 | 7 | 7 |
| Biliary Stent | Yes, % | 19 | 16 | 17 |

The treatment arms were well balanced with respect to demographics and known prognostic features, such as age, performance status, percent of patients with liver metastases, and CA19-9 levels. The median age was 63 years and 58% were men. 60% had a KPS of 90-100, 84% had liver metastases, and 39% had lung metastases. 43% of the primary lesions were in the head of the pancreas.

Figure 2:
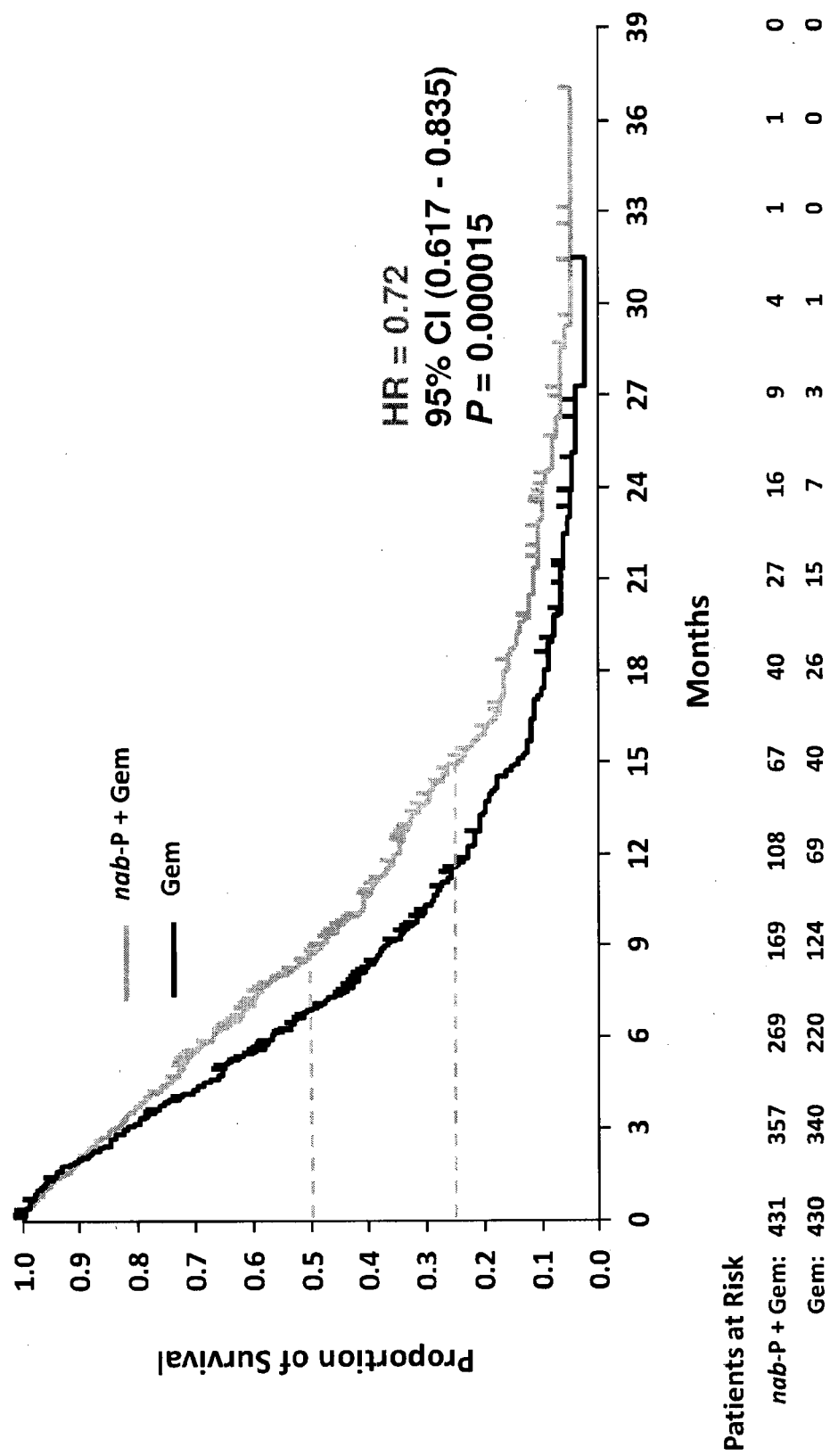
FIG. 2 shows overall survival (OS) in the intent-to-treat (ITT) population of the MPACT study.

FIG. 2 and Table 6 summarize the overall survival results.

TABLE 6

Overall Survival (Intent-to-Treat Population)

| Group | Nab-paclitaxel + Gemcitabine Death/n (%) | Gemcitabine Death/n (%) | Hazard Ratio HR (95% CI) |
|---|---|---|---|
| Age (years) | | | |
| <65 | 188/254 (74) | 209/242 (86) | 0.65 (0.528, 0.789) |
| >=65 | 145/177 (82) | 150/188 (80) | 0.81 (0.634, 1.027) |
| <75 | 301/390 (77) | 323/381 (85) | 0.69 (0.584, 0.804) |
| >=75 | 32/41 (78) | 36/49 (73) | 1.08 (0.653, 1.797) |
| Sex | | | |
| Female | 138/186 (74) | 141/173 (82) | 0.72 (0.565, 0.926) |
| Male | 195/245 (80) | 218/257 (85) | 0.72 (0.592, 0.880) |
| Karnofsky Performance Status | | | |
| 70-80 | 142/179 (79) | 146/161 (91) | 0.61 (0.481, 0.779) |
| 90-100 | 187/248 (75) | 212/268 (79) | 0.75 (0.618, 0.921) |
| Geographic Region | | | |
| Australia | 50/60 (82) | 53/59 (90) | 0.67 (0.445, 1.009) |
| Eastern Europe | 62/64 (97) | 59/62 (95) | 0.84 (0.579, 1.226) |
| Western Europe | 14/38 (37) | 17/38 (45) | 0.72 (0.352, 1.467) |
| North America | 207/268 (77) | 230/271 (85) | 0.68 (0.563, 0.823) |
| Pancreatic Cancer Primary Location | | | |
| Head | 142/191 (74) | 155/180 (86) | 0.59 (0.460, 0.745) |
| Other | 188/237 (79) | 201/246 (82) | 0.80 (0.651, 0.982) |
| Presence of Biliary Stent | | | |
| Yes | 60/80 (75) | 59/68 (87) | 0.57 (0.391, 0.839) |
| No | 273/351 (78) | 300/362 (83) | 0.74 (0.628, 0.876) |
| Previous Whipple Procedure | | | |
| Yes | 25/32 (78) | 23/30 (77) | 0.52 (0.280, 0.981) |
| No | 308/399 (77) | 336/400 (84) | 0.73 (0.623, 0.853) |
| Presence of Liver Metastases | | | |
| Yes | 290/365 (79) | 309/360 (86) | 0.69 (0.588, 0.814) |
| No | 43/66 (65) | 50/70 (71) | 0.86 (0.556, 1.327) |
| Presence of Pulmonary Metastases | | | |
| Yes | 119/153 (78) | 157/184 (85) | 0.73 (0.568, 0.929) |
| No | 214/278 (77) | 202/246 (82) | 0.73 (0.597, 0.887) |
| Peritoneal Carcinomatosis | | | |
| Yes | 9/19 (47) | 8/10 (80) | 0.44 (0.143, 1.328) |
| No | 324/412 (79) | 351/420 (84) | 0.73 (0.625, 0.849) |
| Stage at Diagnosis | | | |
| IV | 262/336 (78) | 293/354 (83) | 0.74 (0.628, 0.882) |
| Other | 52/63 (83) | 35/43 (81) | 0.84 (0.535, 1.328) |
| No. of Metastatic Sites | | | |
| 1 | 21/33 (64) | 16/21 (76) | 0.41 (0.195, 0.876) |
| 2 | 159/202 (79) | 163/206 (79) | 0.75 (0.601, 0.947) |
| 3 | 104/136 (76) | 121/140 (86) | 0.79 (0.607, 1.039) |
| Above 3 | 49/60 (82) | 59/63 (94) | 0.50 (0.325, 0.755) |
| Level of CA19-9 | | | |
| Within Normal | 47/60 (78) | 43/56 (77) | 1.07 (0.692, 1.661) |
| ULN to <59 × ULN | 96/122 (79) | 95/120 (79) | 0.83 (0.613, 1.120) |
| >=59 × ULN | 151/197 (77) | 171/195 (88) | 0.61 (0.483, 0.766) |

The median overall survival in the intent-to-treat analysis was 8.5 months in the Nab-paclitaxel plus gemcitabine arm compared with 6.7 months in the gemcitabine arm, with a hazard ratio of 0.72 (95% CI from a stratified Cox model, 0.617-0.835), which translated to a 28% reduction in the risk of death, p=0.000015, using a stratified log-rank test (FIG. 2 and Table 7).

Table 8 shows that treatment with Nab-paclitaxel plus gemcitabine increased the 1-year survival rate by 59% (from 22% in the gemcitabine arm to 35% in the Nab-paclitaxel plus gemcitabine arm) and also doubled the 2-year survival rate (from 4% to 9%).

TABLE 7

Overall Survival

| Number/Events (%) | Median (95% CI) | 3rd quartile |
|---|---|---|
| 431/333 (77%) | 8.5 (7.89-9.53) | 14.8 |
| 430/359 (83%) | 6.7 (6.01-7.23) | 11.4 |

HR = 0.72
95% CI (0.617-0.835)
P = 0.000015

TABLE 8

Survival Rate

| Time points, month | Nab-paclitaxel + Gemcitabine % survival | Gemcitabine % survival | % increase | P-value |
|---|---|---|---|---|
| 6 | 67 | 55 | 22 | 0.00074 |
| 9 | 48 | 36 | 33 | 0.00067 |
| 12 | 35 | 22 | 59 | 0.00020 |
| 18 | 16 | 9 | 78 | 0.00803 |
| 24 | 9 | 4 | 125 | 0.02123 |

Figure 3:
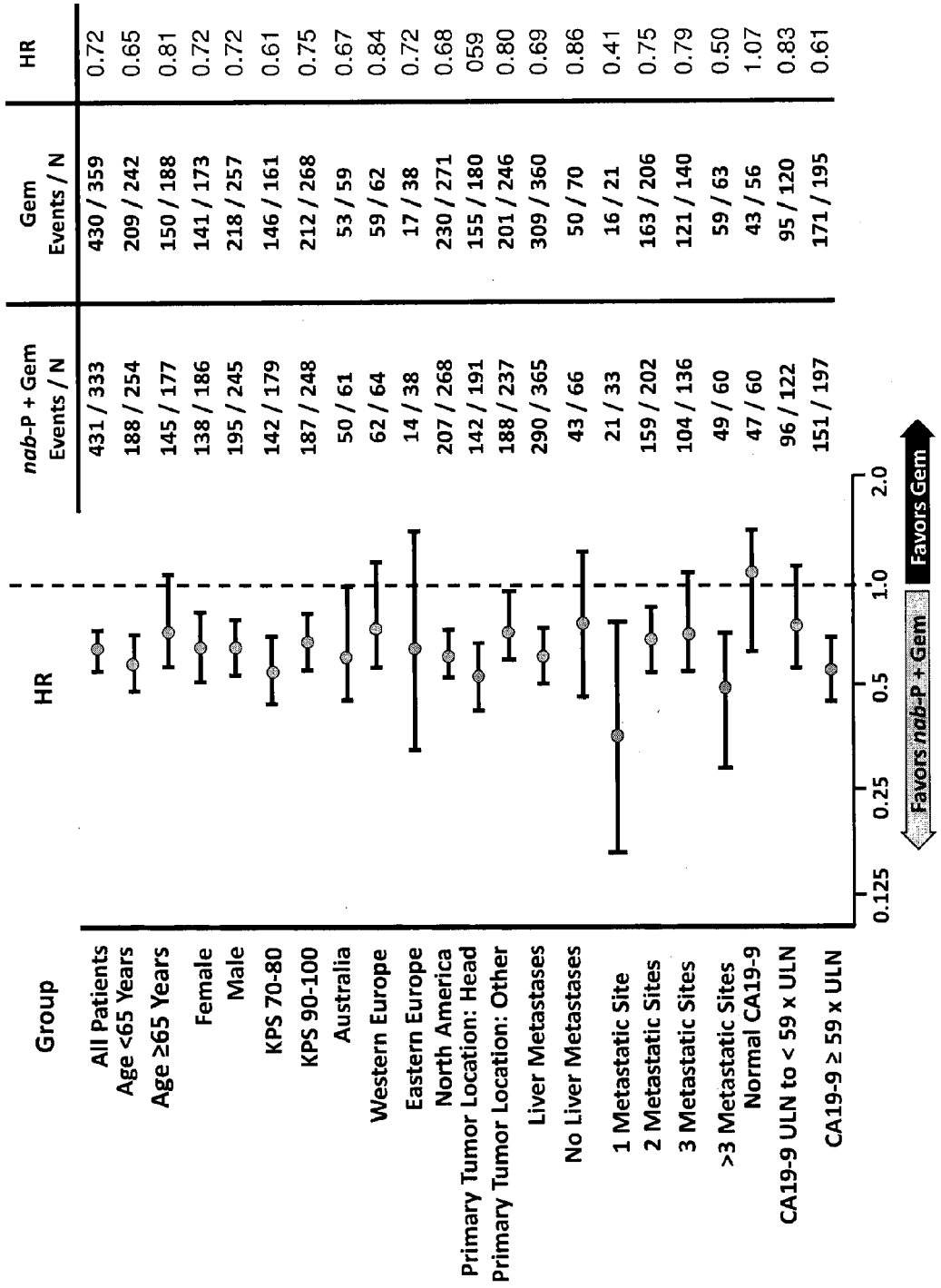
FIG. 3 shows a Forest Plot for overall survival in the intent-to-treat population of the MPACT study. Solid circles represent hazard ratios (95% CI), with values<1 favoring the combination of Nab-paclitaxel plus gemcitabine, and values>1 favoring gemcitabine alone.

FIG. 3 shows that of all the pre-specified subgroup analyses, consistent improvement in survival was observed, with the survival benefit reaching statistical significance in the majority of subgroups.

Tables 9 and 10 show that all sensitivity analyses for overall survival demonstrate a consistent, robust and statistically significant improvement in the Nab-paclitaxel plus gemcitabine arm.

TABLE 9

Overall Survival - Sensitivity Analysis

| OS Sensitivity Analysis | Nab-paclitaxel + Gemcitabine Median OS (Months) | Gemcitabine Median OS (Months) | Hazard Ratio (Nab-p + G/G) | P-value |
|---|---|---|---|---|
| Censor at Time of 2nd Line Therapy | 9.4 | 6.8 | 0.68 | <0.0001 |

TABLE 10

Cox Regression of Overall Survival with Stratified Factors as Covariates (ITT)

| Population | Nab-paclitaxel + Gemcitabine (N = 431) | Gemcitabine (N = 430) | All Patients (N = 861) |
|---|---|---|---|
| Treated Population | 420 (97%) | 403 (94%) | 823 (96%) |
| Therapy Ongoing | 26 (6%) | 12 (3%) | 38 (4%) |
| Therapy Discontinued | 394 (91%) | 391 (91%) | 785 (91%) |
| Untreated Population | 11 (3%) | 27 (6%) | 38 (4%) |
| Withdrawal by Patient | 3 (1%) | 21 (5%) | 24 (3%) |
| Patients Died | 333 (77%) | 359 (83%) | 692 (80%) |
| Patients in Survival Follow-up | 96 (22%) | 66 (15%) | 162 (19%) |
| Patients Lost to Survival Follow-up | 2 (<1%) | 5 (1%) | 7 (1%) |

Patient disposition is summarized in Table 11.

TABLE 11

Patient Disposition

| Population | Nab-paclitaxel + Gemcitabine (N = 431) | Gemcitabine (N = 430) | All Patients (N = 861) |
|---|---|---|---|
| Treated Population | 420 (97%) | 403 (94%) | 823 (96%) |
| Therapy Ongoing | 26 (6%) | 12 (3%) | 38 (4%) |
| Therapy Discontinued | 394 (91%) | 391 (91%) | 785 (91%) |
| Untreated Population | 11 (3%) | 27 (6%) | 38 (4%) |
| Withdrawal by Patient | 3 (1%) | 21 (5%) | 24 (3%) |
| Patients Died | 333 (77%) | 359 (83%) | 692 (80%) |
| Patients in Survival Follow-up | 96 (22%) | 66 (15%) | 162 (19%) |
| Patients Lost to Survival Follow-up | 2 (<1%) | 5 (1%) | 7 (1%) |

Table 12 summarizes subsequent therapy impact upon overall survival.

TABLE 12

Subsequent Therapy Impact on Overall Survival

| Drug Category Regimen | Nab-paclitaxel + Gemcitabine (N = 431) | Gemcitabine (N = 430) |
|---|---|---|
| Patients with Subsequent Therapy, % | 38 | 42 |
| 5-FU/Capecitabine based | 26 | 30 |
| Abraxane® + Capecitabine | 0 | <1% |
| FOLFIRINOX (Modified/Unmodified) | 4 | 6 |
| Erlotinib Based | 3 | 3 |
| Other | 10 | 12 |
| Abraxane®-Based |  | 6 |

Figure 4:
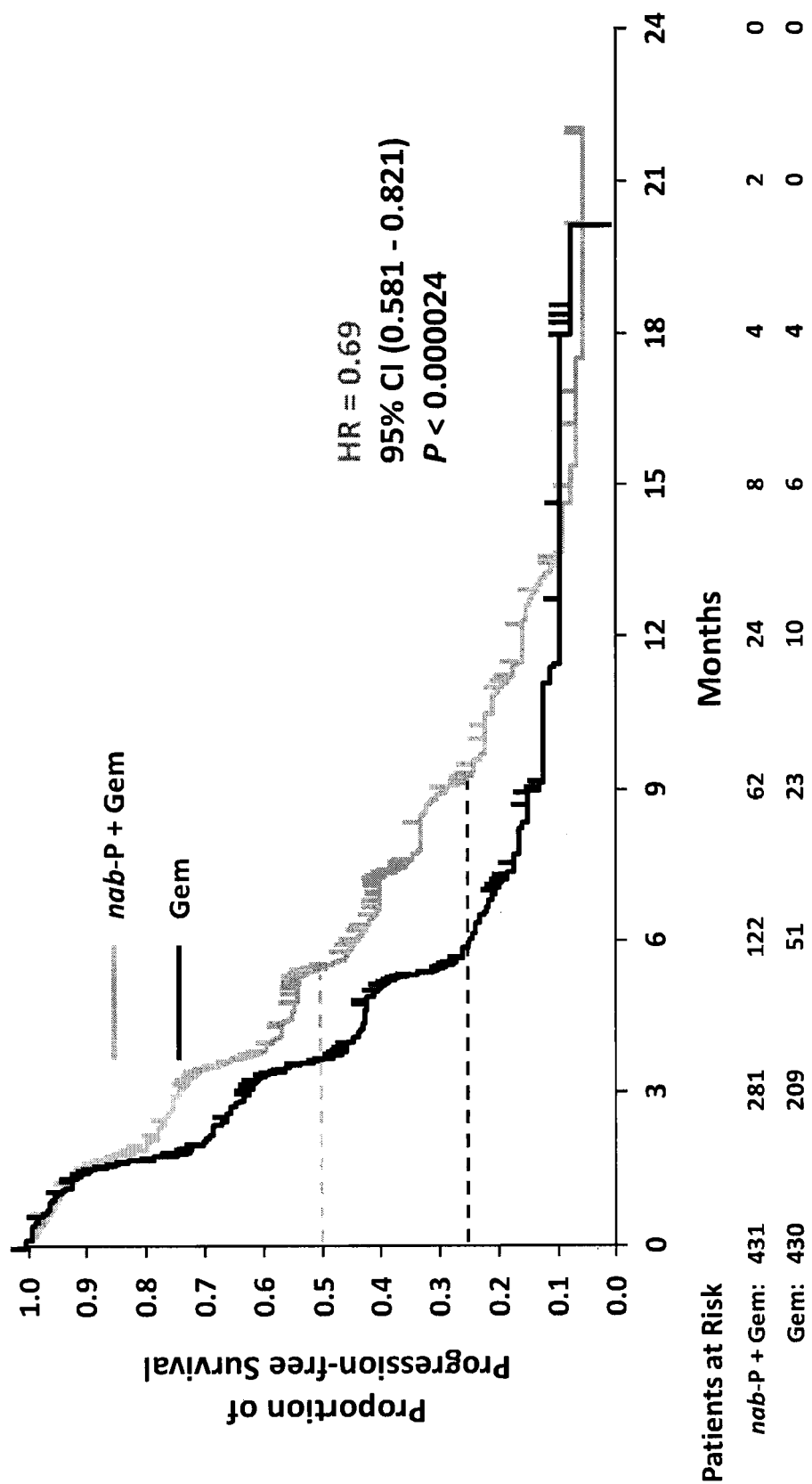
FIG. 4 shows progression-free survival (PFS) by independent radiological review of the MPACT study.

FIG. 4 and Table 13 demonstrate that the secondary endpoint of progression free survival was significantly improved. The median PFS was 3.7 months in the gemcitabine arm compared with 5.5 months in the Nab-paclitaxel plus gemcitabine arm, with a hazard ratio of 0.69, corresponding to a 31% reduction of the risk of progression or death (95% CI, 0.581-0.821; p=0.000024, stratified log-rank test). Nine and twelve month PFS rates were doubled in the Nab-paclitaxel plus gemcitabine arm. The absolute improvement in median PFS of 1.8 months was identical to the absolute improvement in median overall survival.

TABLE 13

Progression-free Survival by Independent Radiological Review (ITT Population)

| Variable | Nab-paclitaxel + Gemcitabine | Gemcitabine | Hazard Ratio (HR) (Nab-p + Gem/Gem)[a] | P-value[b] |
|---|---|---|---|---|
| N/Events | 431/277 (64%) | 430/265 (62%) | | |
| Median Progression-Free Survival (months) 95% Confidence Interval | 5.5 4.47-5.95 | 3.7 3.61-4.04 | 0.69 0.581-0.821 | 0.000024 |

| Progression-free rate (%) at | | | % Increase | |
|---|---|---|---|---|
| 6 month | 44% | 25% | 59% | |
| 9 month | 29% | 14% | | |
| 12 month | 16% | 9% | 125% | |
| 15 month | 8% | 9% | | |

Figure 5:
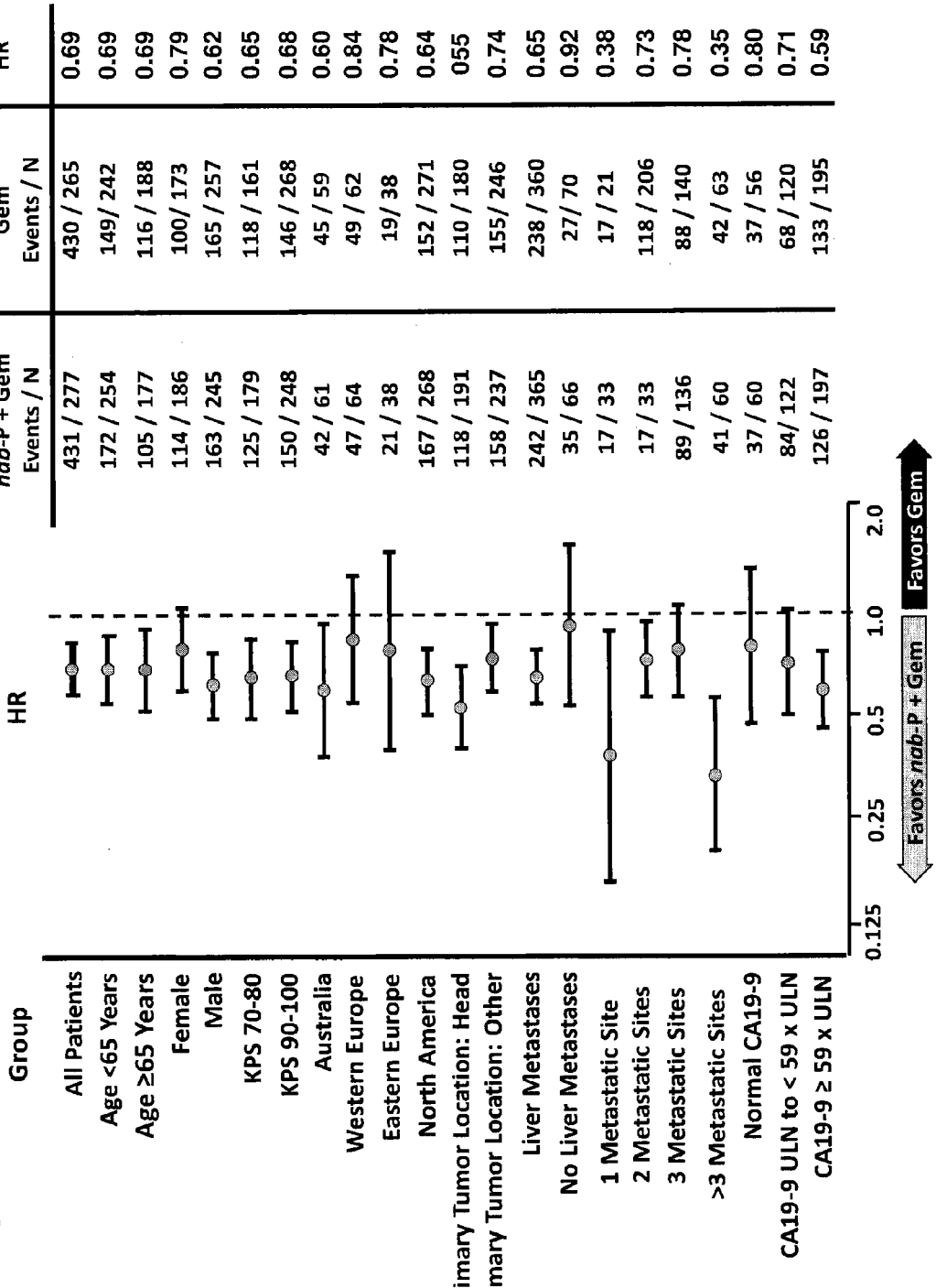
FIG. 5 shows a Forest Plot for progression-free survival by independent radiological review in the intent-to-treat population of the MPACT study. Solid circles represent hazard ratios (95% CI), with values<1 favoring the combination of Nab-paclitaxel plus gemcitabine and values>1 favoring gemcitabine alone.

[a]95% CI from stratified Cox model
[b]Stratified log-rank using IVRS strata of Region, KPS, and presence of liver metastasis FIG. 5 shows that of all the pre-specified subgroup analyses, consistent improvement on progression-free survival was observed, and this observed PFS benefit reached statistical significance in the majority of subgroups.

Figure 6:
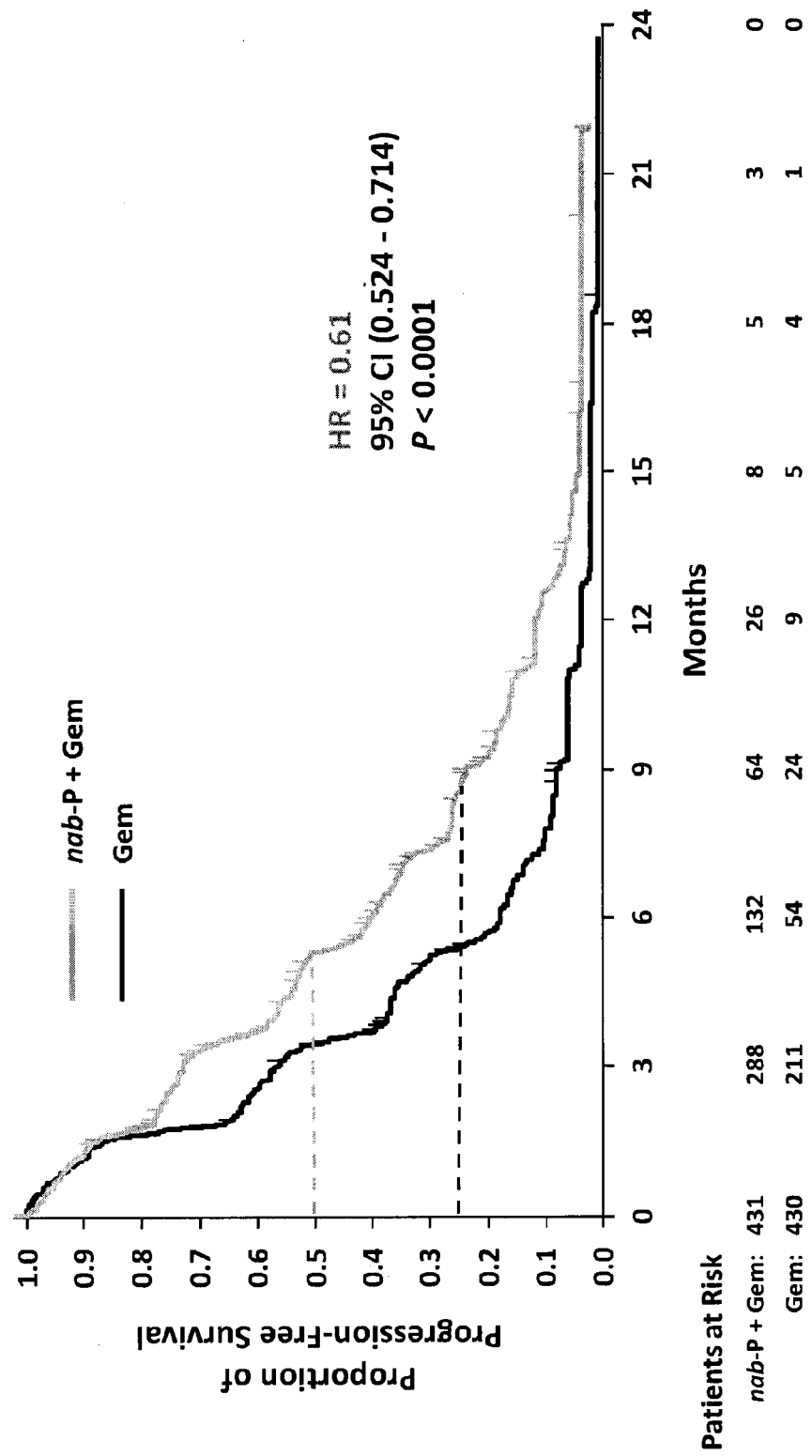
FIG. 6 shows progression-free survival by investigator review for the MPACT study.

FIG. 6 and Table 14 show the median PFS by investigator review was 3.5 months in the gemcitabine arm compared with 5.3 months in the Nab-paclitaxel plus gemcitabine arm, with a hazard ratio of 0.61 (95% CI (0.524-0.714), P<0.0001).

TABLE 14

Progression-free Survival by Investigator Review

| Variable | Nab-paclitaxel + Gemcitabine | Gemcitabine | Hazard Ratio (HR) (Nab-p + Gem/Gem) | P-value |
|---|---|---|---|---|
| N/Events | 431/327 (76%) | 430/348 (81%) | | |
| Median Progression-Free Survival (months) 95% Confidence Interval | 5.3 4.40-5.49 | 3.5 3.25-3.65 | 0.61 0.524-0.714 | <0.0001 |

Table 15 shows the blinded radiology assessed confirmed complete or partial overall response rate (ORR) in the intent-to-treat population was tripled from 7% in the gemcitabine arm to 23% in the Nab-paclitaxel plus gemcitabine arm, with a response rate ratio equal to 3.19 (p value $1.1 \times 10^{-10}$).

TABLE 15

Response Rates

| Variable | Nab-p + Gemcitabine (N = 431) | Gemcitabine (N = 430) | Response Rate Ratio ($P_{Nab-p+/Gem}/P_{Gem}$) | P-value |
|---|---|---|---|---|
| ORR | | | | |
| Blinded Assessment, % (95% CI) | 23 (19.1-27.2) | 7 (5.0-10.1) | 3.19 (2.178-4.662) | $1.1 \times 10^{-10}$ |
| Investigator Assessment, % (95% CI) 95% Confidence Interval | 29 (25.0-33.8) | 8 (5.3-10.6) | 3.81 (2.660-5.456) | $3.3 \times 10^{-16}$ |

TABLE 15-continued

Response Rates

| Variable | Nab-p + Gemcitabine (N = 431) | Gemcitabine (N = 430) | Response Rate Ratio ($P_{Nab-p+/Gem}/P_{Gem}$) | P-value |
|---|---|---|---|---|
| Best Response by Blinded Assessment | | | | |
| Complete Response, % | <1 | 0 | | |
| Partial Response, % | 23 | 7 | | |
| Stable Disease, % | 27 | 28 | | |
| Progressive Disease, % | 20 | 26 | | |
| Not evaluable, % | 30 | 39 | | |

Figure 7:
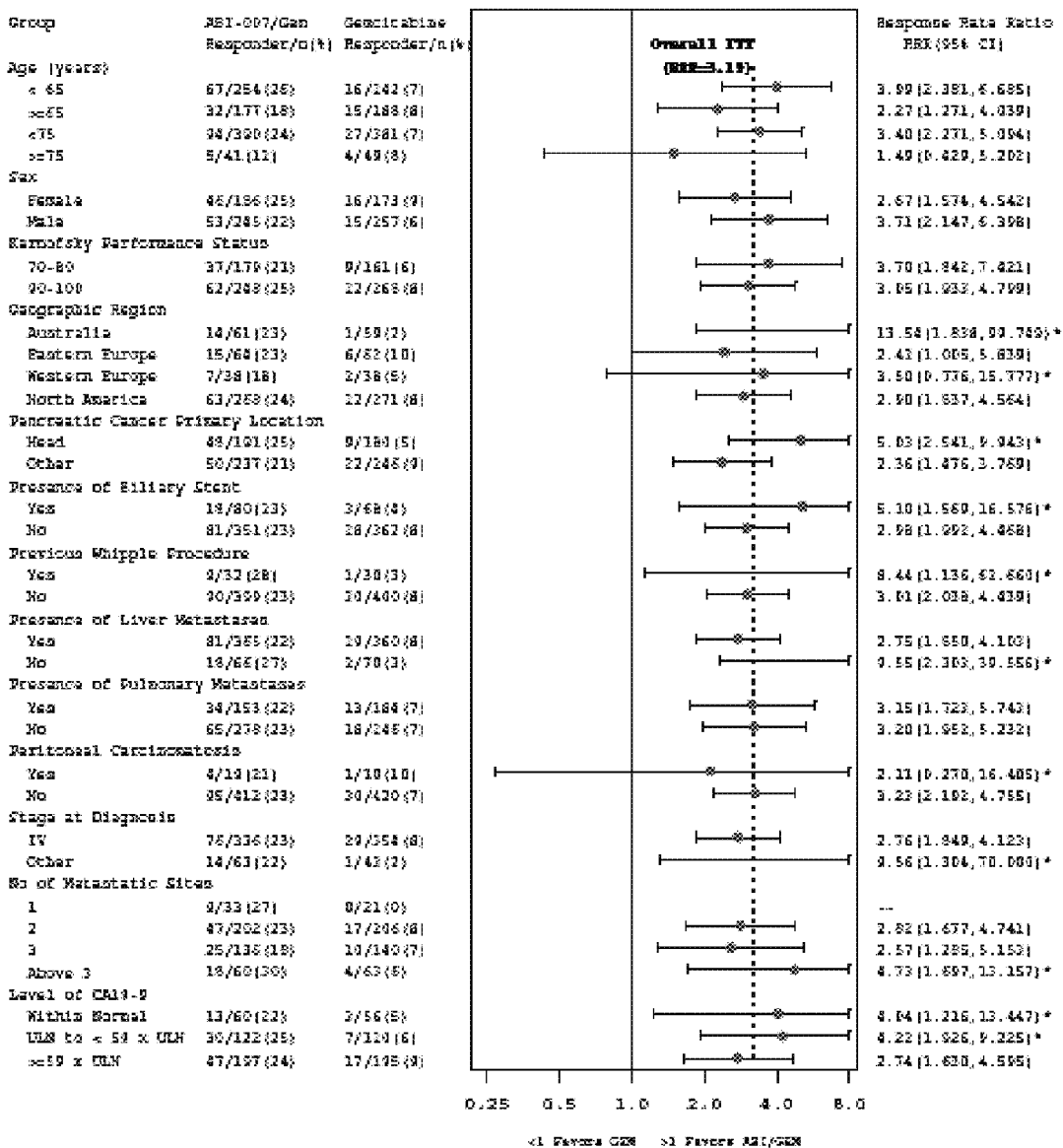
FIG. 7 shows a Forest Plot for best overall response rate by independent radiological review in the intent-to-treat population of the MPACT study. Solid circles represent hazard ratios (95% CI), with values<1 favoring gemcitabine alone (GRM) and values>1 favoring the combination of Nab-paclitaxel (Abraxane®) plus gemcitabine (ABI/GRM).

FIG. 7 demonstrates that, consistent with the improvement in overall survival and progression-free survival, subgroup analyses for overall response rate show a robust and consistent benefit in the Nab-paclitaxel plus gemcitabine arm.

Table 16 shows the disease control rate by independent review was 48% for the Nab-paclitaxel plus gemcitabine arm versus 33% for the gemcitabine arm, for a response rate ratio of 1.46.

TABLE 16

Disease Control Rate by Independent Review

| Variable | Nab-p + gemcitabine (N = 431) | gemcitabine (N = 430) | Response Rate Ratio ($P_{Nab-p+/Gem}/P_{Gem}$) | P-value |
|---|---|---|---|---|
| DCR, % | 48 | 33 | 1.46 | <0.0001 |
| (95% CI) | (43.0-52.6) | (28.4) | (1.233-1.723) | |
| Complete Response, % | <1 | 0 | | |
| Partial Response, % | 23 | 7 | | |
| Stable Disease ≥16 weeks, % | 25 | 26 | | |

Figure 8:
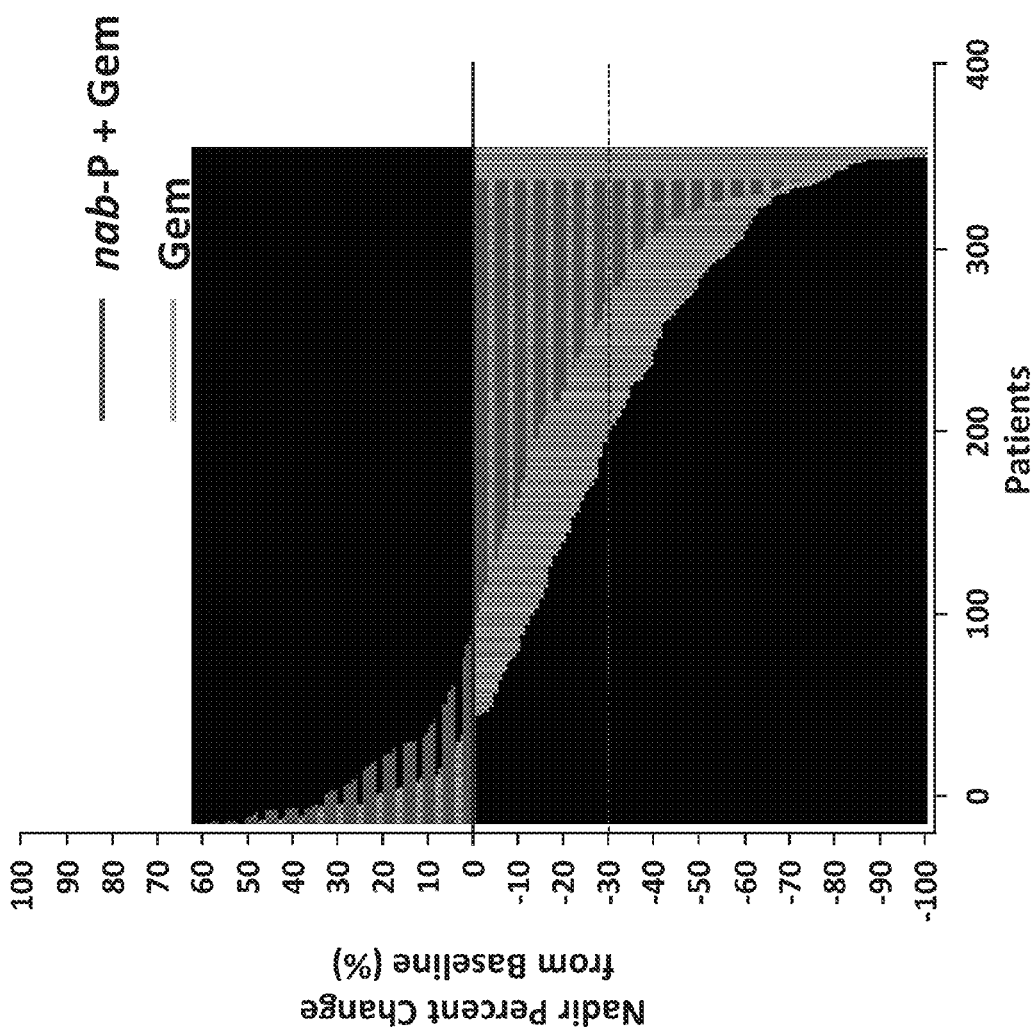
FIG. 8 shows the % change from baseline at nadir of sum of longest diameter of target lesions for the MPACT study.

FIG. 8 shows the percent change from baseline at nadir of sum of longest diameter of target lesions (maximum percent changes >100% were truncated at 100%). Table 17 shows the time to treatment failure by independent radiological review.

TABLE 17

Time to Treatment Failure by Independent Radiological Review

| Variable | Nab-p + Gemcitabine (N = 431) | Gemcitabine (N = 430) | Response Rate Ratio ($P_{Nab-p+/Gem}/P_{Gem}$)[a] | P-value[b] |
|---|---|---|---|---|
| Patients with Treatment Failure, % | 89 | 94 | | |
| Patients Censored, % | 11 | 6 | | |
| Median TTF, months | 5.1 (4.07-5.52) | 3.6 (3.48-3.88) | 0.70 (0.604-0.803) | <0.0001 |

[a]95% CI from stratified Cox model
[b]Stratified log-rank using IVRS strata of Region, KPS, and presence of liver metastasis Patients on the Nab-paclitaxel plus gemcitabine arm received one more cycle of treatment compared to the patients in the gemcitabine arm (Table 18).

TABLE 18

Treatment Exposure

| Variable | Nab-paclitaxel + Gemcitabine (N = 421) | Gemcitabine (N = 402) |
|---|---|---|
| Treatment Duration, median month | 3.9 | 2.8 |
| Cycle, median # (min, max) | 3.0 (1, 23) | 2.0 (1, 23) |
| % Protocol Dose, median (min, max) | | |
| Nab-paclitaxel | 80.6 (16.7, 100.0) | — |
| gemcitabine | 75.2 (14.3, 97.7) | 84.6 (14.1, 100.0) |
| Cumulative Dose, median mg/m² | | |
| Nab-paclitaxel | 1425.0 | — |
| gemcitabine | 11400.0 | 9000.0 |
| Dose Intensity, median mg/m²/week | | |
| Nab-paclitaxel | 74.1 | — |
| gemcitabine | 597.3 | 674.8 |
| Patients with ≥1 Dose Reduction, % | | |
| Nab-paclitaxel | 41 | — |
| gemcitabine | 47 | 33 |
| Nab-paclitaxel doses at 125 mg/m², n (%) | 4116.0 (71) | — |
| gemcitabine doses at 1000 mg/m², n (%) | 3731.0 (63) | 3762.0 (79) |

The median dose intensity of gemcitabine was only about 10% lower in the Nab-paclitaxel plus gemcitabine arm, indicating that Abraxane® allows adequate dosing of gemcitabine (Table 18). The Abraxane® dose intensity delivered was 80% of the planned dose, which was high (Table 18).

Table 19 summarizes safety results.

TABLE 19

Safety

| Preferred Term | Nab-paclitaxel + Gemcitabine (N = 421) | Gemcitabine (N = 402) |
|---|---|---|
| Pt with at least 1 AE leading to death, % | 4 | 4 |
| Grade ≥3 Nonhematologic AE[a] in >5% pts, % | | |
| Neutropenia | 38 | 27 |
| Leukopenia | 31 | 16 |
| Thrombocytopenia | 13 | 9 |
| Anemia | 13 | 12 |
| Febrile Neutropenia[b] (any grade), % | 3 | 1 |
| Grade ≥3 Nonhematologic AE[a] in >5% pts, % | | |
| Fatigue | 17 | 7 |
| Peripheral neuropathy[1] | 17 | <1 |
| Diarrhea | 7 | 2 |
| Grade ≥3 Neuropathy, median days | | |
| Time to Onset | 140 | 113 |
| Time to Improvement by 1 grade | 21 | 29 |
| Time to Improvement to grade ≤1 | 29 | — |

[a]Based on lab values
[b]Based on investigator assessment of treatment-related events
[1]61% patients in the Nab-paclitaxel arm resumed treatment after grade ≥3 neuropathy The majority of patients discontinued treatment for progression, with a higher percentage in the gemcitabine arm. However, in the combination arm, more patients discontinued for adverse events (Table 20).

TABLE 20

Treatment Discontinuation

| Population | Nab paclitaxel + Gemcitabine (N = 431) | Gemcitabine (N = 430) | All Patients (N = 861) |
|---|---|---|---|
| Patients Treated | 420 (97%) | 403 (94%) | 823 (96%) |
| Reason for Therapy Discontinuation | | | |
| Progressive Disease | 196 (45%) | 245 (57%) | 441 (51%) |
| Adverse Events | 128 (30%) | 73 (17%) | 201 (23%) |
| Related to Study Drug | 86 (20%) | 29 (7%) | 115 (13%) |
| Unrelated to Study Drug | 42 (10%) | 44 (0%) | 86 (10%) |
| Physician Decision | 25 (6%) | 18 (4%) | 43 (5%) |
| Protocol Violation | 10 (2%) | 6 (1%) | 16 (2%) |
| Lost to Follow-up | 0 | 0 | 0 |
| Withdrawal by Patient | 28 (6%) | 39 (9%) | 67 (8%) |
| Other | 7 (2%) | 10 (2%) | 17 2%) |

The Grade 3-4 adverse events that were seen in a higher percentage of patients in the Nab-paclitaxel plus gemcitabine arm were neutropenia, fatigue, peripheral neuropathy, thrombocytopenia, anemia, dehydration, nausea, and diarrhea. The rate of grade 3-4 neuropathy was 17% (Table 21). By central lab, there was a higher rate of grade 3-4 neutropenia and thrombocytopenia, but no difference in anemia (Table 21).

TABLE 21

Incidence of Most Frequent Treatment-Emergent Grade 3 or Higher AEs Reported by >5% in Either Arm (Treated Population)

| Preferred Term | Nab-paclitaxel Gemcitabine (n = 421) | Gemcitabine (n = 402) |
|---|---|---|
| Neutropenia | 138 (33%) | 85 (21%) |
| Fatigue | 77 (18%) | 37 (9%) |
| Peripheral neuropathy[1] | 70 (17%) | 3 (1%) |
| Thrombocytopenia | 53 (13%) | 33 (8%) |
| Anemia | 49 (12%) | 32 (8%) |
| Leukopenia | 39 (9%) | 15 (4%) |
| Dehydration | 31 (7%) | 10 (2%) |
| Asthenia | 29 (7%) | 17 (4%) |
| Abdominal pain | 27 (6%) | 32 (8%) |
| Nausea | 27 (6%) | 14 (3%) |
| Diarrhea | 26 (6%) | 6 (1%) |
| Vomiting | 25 (6%) | 15 (4%) |
| Pulmonary Embolism | 19 (5%) | 26 (6%) |

There was no increase in hemorrhages resulting from the small increase in thrombocytopenia. There was a small increase in infections in the combination arm, consistent with the higher rate of neutropenia and the longer observation period (Table 22).

TABLE 22

Grade 3/4 Myelosuppression

| NCI CTCAE Grade | Nab-paclitaxel Gemcitabine (N = 421) n (%) | Gemcitabine (N = 402) n (%) |
|---|---|---|
| ANC | | |
| Grade 3 | 108 (27) | 82 (21) |
| Grade 4 | 45 (11) | 21 (5) |
| Platelet Count | | |
| Grade 3 | 43 (11) | 28 (7) |
| Grade 4 | 9 (2) | 8 (2) |
| Hemoglobin | | |
| Grade 3 | 50 (12) | 42 (11) |
| Grade 4 | 3 (1) | 6 (2) |

The most common adverse event leading to drug discontinuation in a greater percentage of patients in the combination arm was sensory neuropathy (Table 23).

TABLE 23

Treatment Emergent Adverse Events Resulting in Treatment Discontinuation (≥3%)

| System Organ Class | Nab-paclitaxel + Gemcitabine (N = 421) n (%) | | Gemcitabine (N = 402) n (%) |
|---|---|---|---|
| | Nab-paclitaxel | gemcitabine | |
| Subjects with at least one AE with Action of Study Drug Permanently Discontinued | 148 (35%) | 126 (30%) | 95 (24%) |
| Nervous System | 39 (9%) | 21 (5%) | 7 (2%) |
| General Disorders/ Administration Site Condition | 30 (7%) | 28 (7%) | 18 (4%) |
| Blood & Lymphatic | 17 (4%) | 15 (4%) | 16 (4%) |
| Respiratory, Thoracic and mediastinal disorders | 16 (4%) | 16 (4%) | 15 (4%) |

TABLE 23-continued

Treatment Emergent Adverse Events Resulting in
Treatment Discontinuation (≥3%)

| System Organ Class | Nab-paclitaxel + Gemcitabine (N = 421) n (%) | | Gemcitabine (N = 402) n (%) |
|---|---|---|---|
| | Nab-paclitaxel | gemcitabine | |
| Infections and infestations | 15 (4%) | 15 (4%) | 11 (3%) |
| Gastrointestinal disorders | 14 (3%) | 15 (4%) | 22 (5%) |

The percentage of patients who had an adverse event with an outcome of death was identical in both treatment arms and low at 4% (Table 24).

TABLE 24

Treatment Emergent Adverse Events with Outcome of Death
(≥2 Patients Pooled) Treated Population

| System Organ Class - Preferred Term | Nab-paclitaxel + Gemcitabine (N = 421) n (%) | Gemcitabine (N = 402) n (%) |
|---|---|---|
| Subject with at Least 1 Treatment Related AE with Outcome of Death | 18 (4%) | 18 (4%) |
| Infections and infestations | 7 (2%) | 3 (1%) |
| Cardiac Disorders | 2 (<1%) | 3 (1%) |
| Gastrointestinal disorders | 2 (<1%) | 3 (1%) |
| General disorders and administration site conditions | 2 (<1%) | 3 (1%) |
| Respiratory, thoracic and mediastinal disorders | 2 (<1%) | 3 (1%) |
| Hepatobiliary disorders | 1 (<1%) | 1 (<1%) |
| Nervous system disorders | 1 (<1%) | 2 (<1%) |
| Renal and urinary disorders | 1 (<1%) | 1 (<1%) |
| Neoplasm Progression | 0 | 2 (<1%) |

Table 25 summarizes overall survival by subgroups in the intent-to-treat population.

| Subgroup | Nab-paclitaxel + Gemcitabine (N = 431) | | Gemcitabine (N = 430) | | Hazard Ratio $HR_{A+G/G}$ 95% CI | P-value |
|---|---|---|---|---|---|---|
| | Death/n (%) | Median OS 95% CI (months) | Death/n (%) | Median OS 95% CI (months) | | |
| Geographic Region | | | | | | |
| Australia | 50/61 (82) | 9.2 (6.90, 11.01) | 53/59 (90) | 6.7 (7.29, 8.90) | 0.67 (0.445, 1.009) | 0.0553 |
| Eastern Europe | 62/64 (97) | 7.7 (6.01, 9.26) | 59/62 (95) | 5.9 (4.67, 7.46) | 0.84 (0.579, 1.226) | 0.3715 |
| Western Europe | 14/38 (37) | — | 17/38 (45) | 6.9 (5.09, —) | 0.72 (0.352, 1.467) | 0.3644 |
| North America | 207/268 (77) | 8.7 (7.89, 9.86) | 230/271 (85) | 6.8 (6.01, 7.52) | 0.68 (0.563, 0.823) | <0.0001 |
| Pancreatic Cancer Primary Location | | | | | | |
| Head | 142/191 (74) | 9.3 (7.98, 10.45) | 155/180 (86) | 6.5 (5.55, 7.29) | 0.59 (0.460, 0.745) | <0.0001 |
| Other | 188/237 (79) | 8.1 (6.83, 9.20) | 201/246 (82) | 6.9 (5.98, 7.52) | 0.80 (0.651, 0.982) | 0.0325 |

In this multinational, multi-institutional study carried out in a highly representative patient population, Nab-paclitaxel plus gemcitabine provides a robust, highly significant improvement in survival compared with gemcitabine alone for patients with metastatic pancreatic cancer. Nab-paclitaxel plus gemcitabine is the first chemotherapy doublet to significantly improve survival in metastatic pancreatic cancer, with a median overall survival of 8.5 months in the Nab-paclitaxel plus gemcitabine arm versus 6.7 months in the gemcitabine arm (HR=0.72, p=0.0000152). Treatment with Nab-paclitaxel plus gemcitabine resulted in a 59% increase in one year survival, from 22% in the gemcitabine arm to 35% in the Nab-paclitaxel plus gemcitabine arm, and doubled the two-year survival rate (4% to 9%).

Independently reviewed secondary endpoints demonstrated consistent and significant improvements, with median progression-free survival of 5.5 months in the Nab-paclitaxel plus gemcitabine arm versus 3.7 months in the gemcitabine arm (HR=0.69, p=0.000024), an objective response rate (ORR) of 23% (compared to 7% for the gemcitabine arm), an ORR ratio of 3.19 ($P=1.1\times10^{-10}$). Serious life-threatening toxicity was not increased and adverse events were acceptable and manageable. The results of this study were consistent across subgroups, and supported by all efficacy endpoints, demonstrating Nab-paclitaxel plus gemcitabine is superior to gemcitabine alone in the treatment of metastatic pancreatic cancer.

Although the foregoing invention has been described in some detail by way of illustration and example for purposes of clarity of understanding, the descriptions and examples should not be construed as limiting the scope of the invention.

What is claimed is:

1. A method of treating metastatic or locally advanced pancreatic cancer in a human individual comprising administering to the individual (a) an effective amount of a composition comprising nanoparticles comprising paclitaxel and an albumin; and (b) an effective amount of gemcitabine, wherein the individual is selected for treatment based on (i) having metastasis in the liver, (ii) having more than 3 metastatic sites, (iii) having pancreatic cancer in the primary location in the head of the pancreas, or (iv) having serum CA19-9 level that is ≥59×ULN (Upper Limit of Normal).

2. The method of claim 1, wherein the pancreatic cancer is pancreatic adenocarcinoma.

3. The method of claim 1, wherein the individual has Karnofsky performance status (KPS) of between 70 and 80.

4. The method of claim 1, wherein the individual has a high level of hENT1 (human equilibrative nucleoside transporter 1).

5. The method claim 1, wherein the composition comprising nanoparticles comprising paclitaxel and albumin is administered intravenously.

6. The method of claim 1, wherein the dose of paclitaxel in the nanoparticle composition is about 50 mg/m² to about 200 mg/m².

7. The method of claim 6, wherein the dose of paclitaxel in the nanoparticle composition is about 125 mg/m².

8. The method of claim 6, wherein the composition comprising nanoparticles comprising paclitaxel and albumin is administered weekly, three out of four weeks.

9. The method of claim 1, wherein the albumin is human serum albumin.

10. The method of claim 1, wherein the nanoparticles in the composition have an average diameter of no greater than about 200 nm.

11. The method of claim 1, wherein the weight ratio of albumin and paclitaxel in the nanoparticle composition is about 9:1 or less.

12. The method of claim 1, wherein the paclitaxel in the nanoparticles is coated with the albumin.

13. The method of claim 1, wherein gemcitabine is administered to the individual at about 500 mg/m$^2$ to about 2000 mg/m$^2$.

14. The method of claim 13, wherein gemcitabine is administered to the individual at about 1000 mg/m$^2$.

15. The method of claim 13, wherein gemcitabine is administered weekly, three out of four weeks.

16. The method of claim 13, wherein gemcitabine is administered intravenously.

17. The method of claim 1, wherein the method is for first-line treatment.

18. The method of claim 1, further comprising selecting the individual for treatment based on the individual (i) having metastasis in the liver, (ii) having more than 3 metastatic sites, (iii) having pancreatic cancer in the primary location in the head of the pancreas, or (iv) having serum CA19-9 level that is ≥59×ULN (Upper Limit of Normal).

19. The method of claim 1, further comprising determining (i) the metastasis status, (ii) primary location of the pancreatic cancer, or (iii) CA19-9 level in the individual.

20. The method of claim 10, wherein the paclitaxel in the nanoparticles is coated with the albumin, and wherein the weight ratio of albumin and paclitaxel in the nanoparticle composition is about 9:1 or less.

21. The method of claim 1, wherein the individual is selected for treatment based on having metastasis in the liver.

22. The method of claim 21, wherein the nanoparticles in the composition have an average diameter of no greater than about 200 nm, wherein the paclitaxel in the nanoparticles is coated with the albumin, and wherein the weight ratio of albumin and paclitaxel in the nanoparticle composition is about 9:1 or less.

23. The method of claim 1, wherein the individual is selected for treatment based on having more than 3 metastatic sites.

24. The method of claim 23, wherein the nanoparticles in the composition have an average diameter of no greater than about 200 nm, wherein the paclitaxel in the nanoparticles is coated with the albumin, and wherein the weight ratio of albumin and paclitaxel in the nanoparticle composition is about 9:1 or less.

25. The method of claim 1, wherein the individual is selected for treatment based on having pancreatic cancer in the primary location in the head of the pancreas.

26. The method of claim 25, wherein the nanoparticles in the composition have an average diameter of no greater than about 200 nm, wherein the paclitaxel in the nanoparticles is coated with the albumin, and wherein the weight ratio of albumin and paclitaxel in the nanoparticle composition is about 9:1 or less.

27. The method of claim 1, wherein the individual is selected for treatment based on having serum CA19-9 level that is ≥59×ULN (Upper Limit of Normal).

28. The method of claim 27, wherein the nanoparticles in the composition have an average diameter of no greater than about 200 nm, wherein the paclitaxel in the nanoparticles is coated with the albumin, and wherein the weight ratio of albumin and paclitaxel in the nanoparticle composition is about 9:1 or less.

29. The method of claim 11, wherein the weight ratio of albumin and paclitaxel in the nanoparticle composition is about 9:1.

30. The method of claim 20, wherein the weight ratio of albumin and paclitaxel in the nanoparticle composition is about 9:1.

31. The method of claim 22, wherein the weight ratio of albumin and paclitaxel in the nanoparticle composition is about 9:1.

32. The method of claim 24, wherein the weight ratio of albumin and paclitaxel in the nanoparticle composition is about 9:1.

33. The method of claim 26, wherein the weight ratio of albumin and paclitaxel in the nanoparticle composition is about 9:1.

34. The method of claim 28, wherein the weight ratio of albumin and paclitaxel in the nanoparticle composition is about 9:1.

* * * * *

UNITED STATES PATENT AND TRADEMARK OFFICE
CERTIFICATE OF CORRECTION

Page 1 of 1

PATENT NO.       : 9,511,046 B2
APPLICATION NO.  : 13/794480
DATED            : December 6, 2016
INVENTOR(S)      : Neil P. Desai It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 307 days.

Signed and Sealed this
Twenty-first Day of November, 2017

Joseph Matal
*Performing the Functions and Duties of the*
*Under Secretary of Commerce for Intellectual Property and*
*Director of the United States Patent and Trademark Office*